US008846032B2

(12) United States Patent
Liu et al.

(10) Patent No.: US 8,846,032 B2
(45) Date of Patent: *Sep. 30, 2014

(54) MDCK CELL LINES SUPPORTING VIRAL GROWTH TO HIGH TITERS AND BIOREACTOR PROCESS USING THE SAME

(75) Inventors: Jonathan Liu, Milpitas, CA (US); Richard Schwartz, Bethesda, MD (US); Mark Thompson, Morgan Hill, CA (US); Luis Maranga, Santa Clara, CA (US); Mridul Ghosh, San Jose, CA (US); Ajit Subramanian, Berkeley, CA (US); Simon Sheng-Tsiung Hsu, Palo Alto, CA (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/595,897

(22) Filed: Aug. 27, 2012

(65) Prior Publication Data
US 2013/0052717 A1 Feb. 28, 2013

Related U.S. Application Data

(60) Division of application No. 12/652,557, filed on Jan. 5, 2010, now Pat. No. 8,357,376, which is a continuation of application No. 11/855,769, filed on Sep. 14, 2007, now abandoned.

(60) Provisional application No. 60/951,813, filed on Jul. 25, 2007, provisional application No. 60/917,008, filed on May 9, 2007, provisional application No. 60/871,721, filed on Dec. 22, 2006, provisional application No. 60/845,121, filed on Sep. 15, 2006.

(51) Int. Cl.
*A61K 39/145* (2006.01)
*A01N 65/00* (2009.01)
*A61K 39/00* (2006.01)
*C12N 5/02* (2006.01)
*C07K 17/00* (2006.01)
*C12N 7/00* (2006.01)

(52) U.S. Cl.
CPC ........ *C12N 7/00* (2013.01); *C12N 2760/16251* (2013.01); *C12N 2760/16252* (2013.01); *C12N 2760/16152* (2013.01); *C12N 2760/16151* (2013.01)
USPC ... 424/93.7; 424/209.1; 424/93.6; 424/184.1; 435/325; 530/413

(58) Field of Classification Search
CPC ............. A61K 39/145; A61K 2039/5254; A61K 2300/00; C12N 2760/16134; C12N 2760/16234; C12N 2760/16122; C12N 2760/16151; C12N 2760/16222; C12N 2760/16251; C12N 15/85; C12N 15/86; C12N 2760/16143; C12N 2760/16243; C12N 2760/16261; C12N 2500/99; C12N 2760/16051; C12N 2760/16164; C12N 2760/16111; C12N 2760/16211; C12N 2760/16221; C12N 2760/16351; C12N 2830/85; C12N 5/00; C12N 5/0043; C12N 5/005; C12N 5/0075; C07K 14/11; C12Q 1/70; G01N 2333/11
See application file for complete search history.

(56) References Cited

U.S. PATENT DOCUMENTS

| | | | |
|---|---|---|---|
| 5,824,536 A | 10/1998 | Webster et al. | |
| 5,948,410 A | 9/1999 | Van Scharrenburg et al. | |
| 6,194,191 B1 | 2/2001 | Zhang et al. | |
| 6,245,549 B1 | 6/2001 | Ewasyshyn et al. | |
| 6,455,298 B1 | 9/2002 | Groner et al. | |
| 6,656,720 B2 | 12/2003 | Groner | |
| 6,726,907 B1 | 4/2004 | Zhang et al. | |
| 6,825,036 B2 | 11/2004 | Makizumi et al. | |
| 6,951,752 B2 | 10/2005 | Reiter et al. | |
| 7,553,665 B2 | 6/2009 | Aloni et al. | |
| 7,670,837 B2 | 3/2010 | Schwartz | |
| 8,119,388 B2 | 2/2012 | Schwartz | |
| 8,202,726 B2 * | 6/2012 | Liu et al. | 435/403 |
| 8,357,376 B2 | 1/2013 | Liu | |
| 2004/0077086 A1 | 4/2004 | Reiter et al. | |
| 2004/0106184 A1 | 6/2004 | Senesac | |
| 2004/0171152 A1 | 9/2004 | Price | |
| 2005/0186224 A1 | 8/2005 | Buchholz et al. | |
| 2006/0002862 A1 | 1/2006 | Truong-Le et al. | |
| 2006/0134138 A1 | 6/2006 | Kawaoka et al. | |
| 2006/0171955 A1 | 8/2006 | Alonso-Caplan et al. | |

(Continued)

FOREIGN PATENT DOCUMENTS

| | | |
|---|---|---|
| AU | 2005322352 | 12/2011 |
| CN | 1326939 | 12/2011 |
| EP | 0870508 | 10/1998 |
| EP | 0891420 | 2/2005 |
| EP | 1739167 | 1/2007 |

(Continued)

OTHER PUBLICATIONS

Extended European Search Report dated: Jun. 11, 2013 in European Application No. EP13163566 filed: Sep. 24, 2006.

(Continued)

*Primary Examiner* — Benjamin P Blumel
(74) *Attorney, Agent, or Firm* — Grant IP, Inc.

(57) ABSTRACT

The present invention relates to novel MDCK cells which can be to grow viruses, e.g., influenza viruses, in cell culture to higher titer than previously possible. The MDCK cells can be adapted to serum-free culture medium. The present invention further relates to cell culture compositions comprising the MDCK cells and cultivation methods for growing the MDCK cells. The present invention further relates to methods for producing influenza viruses in cell culture using the MDCK cells of the invention.

24 Claims, 18 Drawing Sheets

(56) References Cited

U.S. PATENT DOCUMENTS

Figure 1:
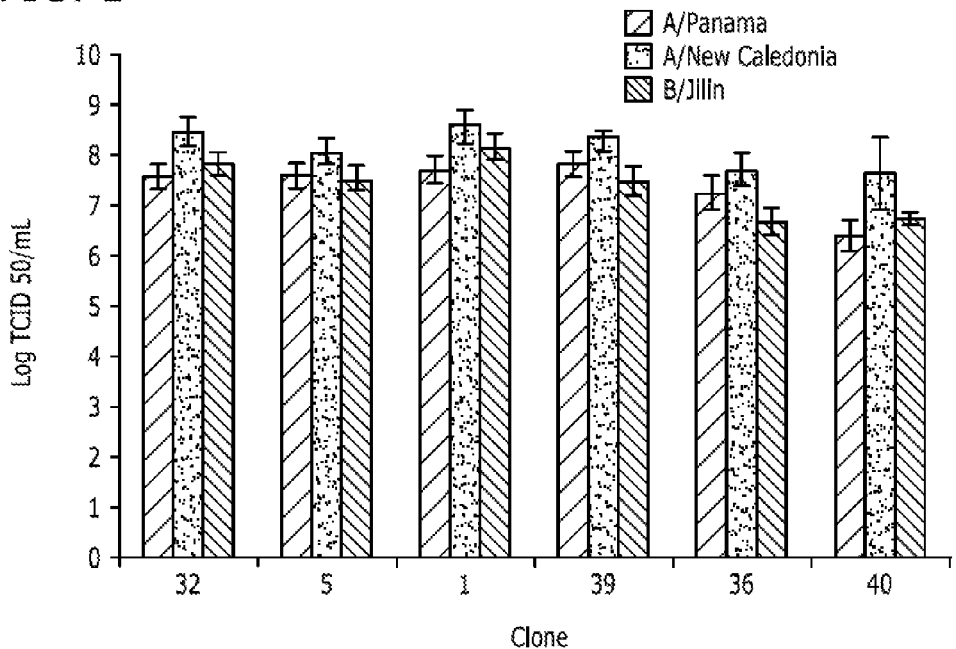

| | | |
|---|---|---|
| 2006/0188977 A1 | 8/2006 | Schwartz |
| 2007/0202527 A1 | 8/2007 | Wallace et al. |
| 2007/0249019 A1 | 10/2007 | Kang et al. |
| 2008/0031895 A1 | 2/2008 | Galarza et al. |
| 2008/0286850 A1 | 11/2008 | Liu |
| 2010/0112000 A1 | 5/2010 | Schwartz et al. |
| 2010/0112669 A1 | 5/2010 | Liu |
| 2012/0115206 A1 | 5/2012 | Schwartz et al. |

FOREIGN PATENT DOCUMENTS

| | | |
|---|---|---|
| EP | 1862537 | 12/2007 |
| JP | 2000-507448 | 6/2000 |
| JP | 2000-517188 | 12/2000 |
| JP | 2005-511051 | 4/2006 |
| SU | 1698288 | 12/1991 |
| WO | WO 98/22588 | 5/1998 |
| WO | WO 01/64846 | 9/2001 |
| WO | WO 02/12455 | 2/2002 |
| WO | WO 2004/110484 | 12/2004 |
| WO | WO 2005/026333 | 3/2005 |
| WO | WO 2005/113758 | 12/2005 |
| WO | WO 2006/071563 | 12/2006 |
| WO | WO 2008/105931 | 9/2008 |
| WO | WO 2008/125361 | 10/2008 |
| WO | WO 2010/036760 | 4/2010 |
| WO | WO 2010/036774 | 4/2010 |

OTHER PUBLICATIONS

Office Action mailed on: Jun. 21, 2013 in U.S. Appl. No: 13/355,252 filed on: Jan. 20, 2012 and published as: US 2012/0115206 on May 10, 2012.

MOCK (NBI-2) (ATCC® CCI-34TM). ATCC®, retrieved on Jun. 5, 2013. Retrieved from the Internet <URL:atcc.org/Products/ All/ CCL-34. aspx#85786B46AA23451B94BC5045200673 F7>.

DMEM (ATCC® 30-2002™), ATCC®, retrieved on Jun. 5, 2013. Retrieved from the Internet <URL: atcc.org/products/all/30-2002.aspx>.

"Guidance for Industry: Characterization and Qualification of Cell Substrates and Other Biological Starting Materials used in the Production of Viral Vaccines for the Prevention and Treatment of Infectious Diseases." (2006) 25: 697-723.

Aggarwal, Kunal, AB Stract and Presentation—"Rational strategies for improving cell culture based production of Cold-Adapted Influenza Vaccine (CAIV) strains of FluMist®.", Cell Culture Engineering XI, Queensland, Australia. Apr. 13-18, 2008.

Aggarwal, Kunal, Abstract and Presentation—"Assessment of platform vaccine process development and improvement of vaccine productivity through bioprocess optimization", 236th American Chemical Society National Meeting. Philadelphia, P A. Aug. 17-21, 2008.

Aggarwal, Kunal, Poster—"Development of a cell culture production platform for Cold-Adapted Live Attenuated Influenza Vaccine (LAIV) strains: role of multiplicity of infection in improving bioreactor productivity", Biochemical Engineering XVI. Burlington, Vermont, Jul. 5-9, 2009.

American Type Culture Collection Cell Repository, et al. "Registry of Animal Cell Lines: Certified by the Cell Culture Collection Committee: MDCK." (1964) : 1-2.

Arthur, J. M. "The MDCK Cell Line is made Up of Populations of Cells with Diverse Resistive and Transport Properties." Tissue Cell (2000) 32: 446-50.

ATCC cell line database search accessed on Mar. 23, 2009 <http://www.atcc.org/ATCCAdvancedCatalogSearch/AllCollectionSearch/tabid/454/Default.aspx>.

Bashir, N., et al. "Phospholipids Regulate Growth and Function of MDCK Cells in Hormonally Defined Serum Free Medium." In Vitro Cell.Dev.Biol. (1992) 28A: 663-8.

Boerner, P., et al. "Characterization of Chemically and Virally Transformed Variants of Madin-Darby Canine Kidney (MDCK) Epithelial Cells." J.Cell.Physiol. (1985) 122: 299-307.

Boerner, P., et al. "Nutrient Transport and Growth Regulation in Kidney Epithelial Cells (MDCK) Cultured in a Defined Medium." Cold Spring Harbor Conferences on Cell Proliferation., 1982 555-565 Cold Spring Harbor Laboratory.

Brands, R., et al. "Influvac: A Safe Madin Darby Canine Kidney (MDCK) Cell Culture-Based Influenza Vaccine." Dev.Bio1.Stand. (1999) 98: 93,100; discussion 111.

Burteau et al., "Fortification of a protein-free cell culture medium with plant peptones improves cultivation and productivity of an interferon-gamma-producing CHO cell line," in Vitro Cell. Dev. Biol., vol. 39, No. 7, 291-296(2003).

Chiton Behring Gmbh. "Use of MDCK Cells for Manufacture of Inactivated Influenza Virus Vaccines. (Briefing Document)." FDA—Vaccines and Related Biological Products Advisory Committee. Bethesda, MD, Nov. 16, 2005. pp. 1-14 (as downloaded Dec. 12, 2008 from http://www.fda.gov/ohrms/dockets/ac/05/briefing/5-4188BI I8.pdf).

Coelingh, K., Presentation: "Next Generation Flu Vaccines: Taking a Crack at Vaccine Production using Cell Culture Technology." The Vaccine Discovery and Commercialization Meeting. Philadelphia, PA, USA, May 23, 2006. pp. 1-10.

Cortes, Bernadette, Abstract and Poster—"Modeling based scale-up strategy for bioreactor cell culture processes", Cell Culture Engineering XI, Queensland, Australia. Apr. 13-18, 2008.

Cortes, Bernadette, Poster—"The Utilization of Antifoam C Emulsion in Adherent Cell Culture Bioreactor Process: implications for process scale-up", Presented at BioProcess International Conference, Raleigh, NC. Oct. 12-16, 2009.

Dobbelaer, R. "ICH Guidelines and PhEur Monographs on Derivation and Characterization of Cell Substrates used for Production of biotechnological/biological Products. International Conference on Harmonization." Dev.Biol.Stand. (1999) 98: 159-65.

Dumitrescu, M. R., et al. "A Three Years Experience in using MDCK Cell Line for Influenza Virus Isolation (1979-1981)." Arch.Roum. Pathol.Exp.Microbiol. (1981) 40: 313-316.

Furminger,I. "Vaccine Production." Textbook of Influenza., 1998. Chapter 24: 324-32. Blackwell Oxford, UK.

Gaush, C. R., et al. "Characterization of an Established Line of Canine Kidney Cells (MDCK)." Proc.Soc.Exp.Biol.Med. (1966) 122: 931-5.

Genzel, Y., et al. "Metabolism of MDCK Cells during Cell Growth and Influenza Virus Production in Large-Scale Microcarrier Culture," Vaccine (2004) 22: 2202-8.

George, M., and et al., Abstract and Poster Presentation: "Development of a Fully Disposable Platform Process for Cell Culture Production of Cold-Adapted Live Attenuated Influenza Vaccine (CAIV) Strains of FluMist(R)." WillBio-Single-use BioProcessing Components and Systems. Concord, CA, USA, Jul. 16-18, 2007. pp. 1-5.

George, Meena Abstract and Poster—"Development of a cell culture production platform for Cold-Adapted live attenuated Influenza Vaccine (CAIV) strains of FluMist®: accelerated development of a fully disposable Phase I clinical manufacturing process", Vaccine Technology II. Albufeira, Portugal. Jun. 1-6, 2008.

George, Meena, Abstract and Poster—"Improving Vaccine Productivity through Medium Fortification and Process Intensification", Biopharmaceutical Manufacturing and Development Summit. San Francisco. Dec. 14-15, 2009.

George, Meena., et al.: "Production of cell culture (MDCK) derived live attenuated influenza vaccine (LAIV) in a fully disposable platform process.", Biotechnology and Bioengineering Aug. 15, 2010 LNKD—PUBMED:20589670, vol. 106, No. 6, Aug. 15, 2010 , pp. 906-917, XP002622299, ISSN: 1097-0290.

Ghendon et al., "Further Development (MDCK of Live Cold-Adapted Influenza Cultivation of Vaccine Strains in Production Fermenters" VoprVirusol (2005) 50: 4-9.

Ghendon, et al. "Development of Cell Culture (MDCK) Live Cold-Adapted (CA) Attenuated Influenza Vaccine." Vaccine (2005) 23: 4678-84.

GIBCO BRL, A Guide to Serum-Free Cell Culture, on line catalog, published on 2003, Please see catalog of VP-SFM+ 11681-020.

Gritliths, E. "WHO Requirements for the use of Animal Cells as in Vitro Substrates for the Production of Biologicals: Application to Influenza Vaccine Production." Dev.Biol.Stand. (1999) 98: 153-7.

(56) References Cited

OTHER PUBLICATIONS

Halperin, S. A., et al., "Safety and Immunogenicity of a Trivalent, Inactivated, Mammalian Cell Culture-Derived Influenza Vaccine in Healthy Adults, Seniors, and Children." (2002) 20: 1240-7.
Hsu, S., "Affinity Purification of a Live Attenuated Influenza Virus from MDCK Cell Culture," presentation at: 4th Vaccine & ISV Annual Global Congress Oct. 3-5, 2010, Vienna, Austria.
Hsu, Simon, Presentation—"Challenges and Opportunities of Using Cell Culture for the Production of Live, Attenuated Influenza Vaccines (LAIV)", World Vaccine Congress. Lyon, France, Oct. 5-8, 2009.
Hsu,S. "Purification Development for a Live Attenuated Influenza Virus from MDCK Cell Culture" presentation at: The Immunotherapeutics and Vaccine Summit Aug. 17-19, 2010, Cambridge, MA.
Hussain, Althaf I., Poster—"Evaluation of High Yielding MDCK Clone for Commercial Production of Cold-Adapted (ca) Live Attenuated Influenza Virus Vaccines—Host Cell Susceptibility and Influenza Virns Replication in Permissive and Semi-Permissive Cells", New cells for new vaccines III. Wilmington, Delaware. Sep. 28-Oct. 1, 2008.
Hussain, Althaf, "Comparison of Egg and High Yielding MDCK Cell-derived Live Attenuated Influenza Virns for Commercial Production of Trivalent Influenza Vaccine: In-vitro Cell Susceptibility and Influenza Virus Replication kinetics in Permissive and Semi-Permissive Cells Vaccine", Vaccine (2010) 28:13848-13855.
Johnson, J. B., et al. "Tumorgenicity of Continuous Monkey Cell Lines in in Vivo and in Vitro Systems." Dev.Biol.Stand. (1981) 50: 27-35.
Kalbfuss, B., et al. "Harvesting and Concentration of Human Influenza A Virus Produced in Serum-Free Mammalian Cell Culture for the Production of Vaccines." Biotechnol.Bioeng. (2007) 97: 73-85.
Kemble, G. Seminar: "Development of LAIV Production in Cell Culture." Meeting with the World Health Organization. Geneva, Switzerland, Jun. 12, 2007, pp. I-5.
Kessler, N., et al. "Suitability of MDCK Cells Grown in a Serum-Free Medium for Influenza Virus Production." Dev.Biol. Stand. (1999) 98: 13,21; discussion 73-4.
Leighton, J., et al. "A Cell Line Derived from Normal Dog Kidney (MDCK) Exhibiting Qualities of Papillary Adenocarcinoma and of Renal Tubular Epithelium." Cancer (1970) 26: 1 022-8.
Leighton, J., et al. "Clinical and Experimental Tumors of the Kidney in Tissue Culture and in the Chick Embryo." Eur.J.Cancer (1972) 8: 281-5.
Leighton, J., et al., "Secretory Activity and Oncogenicity of a Cell Line (MDCK) Derived from Canine Kidney." Science (1969) 163: 472-3.
Lewis, A. M.,Jr, et al. "A Defined-Risks Approach to the Regulatory Assessment of the use of Neoplastic Cells as Substrates for Viral Vaccine Manufacture." Dev.Biol.{Basen (2001) 106: 513-35.
Liu et al., Abstract and Presentation: "Development of a Process for Cell Culture Production of a Cold-Adapted Live Attenuated Influenza Vaccine (LAIV)." WillBio Meeting—BioProcess Technology. Amsterdam, Netherlands, Apr. 2-4, 2007. pp. 1-13.
Liu et al., Abstract and Presentation: "Selection and Characterization of a High Producing Host Cell Line for Influenza Vaccine Production." WillBio Meeting—Cell Engineering and Banking. Washington, DC, USA, Dec. 4-6, 2006. pp. 1-9.
Liu et al., "Developing highly productive bioprocesses to prepare for pandemic outbreaks," presentation at: IVTW (2010) International Vaccine Technology Workshop, Sep. 17-18, 2010, Hyderabad, India.
Liu et al., "Developing highly productive bioprocesses to prepare for pandemic outbreaks," published abstract from: IVTW (2010) International Vaccine Technology Workshop, Sep. 17-18, 2010, Hyderabad, India.
Liu et al., "Development of a highly productive cell culture-based influenza vaccine," presentation at: WCV (2011) BIT Life Sciences World Congress of Vaccine—3rd Annual Beijing China, Mar. 23, 2011.

Liu et al., "Development of a highly productive cell culture-based influenza vaccine," published abstract from: WCV (2011) BIT Life Sciences World Congress of Vaccine—3rd Annual Beijing China, Mar. 23, 2011.
Liu, Jonathan, "Cloning and assessment of tumorigenicity and oncogenicity of a Madin-Darby canine kidney (MDCK) cell line for influenza vaccine production", Vaccine (2010) 28:1285-1293.
Liu, Jonathan, "MDCK cells for manufacture of live attenuated Influenza virus vaccines", World Vaccine Congress. Washington DC, Apr. 20-23 2009.
Liu, Jonathan, "Use of MDCK cells for production of live attenuated influenza vaccine", Vaccine (2009) 27(46):6460-3.
Liu, Jonathan, Abstract and Presentation—"Cell culture-based vaccine: an alternative to egg derived influenza vaccine and its business and operational values", Session 21 of World Congress of Vaccine. Guangzhou, China. Dec. 1-5, 2008.
Liu, Jonathan, Abstract and Presentation—"Challenges and solutions for the next generation of vaccines: Development of cell culture-based live attenuated influenza vaccine", Vaccine Technology II. Albufeira, Portugal. Jun. 1-6, 2008.
Liu, Jonathan, Abstract and Presentation—"Development of a Process for Cell Culture Production of a Cold-Adapted Live Attenuated Influenza Vaccine (LAIV)", 4th Annual Meeting on BioProcess Technology—Europe. Amsterdam, Netherland. Apr. 2-4, 2007.
Liu, Jonathan, Abstract and Presentation—"Improvement of vaccine productivity with reduced manufacturing process development time", Session 59 World Congress of Vaccine. Guangzhou, China. Dec. 1-5, 2008.
Liu, Jonathan, Abstract and Presentation—"Selection and Characterization of a high producing host cell line for Influenza vaccine production", The Williamsburg BioProcessing Foundation Cell Engineering and Banking, Washington, DC. Dec. 4-6, 2006.
Liu, Jonathan, Abstract and Presentation—Transitioning From Eggs to Cell Culture Production of FluMist®, a Live Attenuated Influenza Vaccine (LAIV), and Modeling Seasonal and Pandemic Vaccine Production, BioProcess Technology—Singapore. Singapore, Jul. 30-Aug. 1, 2007.
Liu, Jonathan, Presentation—"Overcome the Scale-up Hurdles and Produce Cell Culture Based Vaccine at Large Scale", Vaccines Europe, Brussels, Belgium, Nov. 17-18, 2009.
Liu, Yi, Abstract and Presentation—"Development of an Economic Production Platform for Live Attenuated Influenza Vaccines", The Immunotherapeutics and Vaccine Summit: Production and Manufacturing of Vaccines. Providence, Rhode Island. Aug. 17-18, 2009.
Lonardo et al.: 'Rapid methods for identification of poliovirus isolates and determination of polio neutralizing antibody titers in human sera..' J Virol Methods. vol. 101, No. 1-2, 2002, pp. 189-196.
Mabrouk, T., et al. "Influenza Vaccine Technologies and the use of the Cell-Culture Process (Cell-Culture Influenza Vaccine)." Dev.Biol. (Basel) (2002) 110: 125-34.
Madin, S. H., et al. "Established Kidney Cell Lines of Normal Adult Bovine and Ovine Origin." Proc.Soc.Exn.Biol.Med. (1958) 98: 574-6.
Mani, S., Abstract and Presentation: "Characterization of a Madin Darby Canine Kidney (MDCK) Cell Bank used in the Production of a Live Attenuated Influenza Vaccine (LAIV)." WillBio Meeting—Cell Engineering and Banking. Philadelphia, PA, USA, Dec. 3-5, 2007. pp. 1-8.
Maranga et al., Abstract and Poster: "Development of a Platform Process for Cell Culture Production of Cold-Adapted Live Attenuated Influenza (CAJV) Strains of FluMist(R)." 20th Meeting of the European Society for Animal Cell Technology (ESACT). Dresden, Germany, Jun. 17-20, 2007. pp. 1-6.
Maranga et al., Abstract and Presentation: "Development of a Platform Process for Cell Culture Production of Cold-Adapted Live Attenuated Influenza Vaccine." Biochemical Engineering XV. Quebec City, Canada, Jul. 15-19, 2007. pp. 1-7.
Maranga, Luis, Abstract—"Development of a Platform Process for Cell Culture Production of a Cold-Adapted Live Attenuated Influenza Vaccine (LAIV)", Presentation—"Development of a Platform Process for Cell Culture Production of Cold-adapted live Attenuated Influenza Vaccine (CAIV) strains of FluMist®". Biochemical Engineering XV. Quebec City, Canada. Jul. 15-19, 2007.

(56) References Cited

OTHER PUBLICATIONS

Maranga, Luis, Abstract and Poster—"Development of a Platform Process for Cell Culture Production of Cold-adapted live Attenuated Influenza Vaccine (CAIV) strains of FluMist®". 20th Meeting of the European Society for Animal Cell Technology. Dresden, Germany. Jun. 17-20, 2007.
Medema et al. "Safety Assessment of Mad in Darby Canine Kidney Cells as Vaccine Substrate." Dev.Biol.(Basel) (2006) 123: 243,50; discussion 265-270.
MedImmune, Briefing Document—"Use of Madin Darby Canine Kidney Cells for the Manufacture of Live, Attenuated Influenza Vaccines", FDA—Vaccines and Related Biological Products Advisory Committee. Silver Spring, MD, Sep. 25, 2008. pp. 1-51.
MedImmune, Presentation—"Live, Attenuated Influenza Vaccine Manufactured in MDCK Cells (VRBPAC Presentation)." FDA—Vaccines and Related Biological Products Advisory Committee. Silver Spring, MD, Sep. 25, 2008. pp. 1-29.
MedImmune. "Use of MDCK Cells for Manufacture of Live, Attenuated Influenza Vaccines (VRBPAC Background Summary)." FDA—Vaccines and Related Biological Products Advisory Committee. Silver Spring, MD, Sep. 25, 2008. pp. 1-9.
Merten et al. "Production of Influenza Virus in Cell Cultures for Vaccine Preparation." Adv.Exn.Med.Bioi. (1996) 397: 141-51.
Merten et al. "Production of Influenza Virus in Serum-Free Mammalian Cell Cultures." Dev.Biol.Stand. (1999) 98: 23,37; discussion 73-4.
Nakazato, Y., et al. "Characterization of Subclones of Madin-Darby Canine Kidney Renal Epithelial Cell Line." Biochim.Bioohvs.Acta (1989) 1014: 57-65.
Pakes, S. P., et al. "Chromosome Analysis of 2 Canine Tumor Cell Lines." Am.J.Vet.Res. (1965) 26: 837-843.
Palache, A. M., et al. "immunogenicity and Reactogenicity of Influenza Subunit Vaccines Produced in MDCK Cells or Fertilized Chicken Eggs." The Journal of infectious diseases 176 Suppl 1 (1997): S20-3.
Palker, T., et al. "Protective Efficacy of Intranasal Cold-Adapted Influenza A/New Caledonia/20/99 (H1N1) Vaccines Comprised of Egg- or Cell Culture-Derived Reassortants." Virus Res. (2004) 105: 183-194.
Percheson et al. "A Phase I, Randomized Controlled Clinical Trial to Study the Reactogenicity and Immunogenicity of a New Split Influenza Vaccine Derived from a Non-Tumorigenic Cell Line." Dev.Biol.Stand. (1999) 98: 127-132; discussion 133-134.
Radaeva, I. F., et al. "Development and Certification of Libraries of the MDCK Continuous Cell Line for Production of Influenza Vaccine." Vopr.Virusol (2005) 50:43-46 Abstract with English language Translation.
Reh et al., Structural Basis for Stable DNA Complex Formation by the Caspase-activated DNase, 2005, The Journal of Biological Chemistry, vol. 280, No. 50, pp. 41707-41715.
Rindler, M. J., et al. "Retention of Differentiated Properties in an Established Dog Kidney Epithelial Cell Line (MDCK)." J.Cell Biol. (1979) 81: 635-48.
Saier et al. "Studies on Growth Regulation and the Mechanism of Transformation of the Kidney Epithelial Cell Line, MDCK: Importance of Transport Function to Growth." Prog.Clin.Biol.Res. (1982) 91: 569-97.
Saier, M. H.,Jr. "Growth and Differentiated Properties of a Kidney Epithelial Cell Line (MDCK)." Am.J.Physiol. (1981) 240: C106-9.
Schwartz, R., Abstract and Presentation: "Transitioning from Eggs to Cell Culture Production FluMist(R), a Live Attenuated Influeza Vaccine (LAIV), and Modeling Seasonal and Pandemic Vaccine Production." WillBio Meeting—BioProcess Technology. Singapore, Jul. 30-Aug. I, 2007. pp. I-14.
Schwartz, Richard, Presentation—"Case Study: Establishing a Benchmark for Economic Vaccine Scale-up Strategies", European BioPharm Scale-Up Congress. Geneva, Switzerland. Sep. 17-19, 2008.
Schwartz, Richard, Presentation—"Developing a Cell Culture Based Influenza Vaccine Process", AICHE 46th Biotechnology Symposium South San Francisco, Apr. 29, 2008.
Solvay. "Madin Darby Canine Kidney Continuous Cell Line (Briefing Document)." FDA—Vaccines and Related Biological Products Advisory Committee. Bethesda, MD, Nov. 16, 2005. pp. 1-21 (as downloaded Dec. 12, 2008 from http://www.fda.gov/ohrms/dockets/ac/05/briefing/5-4188B1__19a.pdf).
Stiles, C. D., et al. "Growth Control of Heterologous Tissue Culture Cells in the Congenitally Athymic Nude Mouse." Cancer Res. (1976) 36: 1353-60.
Stiles, C. D., et al. "Relationship of Cell Growth Behavior in Vitro to Tumorigenicity in Athymic Nude Mice." Cancer Res. (1976) 36: 3300-5.
Subramanian et al., Abstract and Poster: "Developing a Cell Culture Process for Production of Live Attenuated Influenza Virus Vaccine in Madin Darby Canine Kidney Cells." WillBio Meeting—Viral Vectors and Vaccines. Amsterdam, Netherlands, May 25-27, 2005. pp. 1-6.
Subramanian et al., Presentation: "Developing a Cell Culture Process for Production of a Live Attenuated Influenza Virus Vaccine in Madin Darby Canine Kidney Cells." WillBio Meeting—Viral Vectors and Vaccines. Austin, Texas, USA, Nov. 14-16, 2005. pp. 1-5.
Taub, M. et al. "Alterations in Growth Requirements of Kidney Epithelial Cells in Defined Medium Associated with Malignant Transformation." J. Sunramol. Struct. Cell.Biochem. (1981) 15: 63-72.
Taub, M. et al. "An Established but Differentiated Kidney Epithelial Cell Line (MDCK)." Methods Enzymol. (1979) 58: 552-60.
Taub, M. et al. "Growth of Functional Primary Cultures of Kidney Epithelial Cells in Defined Medium." J.Cell.Physiol. (1980) 105: 369-78.
Taub, M., et al. "Growth of Madin-Darby Canine Kidney Epithelial Cell (MDCK) Line in Hormone-Supplemented, Serum-Free Medium." PNAS U.S.A. (1979) 76: 3338-3342.
Taub, N., et al. "The Development of Serum-Free Hormone-Supplemented Media for Primary Kidney Cultures and their use in Examining Renal Functions." Ann.N.Y.Acad.Sci. (1981) 372: 406-21.
Tree, et al., Comparison of large-scale mammalian cell culture system with egg culture for production of influenza virus A vaccine strains, Vaccine, May 2001, 19, 3444-3450.
Voeten, et al. "Characterization of High-Growth Reassortant Influenza A Viruses Generated in MDCK Cells Cultured in Serum-Free Medium." Vaccine (1999) 17: 1942-50.
Voeten, J. T., et al. "Generation and Characterization of Reassortant Influenza A Viruses Propagated in Serum-Free Cultured MDCK-SF1 Cells." Dev.Biol.Stand. (1999) 98: 77,87; discussion 89-90.
Youil, R., et al. "Comparative Study of Influenza Virus Replication in Vero and MDCK Cell Lines." J. Virol.Methods (2004) 120: 23-31.
Zhang et al., "Optimization of Downstream Production for Live Attenuated Influenza Vaccine to Improve Manufacturing Efficiency and Final Bulk Quality," poster presented at: BPI (2010) BioProcess International Conference & Exhibition Sep. 20-24, 2010.
Zhang et al., "Optimization of Downstream Production for Live Attenuated Influenza Vaccine to Improve Manufacturing Efficiency and Final Bulk Quality," published abstract from: BPI (2010) BioProcess International Conference & Exhibition Sep. 20-24, 2010.
Extended European Search Report dated Aug. 25, 2011 in European Application No. EP11004971 filed Dec. 16, 2011.
Supplementary European Search Report dated Feb. 24, 2009 in European Application No. EP05857088 filed on Dec. 16, 2005.
Supplementary European Search Report mailed on: Feb. 28, 2011 in European application No. EP07873787 filed on Sep. 14, 2007.
International Preliminary Report on Patentability. mailed on Jun. 26, 2007 for International Application No. PCT/US2005/45587 filed on: Dec. 16, 2005 and published as: WO 06/071563 on Jul. 6, 2006.
Written Opinion of the International Searching Authority mailed on Jul. 26, 2006 for International Application No. PCT/US2005/45587 filed on: Dec. 16, 2005 and published as: WO 06/071563 on Jul. 6, 2006.
International Search Report and Written Opinion mailed on: Nov. 25, 2009 in International Application No. PCT/US2009/58174 filed on: Sep. 24, 2009 and published as WO 10/036774 on: Apr. 1, 2010.

(56) References Cited

OTHER PUBLICATIONS

International Preliminary Report on Patentability mailed on: Mar. 29, 2011 in International Application No. PCT/US2009/58174 filed on: Sep. 24, 2009 and published as WO 10/036774 on: Apr. 1, 2010.
International Search Report and Written Opinion mailed on Feb. 3, 2010 in International Application No. PCT/US09/058157 filed on Sep. 24, 2007 and published as: WO 10/036760 on Apr. 1, 2010.
International Preliminary Report on Patentability mailed on Mar. 29, 2011 in International Application No. PCT/US09/058157 filed on Sep. 24, 2007 and published as: WO 10/036760 on Apr. 1, 2010.
International Preliminary Report on Patentability mailed on Mar. 17, 2009 in International Application No. PCT/US07/078527 filed on Sep. 14, 2007 and published as WO 08/105931 on Sep. 4, 2008.
International Search Report and Written Opinion mailed on Nov. 26, 2008 in International Application No. PCT/US07/078527 filed on Sep. 14, 2007 and published as WO 08/105931 on Sep. 4, 2008.
Office Action mailed on: Jun. 6, 2011 in U.S. Appl. No. 12/686,926 filed on: Jan. 13, 2010 and published as: US 2010/0112000 on May 6, 2010.
Office Action mailed on: Nov. 29, 2010 in U.S. Appl. No. 12/686,926 filed on: Jan. 13, 2010 and published as: US 2010/0112000 on May 6, 2010.
Office Action mailed on: Sep. 8, 2010 in U.S. Appl. No. 12/686,926 filed on: Jan. 13, 2010 and published as: US 2010/0112000 on May 6, 2010.
Extended European Search Report dated Jul. 27, 2012 in European Application No. EP09816835 filed: Sep. 24, 2009 based on International Application No. PCT/US2009/058174.
Decheme e.V. Press release, "Bioprocessing: Engineering know-how in greater demand than ever," ACHEMA 2006, 28th International Exhibition Congress on Chemical Engineering, Environmental Protection and Biochemistry, Trend Report No. 15:Bioprocessing, pp: 1-6.
Downing et al., "Active respiratory syncytical virus purified by ino-exchange chromatography: characterization of binding and elution requirements," Journal of Virological Methods, vol. 38, No. 2, Aug. 1, 1992, pp. 215-228.
Extended European Search Report dated Jul. 27, 2012 in European Application No. EP09816828 filed: Sep. 24, 2009 based on International Application No. PCT/US2009/058157.
Wolff et al., "Downstream Processing: From Egg to Cell Culture-Derived Influenza Virus Particles," Chemical Engineering & Technology, vol. 31. No. 6, Jun. 1, 2008, pp. 846-857.
Kalbfuss et al., "Purification of cell culture-derived human influenza A virus by size-exclusion and anion-exchange chromatography," vol. 96, Issue 5, pp. 932-944, Apr. 1, 2007.
Office Action mailed on Sep. 26, 2013 in U.S. Appl. No. 13/473,494, filed on May 16, 2012 and published as US 2012-0258136 on Oct. 11, 2012.
Reamer et al., "Purification of Large Quantities of Influenza Virus by Density Gradient Centrifugation" Journal of Virology (1967) 1(6):1207-1216.
Wickramasinghe et al., "Tangential Flow Microfiltration and Ultrafiltration for Human Influenza A Virus Concentration and Purification" Biotechnology and Bioengineering (2005) 92(2):199-208.
Taub et al., "PGE1-independent MDCK cells have elevated intracellular cyclic AMP but retain the growth stimulatory effects of glucagon and epidermal growth factor in serum free medium" J. Cell. Physiol. (1984) 120:19-28.
Office Action mailed on Jan. 28, 2014 in U.S. Appl. No. 13/355,252, filed on Jan. 20, 2012 and published as US 2012-0115206 on May 10, 2012.
Office Action mailed on May 8, 2014 in U.S. Appl. No. 13/473,494, filed May 16, 2012 and published as US 2012-0258136 on Oct. 11, 2012.

* cited by examiner

FIG. 4

| Sub Clone | Media | A/New Caledonia (log 10 FFU/mL) | | | | A/Hiroshima (log 10 FFU/mL) | | | | B/Malaysia (log 10 FFU/mL) | | | | A/Vietnam (log 10 FFU/mL) | | | |
|---|---|---|---|---|---|---|---|---|---|---|---|---|---|---|---|---|---|
| | | 3 DPI | | 4 DPI | | 3 DPI | | 4 DPI | | 3 DPI | | 4 DPI | | 3 DPI | | 4 DPI | |
| | | Flask #1 | Flask #2 | Flask #1 | Flask #2 | Flask #1 | Flask #2 | Flask #1 | Flask #2 | Flask #1 | Flask #2 | Flask #1 | Flask #2 | Flask #1 | Flask #2 | Flask #1 | Flask #2 |
| 1-A | Opti-Pro | 8.2±0.06 | 8.2±0.06 | 8.2±0.06 | 8.4±0.06 | 8.2±0.15 | 8.1±0.12 | 8.2±0.06 | 8.2±0.06 | 8.1±0.06 | 8.1±0.06 | 8.1±0.06 | 8.1±0.00 | 8.3±0.00 | 8.3±0.00 | 8.4±0.06 | 8.5±0.00 |
| 1-B | | 8.3±0.06 | 8.4±0.06 | 8.4±0.06 | 8.4±0.10 | 8.3±0.10 | 8.3±0.12 | 8.2±0.06 | 8.1±0.12 | 8.1±0.06 | 7.9±0.06 | 7.8±0.06 | 7.8±0.12 | 8.3±0.00 | 8.3±0.06 | 8.5±0.06 | 8.4±0.06 |
| 1-D | | 8.3±0.00 | 8.3±0.06 | 8.3±0.10 | 8.3±0.06 | 8.4±0.06 | 8.2±0.21 | 8.1±0.06 | 8.1±0.10 | 8.0±0.06 | 8.0±0.00 | 7.7±0.06 | 7.7±0.06 | 8.3±0.06 | 8.4±0.06 | 8.5±0.06 | 8.5±0.00 |
| 1-C | | 8.4±0.10 | 8.5±0.06 | 8.4±0.00 | 8.4±0.10 | 8.2±0.06 | 8.2±0.06 | 8.2±0.00 | 8.1±0.06 | 7.9±0.06 | 7.9±0.06 | 7.6±0.06 | 7.7±0.10 | 8.2±0.00 | 8.1±0.06 | 8.4±0.06 | 8.3±0.06 |
| 1-A | MediV-105 | 8.3±0.10 | 8.2±0.06 | 8.3±0.06 | 8.3±0.06 | 8.1±0.07 | 8.1±0.14 | 8.1±0.00 | 8.2±0.12 | 8.0±0.06 | 8.0±0.06 | 7.8±0.06 | 7.8±0.10 | 8.1±0.06 | 8.2±0.06 | 8.3±0.06 | 8.3±0.06 |
| 1-B | | 8.3±0.10 | 8.3±0.06 | 8.0±0.06 | 8.1±0.12 | 7.8±0.10 | 7.9±0.06 | 7.8±0.12 | 8.0±0.12 | 8.1±0.00 | 8.2±0.06 | 7.6±0.06 | 7.7±0.10 | 8.3±0.06 | 8.2±0.00 | 8.4±0.06 | 8.3±0.06 |
| 1-C | | 8.2±0.06 | 8.1±0.00 | 9.2±0.06 | 9.1±0.10 | 8.3±0.06 | 8.3±0.00 | 8.2±0.06 | 8.3±0.06 | 7.9±0.10 | 8.0±0.10 | 8.1±0.06 | 8.0±0.06 | 8.2±0.12 | 8.2±0.10 | 8.3±0.06 | 8.3±0.06 |
| Assay Control | | 9.1±0.06 | 9.1±0.06 | 9.2±0.06 | 9.1±0.10 | | | | | | | | | | | | |

FIG. 5A

```
┌─────────────────────────────────────────────────────────────────────────┐
│ Thaw a vial of ATCC MDCK (CCL34, Lot: 1805449) and seed T-25 flask      │
│ using 10 ml 10% FBS DMEM medium (P55)                                   │
└─────────────────────────────────────────────────────────────────────────┘
                    │ 2 more passage in 10% FBS DMEM
                    ▼ Medium in T-225 flasks
┌─────────────────────────────────────────────────────────────────────────┐
│ Recover MDCK cells by trypsinization, concentrate by centrifugation,    │
│ resuspend cells in 10% FBS DMEM medium with 7.5% DMSO, aliquot 1 ml in  │
│ cryovials (Serum MDCK Pre-Cell Bank, P57)                               │
└─────────────────────────────────────────────────────────────────────────┘
                    │
                    ▼
┌─────────────────────────────────────────────────────────────────────────┐
│ Thaw a vial of Serum MDCK PreMCB and seed T-75 flask using 35 ml 10%    │
│ FBS DMEM medium (P58)                                                   │
└─────────────────────────────────────────────────────────────────────────┘
                    │ 3 more passages in 10% FBS DMEM
                    ▼ Medium in T-225 flasks
┌─────────────────────────────────────────────────────────────────────────┐
│ Recover MDCK cells by trypsinization, concentrate by centrifugation,    │
│ resuspend cell in 10% FBS DMEM medium with 7.5% DMSO, aliquot 1 ml in   │
│ cryovials (Serum MDCK in 10% FBS DMEM, P61)                             │
└─────────────────────────────────────────────────────────────────────────┘
                    │
                    ▼
┌─────────────────────────────────────────────────────────────────────────┐
│ Thaw a vial of Serum MDCK in 10% FBS DMEM and seed T-75 flask using     │
│ 35 ml 10% FBS DMEM medium (P62)                                         │
└─────────────────────────────────────────────────────────────────────────┘
                    │ 5 more passages in 10% FBS DMEM
                    ▼ Medium in either T-75 or T225 flasks
┌─────────────────────────────────────────────────────────────────────────┐
│ Recover MDCK cells by trypsinization, seed cells at 0.5 cell/well/100 uL│
│ in 96-well plates, pick single cell clones, expand and freeze. Total of │
│ 54 clones were frozen. Clone 1 was frozen at P4 after cloning (P71      │
│ total passage)                                                          │
└─────────────────────────────────────────────────────────────────────────┘
                    │
                    ▼
┌─────────────────────────────────────────────────────────────────────────┐
│ Thaw a vial of Serum MDCK clone 1 and seed T-75 flask using 35 ml 10%   │
│ FBS DMEM/F12 medium (P5/P72)                                            │
└─────────────────────────────────────────────────────────────────────────┘
                    │ 8 more passages in 10% FBS DMEM/F12
                    ▼ Medium in either T-75 or T-225 flasks
┌─────────────────────────────────────────────────────────────────────────┐
│ Recover MDCK clone 1 cells by trypsinization, seed cell at 0.5 cell/    │
│ well/100?1 in 96-well plates, pick single cell clones, expand and       │
│ freeze. Total of 63 clones were selected and banked. Sub clone 1-B was  │
│ frozen at P5 after subcloning (P85 total passage)                       │
└─────────────────────────────────────────────────────────────────────────┘
```

FIG. 5B

```
┌─────────────────────────────────────────────────────────────────────────────┐
│ Thaw a vial of Serum MDCK clone 1-B Lot NB894Pg173 and seed T-75 flask      │
│ using 35 ml 10% FBS DMEM/F12 medium (P86)                                   │
└─────────────────────────────────────────────────────────────────────────────┘
                    │ 2 more passage in 10% FBS DMEM/F12
                    │ medium in T75 flasks
                    ▼
┌─────────────────────────────────────────────────────────────────────────────┐
│ Recover MDCK clone 1-B cells by trypsinization, seed cells into a T-75      │
│ flask containing 35 ml MediV-105 serum-free medium @ 5x10⁴ cells per ml     │
│ media (P89 total passage)                                                   │
└─────────────────────────────────────────────────────────────────────────────┘
                    │ 4 more passage MediV-105 serum-free
                    │ medium in T-75 flasks or T-225 flasks
                    ▼
┌─────────────────────────────────────────────────────────────────────────────┐
│ Recover MDCK cells by trypsinization, concentrate by centrifugation,        │
│ resuspend cell in 50% spend medium+50% fresh MediV-105 SFM+7.5% DMSO,       │
│ aliquot 1 ml in cryovials (Serum Free MDCK B-1 accession bank, P93 total    │
│ passage)                                                                    │
└─────────────────────────────────────────────────────────────────────────────┘
```

- Thaw a vial of Serum MDCK clone 1-B Lot NB894Pg173 and seed T-75 flask using 35 ml 10% FBS DMEM/F12 medium (P86)
- 2 more passage in 10% FBS DMEM/F12 medium in T75 flasks
- Recover MDCK clone 1-B cells by trypsinization, seed cells into a T-75 flask containing 35 ml MediV-105 serum-free medium @ $5 \times 10^4$ cells per ml media (P89 total passage)
- 4 more passage MediV-105 serum-free medium in T-75 flasks or T-225 flasks
- Recover MDCK cells by trypsinization, concentrate by centrifugation, resuspend cell in 50% spend medium+50% fresh MediV-105 SFM+7.5% DMSO, aliquot 1 ml in cryovials (Serum Free MDCK B-1 accession bank, P93 total passage)

MDCK CELL LINES SUPPORTING VIRAL GROWTH TO HIGH TITERS AND BIOREACTOR PROCESS USING THE SAME

1. CROSS REFERENCE TO RELATED APPLICATIONS

This application is a divisional of U.S. Ser. No. 12/652,557, filed Jan. 5, 2010, which is a continuation of U.S. Ser. No. 11/855,769, filed Sep. 14, 2007, said application Ser. No. 11/855,769 claims the benefit under 35 U.S.C. §119(e) of the following U.S. Provisional Application Nos. 60/845,121 filed Sep. 15, 2006; 60/871,721 filed Dec. 22, 2006; 60/917,008 filed May 9, 2007; and 60/951,813 filed Jul. 25, 2007. The priority applications are hereby incorporated by reference herein in their entirety for all purposes.

2. STATEMENT AS TO RIGHTS TO INVENTIONS MADE UNDER FEDERALLY SPONSORED RESEARCH AND DEVELOPMENT

One or more inventions described herein were made with Government support under Contract No. HHS0100200600010C awarded by Health and Human Services. Accordingly, the Government may have certain rights in such inventions.

3. FIELD OF THE INVENTION

The present invention relates to novel MDCK cells which can be used to grow viruses, e.g., influenza viruses, particularly cold-adapted, and/or temperature sensitive, and/or attenuated influenza viruses, in cell culture to high titer. The MDCK cells can be adapted to or genetically modified to grow in serum-free culture medium. The present invention further relates to cell culture compositions comprising the MDCK cells, cultivation methods for growing the MDCK cells, and methods for identifying such cells. The present invention further relates to methods for producing influenza viruses in cell culture using the MDCK cells of the invention. In particular the present invention relates to novel bioreactor processes for growing adherent cells (e.g., MDCK cells) which can be used to grow viruses, (e.g., influenza viruses, particularly cold-adapted, and/or temperature sensitive, and/or attenuated influenza viruses), in cell culture to high titer. The bioreactor processes may utilize serum-free culture medium. The present invention further relates to vaccine compositions generated using the bioreactor processes of the invention.

4. BACKGROUND OF THE INVENTION

Vaccination is the most important public health measure for preventing disease caused by annual epidemics of influenza. The effective use of vaccines is dependent on being able to quickly produce large quantities of vaccine material (e.g., virus) from a stable and easy to cultivate source. The rapid development of vaccines and their abundant availability is critical in combating many human and animal diseases. Delays in producing vaccines and shortfalls in their quantity can cause problems in addressing outbreaks of disease. For example, recent studies suggest that there is cause for concern regarding the long lead times required to produce vaccines against pandemic influenza. See, for example, Wood, J. M., 2001, Philos. Trans. R. Soc. Lond. B. Biol. Sci., 356:1953. Accordingly, recent efforts to produce vaccines have focused on growth of viruses for vaccines in cell culture.

Madin Darby Canine Kidney (MDCK) cells have been traditionally used for the titration of influenza viruses (Zambon M., in *Textbook of Influenza*, ed Nicholson, Webster and Hay, ch 22, pg 291-313, Blackwell Science (1998)). These cells were established in 1958 from the kidney of a normal male cocker spaniel. The ATCC list the MDCK (CCL 34) line as having been deposited by S. Madin and N. B. Darby. However, existing MDCK cell lines suffer from several defects, including possible tumorigenicity, the requirement for animal serum in cell culture, and low yields of influenza viruses suitable for use in vaccines. Accordingly, there remains an unmet need for MDCK cell lines, preferably non-tumorigenic MDCK cell lines that can grow such influenza strains to high titer, preferably, in serum free media. These and other unmet needs are provided by the present invention.

5. SUMMARY OF THE INVENTION

The present invention provides MDCK cells which can support the growth of influenza viruses, e.g., cold-adapted, and/or temperature sensitive, and/or attenuated influenza viruses, to high titer. The MDCK cells can grow in either serum containing or serum-free media formulations including animal protein-free (APF) formulations, but preferably grow in serum-free and/or APF media formulations. Accordingly, in a first aspect, the invention provides a Madin-Darby Canine Kidney (MCDK) cell, wherein a cell culture composition comprising a plurality of the MDCK cells supports replication of a cold-adapted, and/or temperature sensitive, and/or attenuated influenza virus to a base 10 logarithm of the median tissue culture infection dose per milliliter ($\log_{10}$ $TCID_{50}$/mL) of at least about 7.0. In some embodiments, the MDCK cells of the invention are adherent. In other embodiments, the MDCK cells of the invention are non-adherent (e.g., capable of growth under non-adherent conditions). In some embodiments, the MDCK cells of the invention are non-tumorigenic. In some embodiments, the MDCK cells of the invention have an epithelial morphology. In some embodiments, the MDCK cells of the invention are adherent and have an epithelial morphology. In some embodiments, the MDCK cells of the invention are adapted or selected to grow under non-adherent conditions. In some embodiments, the MDCK cells of the invention are adherent and non-tumorigenic.

Viruses that can be grown in the MDCK cells of the invention include but are not limited to negative strand RNA viruses, including but not limited to influenza, RSV, parainfluenza viruses 1, 2 and 3, and human metapneumovirus, as well as other viruses, including DNA viruses, retroviruses, positive strand RNA viruses, negative strand RNA viruses, double-stranded RNA viruses, including, but not limited to, papovavirus, vesicular stomatitis virus, vaccinia virus, Coxsackie virus, reovirus, parvovirus, adenovirus, poliomyeltitis virus, measles virus, rabies virus, and herpes virus.

The present invention further provides methods and media formulations useful for the derivation, propagation and maintenance of MDCK cells that can support the growth of influenza viruses, e.g., cold-adapted, and/or temperature sensitive, and/or attenuated influenza viruses, to high titer. The MDCK cells of the invention are particularly useful for the production of vaccine material such as, for example, viruses. Accordingly, in another aspect, the invention provides a cell culture composition comprising MDCK cells and a cell culture medium, wherein the cell culture composition supports replication of a cold-adapted, and/or temperature sensitive, and/or attenuated influenza virus to a $\log_{10}$ $TCID_{50}$/mL of at least about 7.0.

Other aspects of the invention include methods of producing vaccine material (e.g., virus) by culturing any MDCK cell of the invention, in a suitable culture medium under conditions permitting production of vaccine material and, isolating the material from one or more of the cell or the medium in which it is grown. Thus, in some embodiments, the invention provides a method for producing influenza viruses in cell culture, comprising infecting a cell culture composition of the invention with an influenza virus, incubating the cell culture composition under conditions that permit replication of the influenza virus; and isolating influenza viruses from the cell culture composition.

In another aspect, the invention provides immunogenic compositions. For example, in some embodiments, the invention provides immunogenic compositions comprising the vaccine material produced as described above and, optionally, an excipient such as a pharmaceutically acceptable excipient or one or more pharmaceutically acceptable administration component.

Methods of producing immunogenic responses in a subject through administration of an effective amount of one or more above described immunogenic compositions to a subject are also within the current invention. Additionally, methods of prophylactic or therapeutic treatment of a viral infection (e.g., viral influenza) in a subject through administration of one or more above described immunogenic compositions in an amount effective to produce an immunogenic response against the viral infection are also part of the current invention. Subjects for such treatment can include mammals (e.g., humans), avian species (e.g., poultry). Additionally, such methods can also comprise administration of a composition of one or more viruses produced in the MDCK cells of the invention and a pharmaceutically acceptable excipient that is administered to the subject in an amount effect to prophylactically or therapeutically treat the viral infection.

These and other objects and features of the invention will become more fully apparent when the following detailed description is read in conjunction with the accompanying figures appendix.

6. BRIEF DESCRIPTION OF THE FIGURES

FIG. 1 presents a graphical representation of reassortant influenza virus strains comprising HA and NA gene segments from wild type influenza virus strains A/Panama, A/New Calcdonia, or B/Jilin yields in MDCK clones 1, 5, 36, 39, 40, and 55.

Figure 2:
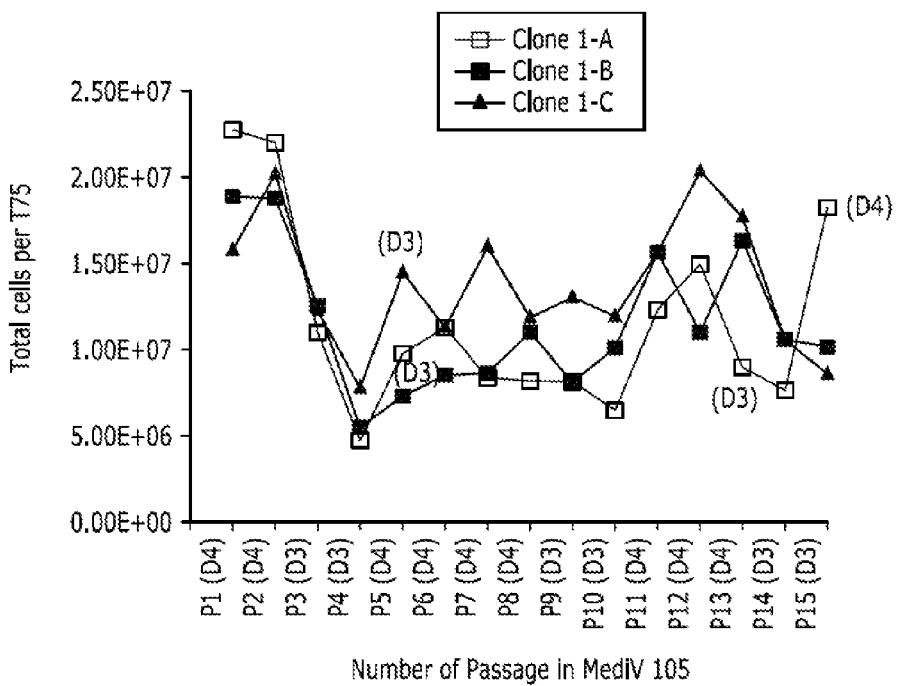

FIG. 2 presents a graphical representation of cell growth of MDCK subclones 1-A, 1-B, and 1-C in MediV 105 serum free medium.

Figure 3:
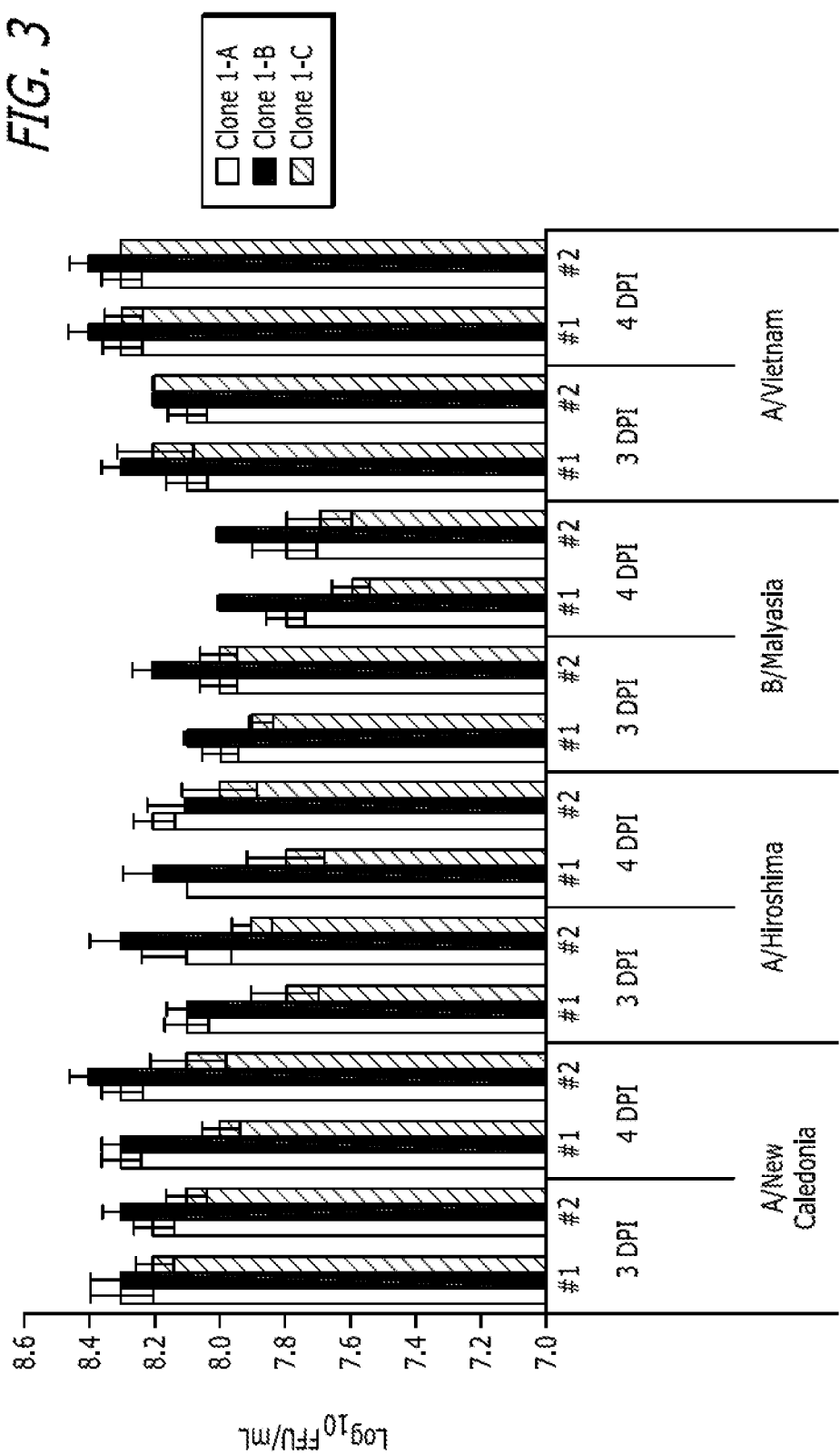

FIG. 3 presents a graphical representation of yields of reassortant influenza virus strains comprising HA and NA gene segments from wild type influenza virus strains A/New Calcdonia/20/99, A/Hiroshima/52/05, B/Malaysia/2506/04, or A/Vietnam/1203/2004 and the remaining gene segments from a cold-adapted, temperature sensitive, attenuated virus in MDCK subclones 1-A, 1-B, and 1-C 3 and 4 days post infection (DPI).

FIG. 4 presents a table showing yields of reassortant influenza virus strains comprising HA and NA gene segments from wild type influenza virus strains A/New Calcdonia/20/99, A/Hiroshima/52/05, B/Malaysia/2506/04, or A/Vietnam/1203/2004 and the remaining gene segments from a cold-adapted, temperature sensitive, attenuated virus in MDCK subclones 1-A, 1-B, 1-C, and 1-D 3 and 4 days post infection (DPI) in OptiPro™ media and in MediV 105.

FIG. 5 presents the flow chart of MDCK Subclone 1-B serum free cell bank preparation. Panel A presents the selection steps performed in serum containing media. Panel B presents the steps for adaptation to serum free media.

Figure 6:
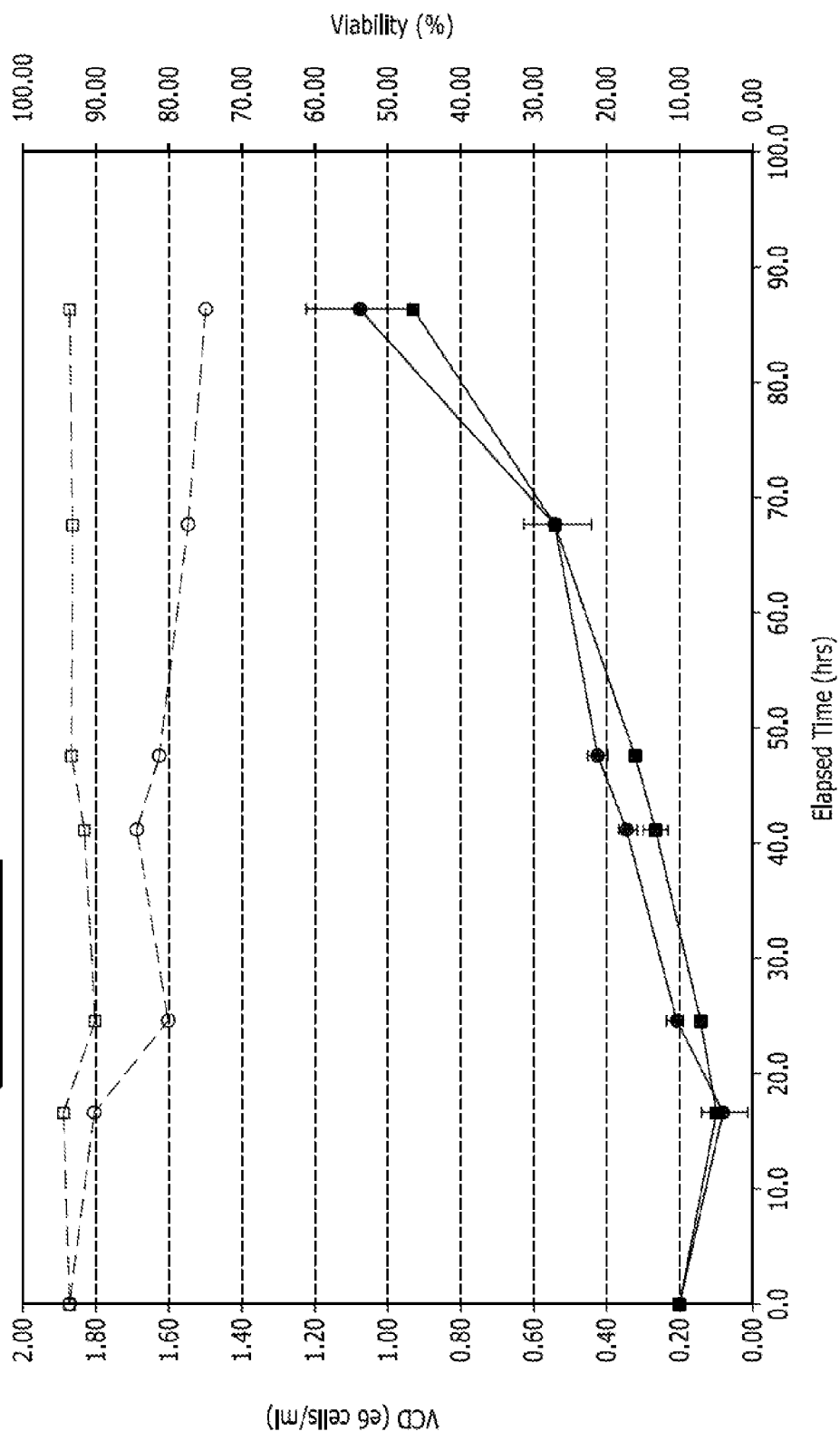

FIG. 6 presents the growth of subclone 1-A in MediV 105 and M18M media.

Figure 7:
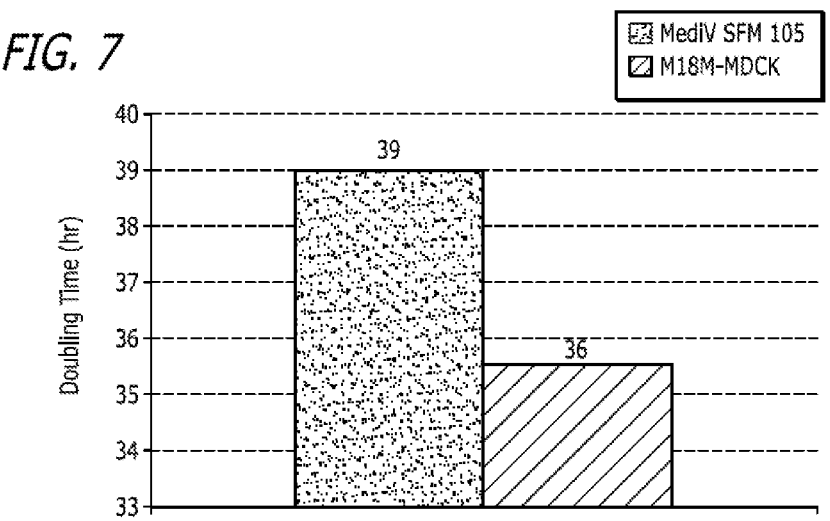

FIG. 7 presents the doubling time of subclone 1-A in MediV 105 and M18M media.

Figure 8:
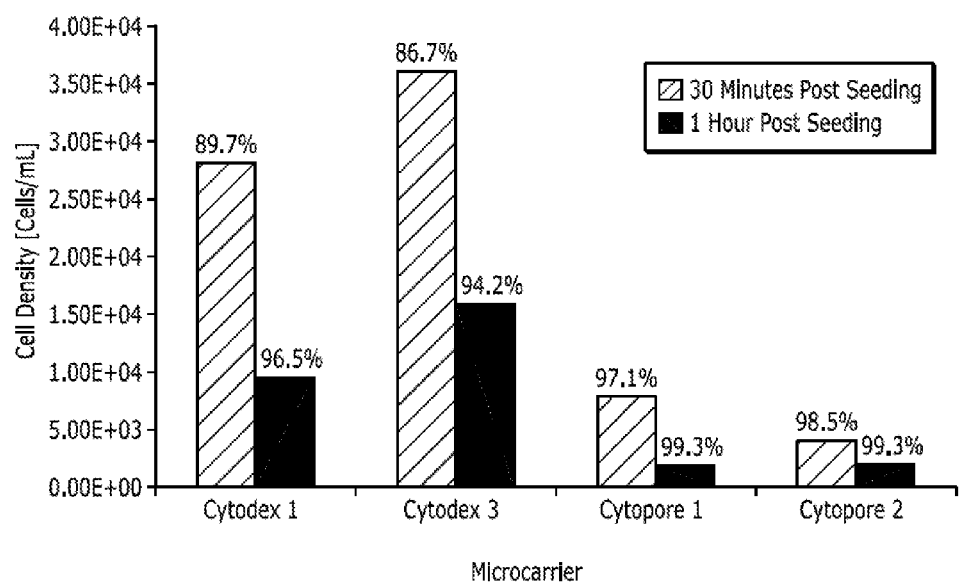

FIG. 8 presents a comparison of the cell density of subclone 1-A in M18M media comprising four different microcarriers 30 and 60 minutes post-inoculation.

Figure 9:
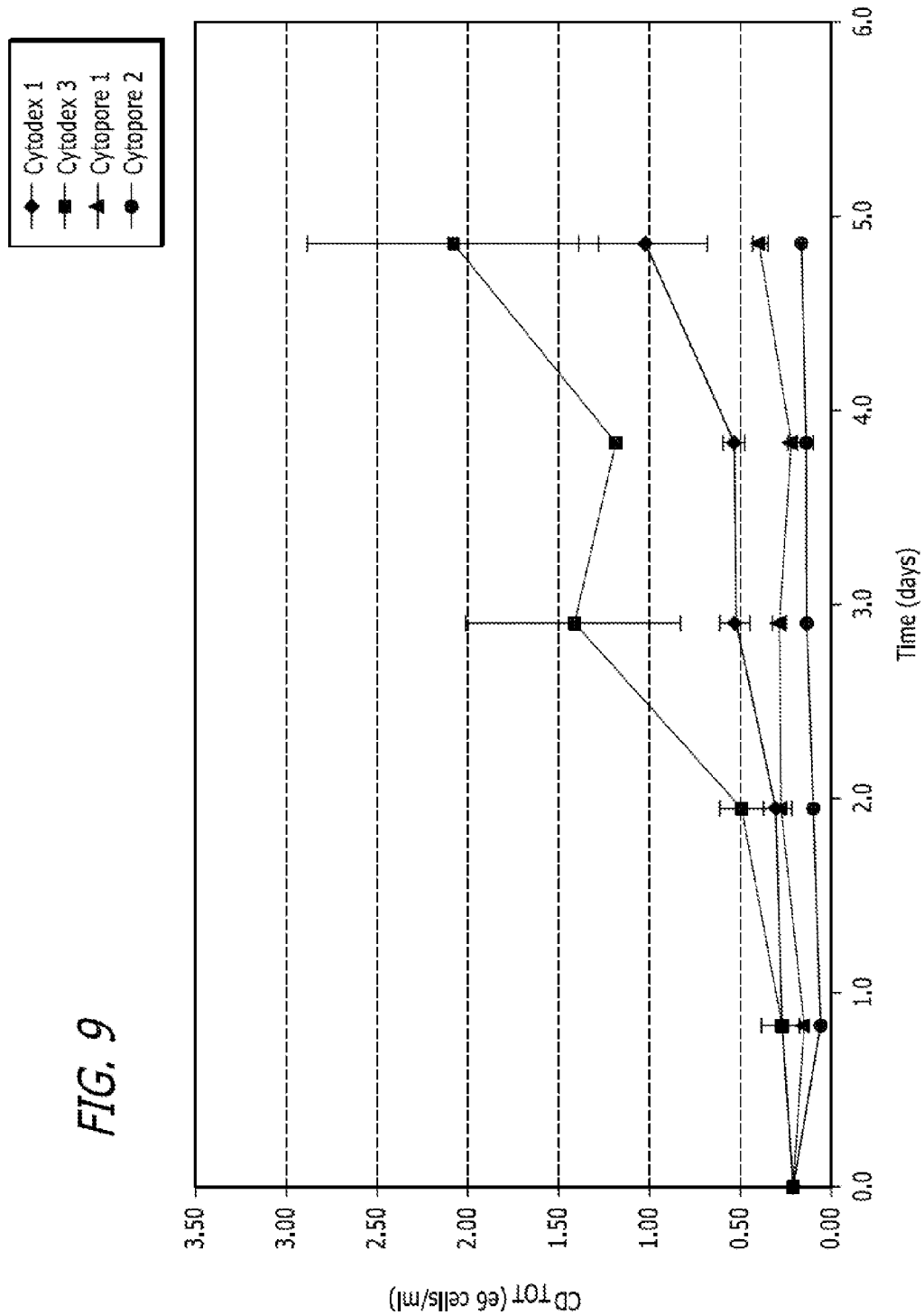

FIG. 9 presents a comparison of the cell yield of subclone 1-A in M18M media comprising four different microcarriers.

Figure 10:
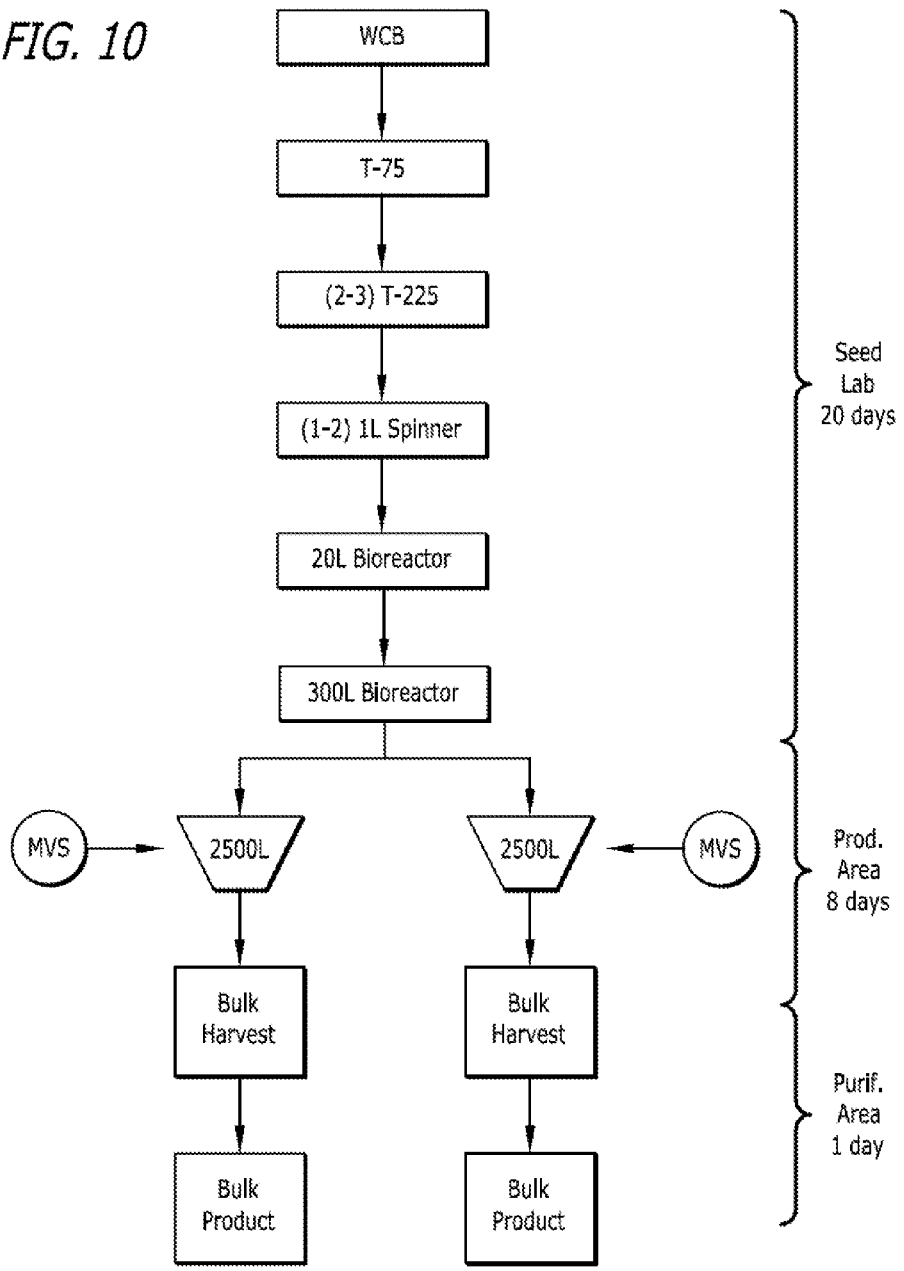

FIG. 10 outlines one cell culture scale up process which can be utilized for commercial scale production of vaccine material.

FIG. 11 outlines two purification processes which can be utilized for commercial scale purification of vaccine material from cell-culture.

FIG. 12 presents the results of Cellufine Sulfate (CS) chromatography after or in combination with Benzonase treatment. Panel A) The OD profile of column chromatography using Cellufine Sulfate is shown in the left panel, arrows indicate the time the load, wash and elution were started. Agarose gel electrophoresis (right panel) show that the DNA contaminant is present in the starting material (lane 2) and the flow through (lane 3) but is absent in the material eluted from the column (lane 4), lane 1 is molecular weight marker. Panel B) Depicts the scheme for MDCK dsDNA Degradation Using Benzonase On-Column Treatment.

Figure 13:
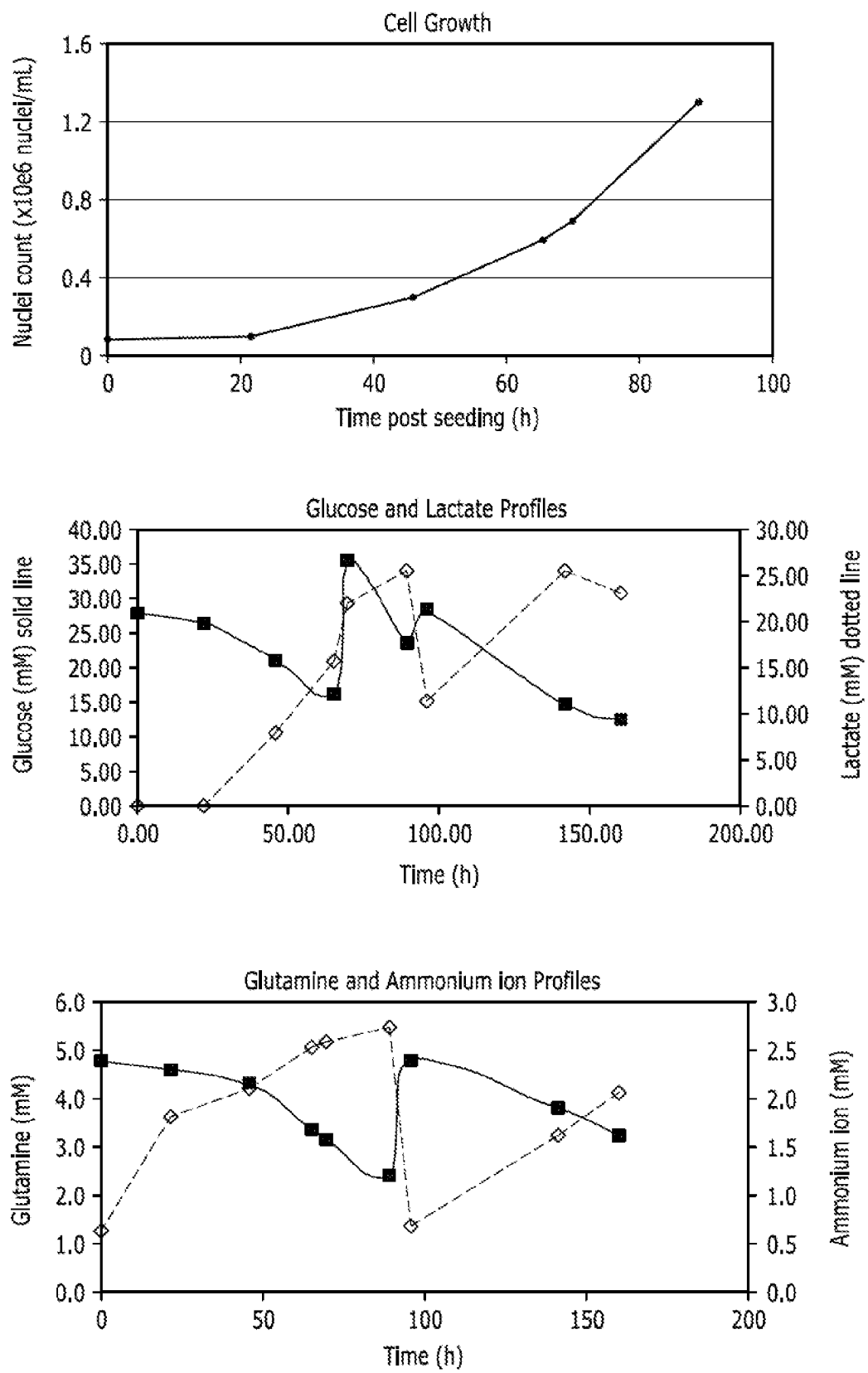

FIG. 13 presents several curves of the 30 L SUB process for the production of B/Malaysia/2506/04 in MDCK subclone 1-B. Top panel is the growth curve of the cells during the growth phase. The metabolite profiles for glucose (middle panel, solid line), lactate (middle panel, dotted line), glutamine (bottom panel, solid line) and ammonium ion (bottom panel, dotted line) for this run were measured by Bioprofile.

Figure 14A:
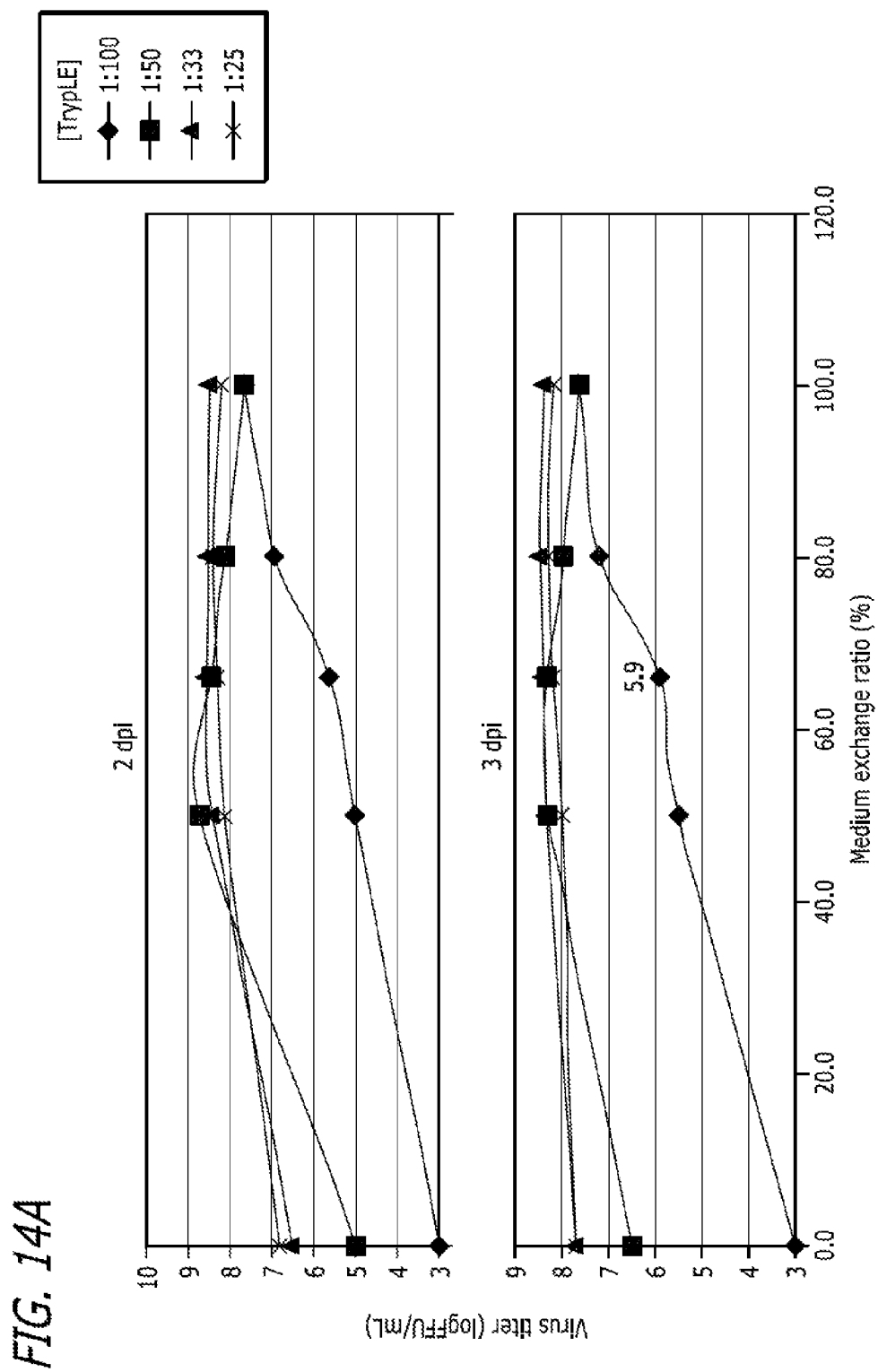
Figure 14B:
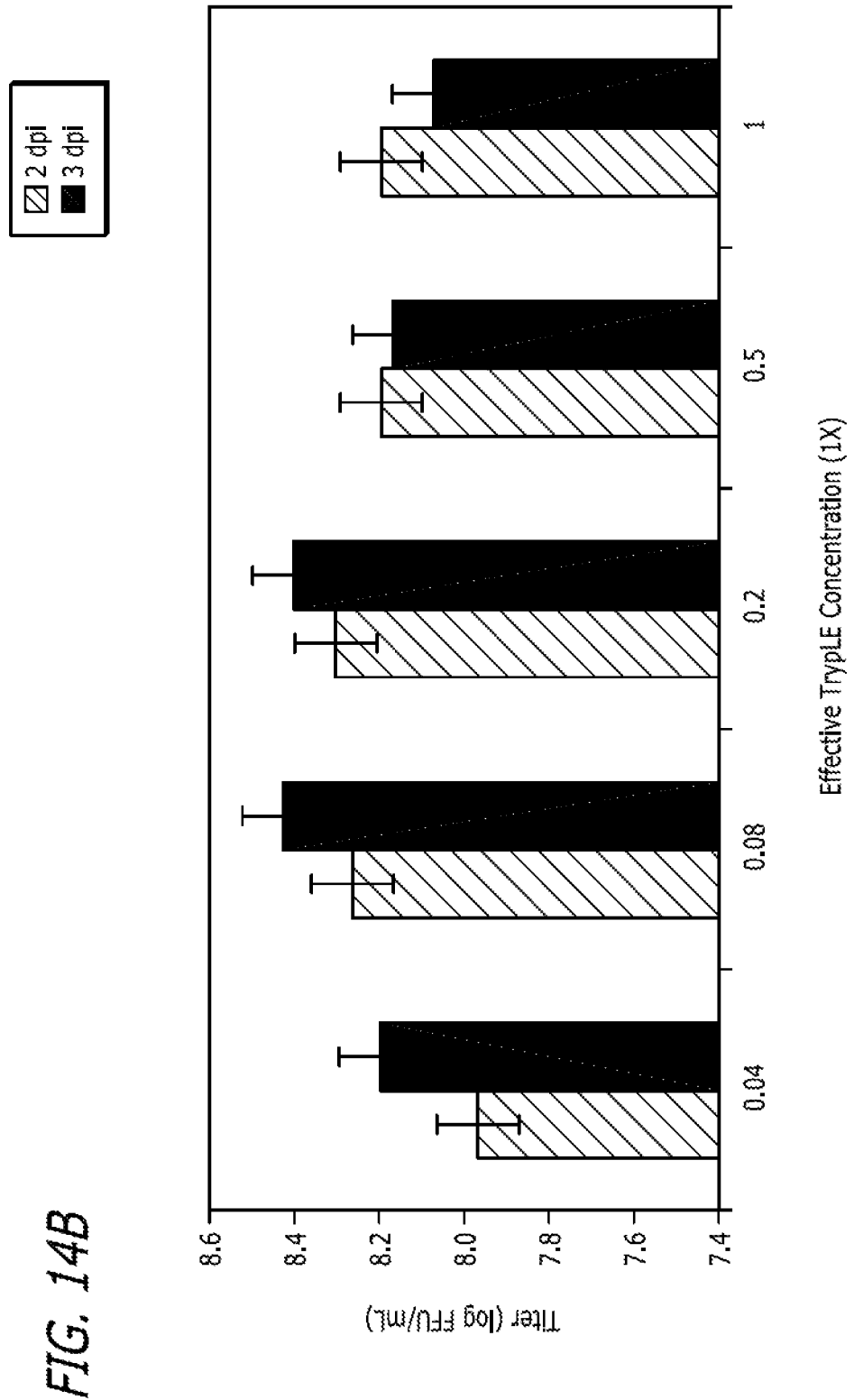
Figure 14C:
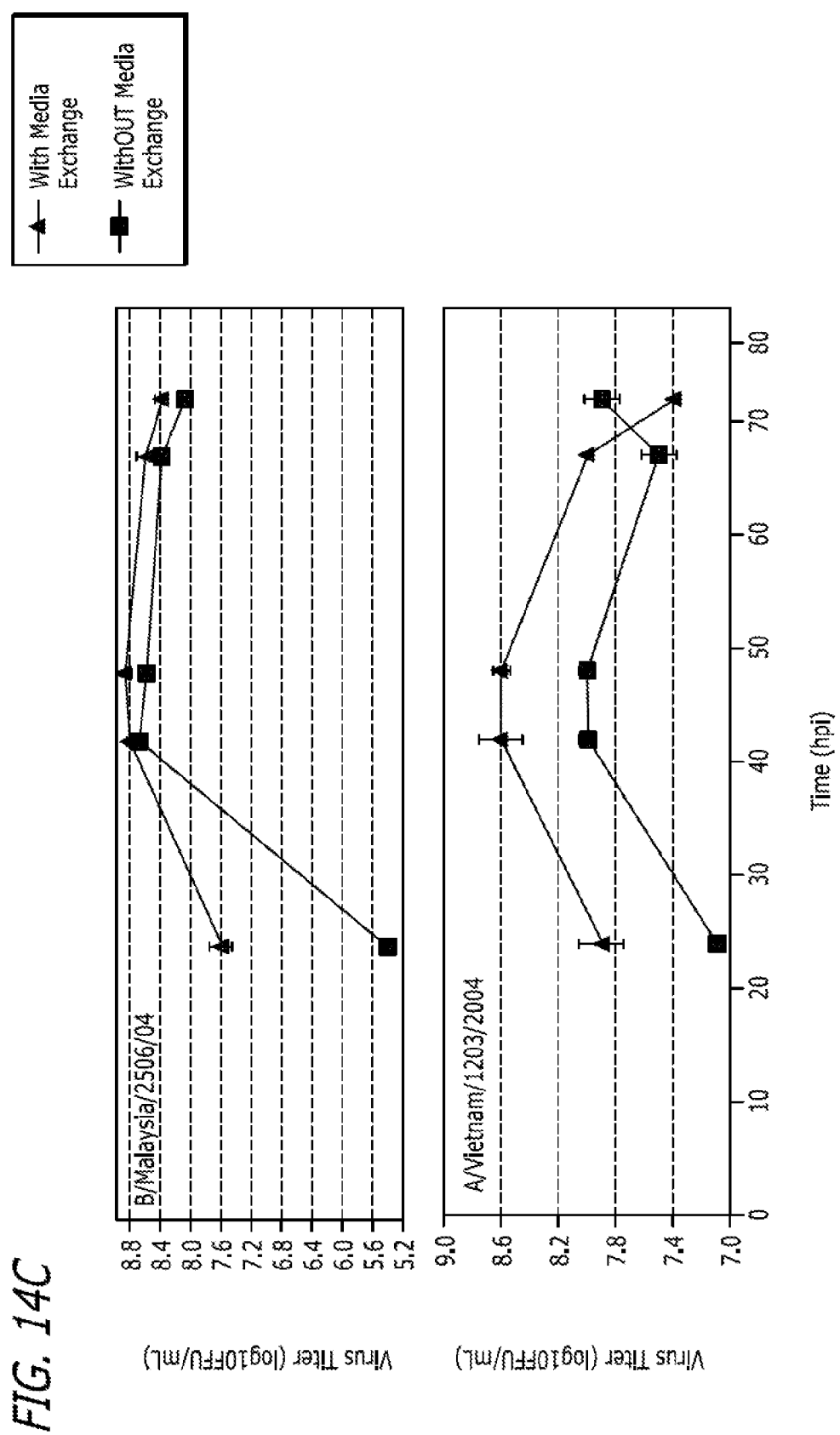

FIG. 14 presents the results of pilot studies without media exchange for the SUB process. A) Plots of the viral titers obtained for medium exchange ratios between 0% and 100% at 2 and 3 dpi (top and bottom, respectively). B) Plots of the peak viral titer at 2 and 3 dpi for effective TrypLE concentrations of between 0.04 and 1. C) Plots of the viral titers over time for B/Malaysia/2506/04 (to) and A/Vietnam/1203/2004 (bottom) after infection with (triangles) or without (squares) media exchange.

Figure 15:
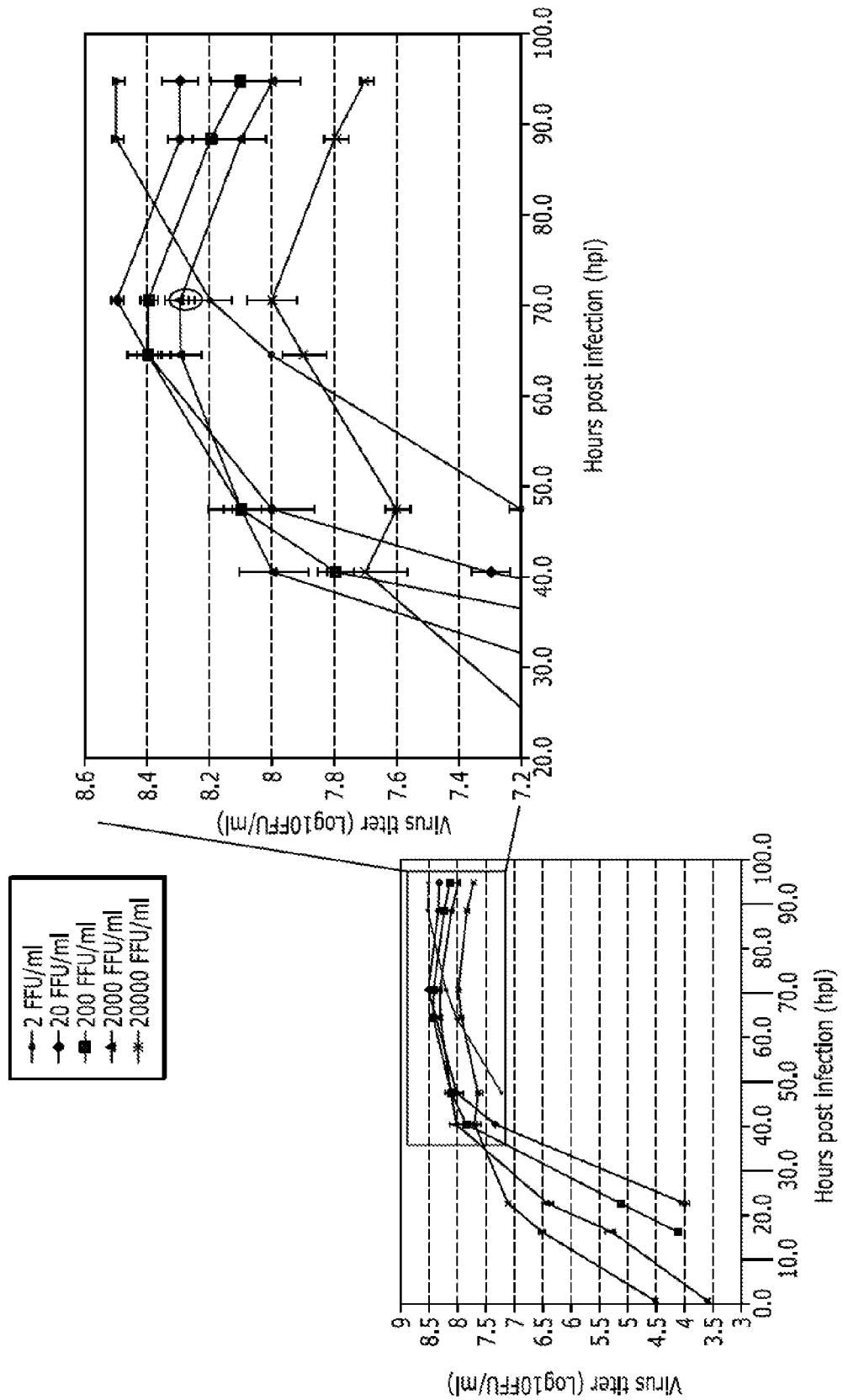

FIG. 15 plots the A/Solomon Islands/3/06 viral titer over time (hours post infection) for different MOIs used. The viral yields from 20 to 96 hours post infection are boxed and this area of the plot is expanded to the right. The peak viral harvest of the culture infected at 2000 FFU/mL is circled.

7. DETAILED DESCRIPTION OF THE INVENTION

The present invention is based in part on the discovery that cloned MDCK cell lines can be obtained that support the replication of influenza viruses, particularly cold-adapted, and/or temperature sensitive, and/or attenuated influenza viruses, to high titer. Thus, the present invention provides, in one aspect, MDCK cell lines which have been adapted to a variety of cell culture conditions, including serum-free media formulations, that can support the replication of influenza viruses, e.g., cold-adapted, and/or temperature sensitive, and/or attenuated influenza viruses, to high titer and are referred to herein as "cells of the invention".

In addition, the present invention provides cell culture compositions comprising cells of the invention and other components, which can include, but are not limited to, media (e.g., a media disclosed herein), media components, buffers, chemical compounds, additional cell types, viral material (e.g., viral genomes, viral particles) and heterologous proteins.

The present invention also provides methods and media formulations useful for the cultivation of MDCK cells, with one or more specific characteristics including but not limited to, being non-tumorigenic (e.g., not forming nodules in a nude mouse) and/or being non-oncogenic and/or growth as adherent cells and/or growth as non-adherent cells and/or having an epithelial-like morphology and/or supporting the replication of various viruses including but not limited to orthomyxoviruses, paramyxoviruses, rhabdoviruses and flaviviruses and/or supporting the growth of influenza viruses, including cold-adapted, and/or temperature sensitive, and/or attenuated influenza viruses, to high titer. The culture conditions of the present invention include serum containing and serum-free media formulations, as well as animal protein-free (APF) formulations.

In addition, the present invention also provides methods of producing vaccine material (e.g., influenza virus) in MDCK cells, preparing vaccine material from MDCK cells, and methods of preventing influenza infection utilizing vaccine materials produced in MDCK cells. The cells of the invention are particularly useful for the production of cold adapted/temperature sensitive/attenuated (ca/ts/att) influenza strains (e.g., those in FluMist®) which do not replicate as efficiently in other mammalian cell lines (e.g., Vero, PerC6®, HEK-293, MRC-5 and WI-38 cells).

7.1 Definitions

Tumorigenicity, as used herein, has the ordinary meaning attributed to this term by one skilled in the art. Tumorigenicity is, in one embodiment, determined by the adult nude mouse model (e.g., Stiles et al., 1976, Cancer Res, 36:1353, and Example 5 below). Tumorigenicity may also be tested by other assays, for example, by injection into a chick embryo and/or topical application to the chorioallantois (Leighton et al., 1970, Cancer, 26:1024).

The term "recombinant" indicates that the material (e.g., a nucleic acid or protein) has been artificially or synthetically (non-naturally) altered by human intervention. The alteration can be performed on the material within, or removed from, its natural environment or state. Specifically, when referring to a virus, e.g., an influenza virus, the virus is recombinant when it is produced by the expression of a recombinant nucleic acid.

The term "reassortant," when referring to a virus, indicates that the virus includes genetic and/or polypeptide components derived from more than one parental viral strain or source. For example, a 7:1 reassortant includes 7 viral genomic segments (or gene segments) derived from a first parental virus, and a single complementary viral genomic segment, e.g., encoding hemagglutinin or neuraminidase, from a second parental virus. A 6:2 reassortant includes 6 genomic segments, most commonly the 6 internal genes from a first parental virus, and two complementary segments, e.g., hemagglutinin and neuraminidase, from a different parental virus.

The term "about," as used herein, unless otherwise indicated, refers to a value that is no more than 10% above or below the value being modified by the term. For example, the term "about 5 µg/kg" means a range of from 4.5 µg/kg to 5.5 µg/kg. As another example, "about 1 hour" means a range of from 54 minutes to 66 minutes.

The terms "temperature sensitive," "cold adapted" and "attenuated" are well known in the art. For example, the term "temperature sensitive" ("ts") indicates that the virus exhibits a 100 fold or greater reduction in titer at a higher temperature, e.g., 39° C. relative to a lower temperature, e.g., 33° C. for influenza A strains, and that the virus exhibits a 100 fold or greater reduction in titer at a higher temperature, e.g., 37° C. relative to a lower temperature, e.g., 33° C. for influenza B strains. For example, the term "cold adapted" ("ca") indicates that the virus exhibits a higher growth rate at a lower temperature, e.g., 25° C. within 100 fold of its growth at a higher temperature, e.g., 33° C. For example, the term "attenuated" ("att") indicates that the virus replicates in the upper airways of ferrets but is not detectable in lung tissues, and does not cause influenza-like illness in the animal. It will be understood that viruses with intermediate phenotypes, i.e., viruses exhibiting titer reductions less than 100 fold at 39° C. (for A strain viruses) or 37° C. (for B strain viruses), exhibiting growth at 25° C. that is more than 100 fold than its growth at 33° C. (e.g., within 200 fold, 500 fold, 1000 fold, 10,000 fold less), and/or exhibit reduced growth in the lungs relative to growth in the upper airways of ferrets (i.e., partially attenuated) and/or reduced influenza like illness in the animal, are also useful viruses encompassed by the invention. Growth indicates viral quantity as indicated by titer, plaque size or morphology, particle density or other measures known to those of skill in the art.

7.2 Cell Characteristics

The cells according to the invention are in one embodiment, vertebrate cells. In another embodiment, the cells of the invention are mammalian cells, e.g., from hamsters, cattle, monkeys or dogs, in particular kidney cells or cell lines derived from these. In still another embodiment, the cells of the invention are MDCK cells (e.g., lineally related to ATCC CCL-34 MDCK) and are specifically referred to herein as "MDCK cells of the invention" and are encompassed by the term "cells of the invention". In a specific embodiment, the cells of the invention are derived from ATCC CCL-34 MDCK. Cells of the invention may be derived from CCL-34 MDCK cells by methods well known in the art. For example, the CCL-34 MDCK cells may be first passaged a limited number of times in a serum containing media (e.g., Dulbecco's Modified Eagle Medium (DMEM)+10% Fetal Bovine Serum (FBS)+4 mM glutamine+4.5 g/L glucose, or other media described herein) followed by cloning of individual cells and characterization of the clones. Clones with superior biological and physiological properties including, but not limited to, doubling times, tumorigenicity profile and viral production, can be selected for the generation of a master cell bank (MCB).

In a first aspect, the invention provides a Madin-Darby Canine Kidney (MCDK) cell, wherein a cell culture composition comprising a plurality of the MDCK cells supports replication of an influenza virus. In a specific aspect, the MDCK cells support the replication of an influenza virus having one or more of the following characteristics: cold adapted, attenuated, and temperature sensitive. In certain embodiments the ability of the MDCK cells to support viral replication is determined by measuring the yield of virus obtained from an infected cell culture (e.g., using a median tissue culture infectious dose ($TCID_{50}$) assay or fluorescent focus assay (FFA)). In certain embodiments, the MDCK cells support replication of the influenza virus to a base 10 logarithm of the median tissue culture infection dose per milliliter ($\log_{10}$ $TCID_{50}$/mL) of at least about 7.0. In certain embodiments, the MDCK cells support replication of the influenza virus to a $\log_{10}$ $TCID_{50}$/mL of at least about 7.2. In certain embodiments, the MDCK cells support replication of the influenza virus to a $\log_{10}$ $TCID_{50}$/mL of at least about 7.4. In certain embodiments, the MDCK cells support replication of the influenza virus to a $\log_{10}$ $TCID_{50}$/mL of at least about 7.6. In certain embodiments, the MDCK cells support replication of the influenza virus to a $\log_{10}$ $TCID_{50}$/mL of at least about 7.8. In certain embodiments, the MDCK cells support replication of the influenza virus to a $\log_{10}$ $TCID_{50}$/mL of at least about 8.0. In certain embodiments, the MDCK cells support replication of the influenza virus to a $\log_{10}$ $TCID_{50}$/mL of at least about 8.2. In certain embodiments, the MDCK cells support replication of the influenza virus to a $\log_{10}$ $TCID_{50}$/mL of at least about 8.4. In certain embodiments, the MDCK cells support replication of the influenza virus to a $\log_{10}$ $TCID_{50}$/mL of at least about 8.6. In certain embodiments, the MDCK cells support replication of the influenza virus to a $\log_{10}$ $TCID_{50}$/mL of at least about 8.8. In certain embodiments, the MDCK cells support replication of the influenza virus to a $\log_{10}$ $TCID_{50}$/mL of at least about 9.0. Alternatively, or optionally, viral yield can be quantified by determining the concentration of virus present in a sample according to a fluorescent focus assay (described as Example 6, and known in the art, see e.g., Stokes et al., 1988, J Clin Microbiol. 26:1263-6 and U.S. Patent Publication 20040265987). The FFA values are often reported as $\log_{10}$ FFU/mL (fluorescent focus units/mL). Accordingly, in certain embodiments the MDCK cells support replication of the influenza virus to a base 10 logarithm of fluorescent focus units per milliliter ($\log_{10}$ FFU/mL) of at least about 7.0, or to a $\log_{10}$ FFU/mL of at least about 7.2, or to a $\log_{10}$ FFU/mL of at least about 7.4, or to a $\log_{10}$ FFU/mL of at least about 7.6, or to a $\log_{10}$ FFU/mL of at least about 7.8, or to a $\log_{10}$ FFU/mL of at least about 8.0, or to a $\log_{10}$ FFU/mL of at least about 8.2, or to a $\log_{10}$ FFU/mL of at least about 8.4, or to a $\log_{10}$ FFU/mL of at least about 8.6, or to a $\log_{10}$ FFU/mL of at least about 8.8, or to a $\log_{10}$ FFU/mL of at least about 9.0.

In certain embodiments, the cells of the invention are propagated in culture to generate a cell culture composition (also referred to herein as "a cell culture composition of the invention"). In one embodiment, a cell culture composition of the invention comprises as the only host cell type MDCK cells of the invention, wherein the cell culture composition supports replication of an influenza virus having one or more of the following characteristics: cold-adapted, attenuated, and temperature sensitive to a $\log_{10}$ $TCID_{50}$/mL and/or a $\log_{10}$ FFU/mL of at least about 7.0, at least about 7.2, at least about 7.4, at least about 7.6, at least about 7.8, at least about 8.0, at least about 8.2, at least about 8.4, at least about 8.6, at least about 8.8, at least about 9.0, at least about 9.2, at least about 9.4, at least about 9.6, at least about 9.8, at least about 10.0, at least about 10.2, at least about 10.4, at least about 10.6, at least about 10.8 or at least about 11.0.

In one aspect, the cells of the invention are adapted to growth in a media of choice (e.g., a serum-free or APF media, such as those described herein). Such adaptation may occur prior to, concurrently with, or subsequent to the cloning of individual cells. In certain embodiments, cells of the invention are adapted to grow in MediV 101, MediV 102, MediV 103, MediV 104, MediV 105, M-32, MediV 107, M18M or growth optimized derivatives thereof, as described hereinafter. Accordingly, the cells of the invention can be propagated in a media as disclosed herein to generate a cell culture composition of the invention. In one embodiment, a cell culture composition of the invention comprises as the only host cell type MDCK cells of the invention, wherein the growth media is a serum-free medium.

In a specific embodiment of the invention the cells are of the cell lines including, but not limited to, those which have been deposited with the American Type Culture Collection (10801 University Boulevard, Manassas, Va. 20110-2209) on Jan. 5, 2005 and assigned ATCC Deposit Nos. PTA-6500, PTA-6501, PTA-6502, PTA-6503 and those subclones 1-A and 1-B, deposited on Oct. 5, 2006 and assigned ATCC Deposit Nos. PTA-7909 and PTA-7910, respectively. These deposits will be maintained under the terms of the Budapest Treaty on the International Recognition of the Deposit of Microorganisms for the Purposes of Patent Procedure. In one embodiment, the MDCK cells of the invention are used to generate a cell bank useful for the preparation of vaccine material suitable for approval by the U.S. Food and Drug Administration for human use. In one embodiment, a cell culture composition of the invention comprises as the only host cell type MDCK cells deposited as ATCC Accession number PTA-6500, PTA-6501, PTA-6502, PTA-6503, PTA-7909, or PTA-7910. In a specific embodiment, a cell culture composition of the invention comprises as the only host cell type MDCK cells deposited as ATCC Accession number PTA-7909. In another specific embodiment, a cell culture composition of the invention comprises as the only host cell type MDCK cells deposited as ATCC Accession number PTA-7910.

In some embodiments, the invention provides MDCK cell lines derived from the cell line MDCK (CCL 34) by passaging and selection with respect to one or more specific characteristics including but not limited to, growing as adherent cells either in serum containing, or serum-free media or animal protein-free media, growing as non-adherent cells either in serum containing, or serum-free media or animal protein-free media, having an epithelial-like morphology, being non-tumorigenic (e.g., not forming nodules in a nude mouse), and/or being non-oncogenic, and/or supporting the replication of various viruses including but not limited to orthomyxoviruses, paramyxoviruses, rhabdoviruses and flaviviruses.

In one embodiment, the MDCK cells of the invention are non-tumorigenic. In another embodiment, a cell culture composition of the invention comprises as the only host cell type MDCK cells of the invention, wherein the MDCK cells of the invention are non-tumorigenic. Methods for determining if cells are tumorigenic are well known in the art (see, for example, Leighton et al., 1970, Cancer, 26:1024 and Stiles et al., 1976, Cancer Res, 36:1353), the method currently preferred by the U.S. Food and Drug Administration uses the nude mouse model detailed in Section 9.7 below. In a specific embodiment, the MDCK cells of the invention are non-tumorigenic in the adult nude mouse model (see, Stiles et al., Id and Section 9.7 below). In another specific embodiment, the MDCK cells of the invention are non-tumorigenic when injected into a chick embryo and/or topically applied to the chorioallantois (see, Leighton et al., Id). In still another embodiment, the MDCK cells of the invention are non-tumorigenic in the adult nude mouse model but not when injected into a chick embryo and/or topically applied to the chorioallantois. In yet another embodiment, the MDCK cells of the invention are non-tumorigenic in the adult nude mouse model and when injected into a chick embryo and/or topically applied to the chorioallantois. In still another embodiment, the MDCK cells of the invention are non-tumorigenic after at least 20 passages, or after at least 30 passages, or after at least 40 passages, or after at least 50 passages, or after at least 60 passages, or after at least 70 passages, or after at least 80 passages, or after at least 90 passages, or after at least 100 passages in a medium. In yet another specific embodiment the medium is a media described herein (e.g., Medi 105).

Tumorigenicity may be quantified in numerous ways known to one of skill in the art. One method commonly utilized is to determine the "$TD_{50}$" value which is defined as the number of cells required to induce tumors in 50% of the animals tested (see, e.g., Hill R. The $TD_{50}$ assay for tumor cells. In: Potten C, Hendry J, editors. Cell clones. London: Churchill Livingstone; 1985. p. 223). In one embodiment, the MDCK cells of the invention have a $TD_{50}$ value of between about $10^{10}$ to about $10^1$, or between about $10^8$ to about $10^3$, or between about $10^7$ to about $10^4$. In a specific embodiment, the MDCK cells of the invention have a $TD_{50}$ value of more than about $10^{10}$, or of more than about $10^9$, or of more than about $10^8$, or of more than about $10^7$, or of more than about $10^6$, or of more than about $10^5$, or of more than about $10^4$, or of more than about $10^3$, or of more than about $10^2$, or of more than about $10^1$.

In one embodiment, the MDCK cells of the invention are non-oncogenic. In another embodiment, a cell culture composition of the invention comprises as the only host cell type MDCK cells of the invention, wherein the MDCK cells are non-oncogenic. Methods for determining if cells are oncogenic are well known in the art and generally involve the inoculation of cell lysates and/or DNA into newborn rodent species and evaluation of any tumor formation over time (see, for example, Nowinski and Hays, 1978, J. Virol., 27: 13-8; Peeper, et al., 2002, Nat Cell Biol., 4:148-53; Code of Federal Regulation (CFR), "Oncogenicity", Title 40, Vol. 8, Chapter 1, section 798.330, pp. 160-164). For example, cell lysates and/or DNA from at least $10^7$ cell equivalents are injected into newborn rodents (e.g., hamster, nude mice, rats) typically less then 4 days old which are then monitored for up to five months or more. Oncogenicity assays are routinely performed by commercial testing companies (e.g., BioReliance, see Protocols #001031 and #001030). In one embodiment, cell lysates and/or DNA from at least $10^5$, or at least $10^6$, or at least $10^7$ MDCK cells of the invention do not induce tumor formation in 2 months, or in 3 months, or in 4 month, or in 5 months, or in 6 months, or longer, when injected into a newborn rodent species. In another embodiment, 0.01 mg, or 0.02 mg, or 0.03 mg, or 0.04 mg, or 0.05 mg, or 0.06 mg, or 0.07 mg, or 0.08 mg, or 0.09 mg, or 0.10 mg, or more, DNA from an MDCK cell of the invention does not induce tumor formation in 2 months, or in 3 months, or in 4 month, or in 5 months, or in 6 months, or longer, when injected into a newborn rodent species.

In another embodiment, the cells of the invention grow as adherent cells either in serum-containing or serum-free media or animal protein-free media. In yet another embodiment, the cells of the invention grow as non-adherent cells (e.g., capable of growth under non-adherent conditions) either in serum containing or serum-free media or animal protein-free media. In still another embodiments, the cells of the invention have an epithelial-like morphology. In yet another embodiment, the MDCK cells of the invention support the replication of various viruses including but not limited to orthomyxoviruses, paramyxoviruses, rhabdoviruses and flaviviruses. It is contemplated that the MDCK cells of the invention may have any combination of one or more specific characteristics including but not limited to, being non-tumorigenic, being non-oncogenic, growing as adherent cells, growing as non-adherent cells, having an epithelial-like morphology, supporting the replication of various viruses, and supporting the growth of influenza viruses to high titer, e.g., a $\log_{10} TCID_{50}/mL$ of at least about 7.0, at least about 7.2, at least about 7.4, at least about 7.6, at least about 7.8, at least about 8.0, at least about 8.2, at least about 8.4, at least about 8.6, at least about 8.8, at least about 9.0, at least about 9.2, at least about 9.4, at least about 9.6, at least about 9.8, at least about 10.0, at least about 10.2, at least about 10.4, at least about 10.6, at least about 10.8 or at least about 11.0 and/or a $\log_{10} FFU/mL$ of at least about 7.0, at least about 7.2, at least about 7.4, at least about 7.6, at least about 7.8, at least about 8.0, at least about 8.2, at least about 8.4, at least about 8.6, at least about 8.8, at least about 9.0, at least about 9.2, at least about 9.4, at least about 9.6, at least about 9.8, at least about 10.0, at least about 10.2, at least about 10.4, at least about 10.6, at least about 10.8 or at least about 11.0. In certain embodiments, a cell culture composition of the invention comprises as the only host cell type MDCK cells of the invention, wherein the MDCK cells of the invention have any combination of one or more specific characteristics including but not limited to, being non-tumorigenic, being non-oncogenic, growing as adherent cells, growing as non-adherent cells, having an epithelial-like morphology, supporting the replication of various viruses, and supporting the growth of influenza viruses to high titer (e.g., $\log_{10} TCID_{50}/mL$ and/or a $\log_{10} FFU/mL$ of at least about 7.8).

It is contemplated that each and every passage of the MDCK cells of the invention can be documented in sufficient detail such that the complete lineage of each cell line is available. The documentation of each and every passage may facilitate approval by the U.S. Food and Drug Administration and other regulatory bodies around the world for the use of the MDCK cells of the invention for the preparation of vaccine material.

In another embodiment, the MDCK cells of the invention are free of microbial contaminants (e.g., bacterial, viral and fungal contaminants). Methods for testing for the presence of bacterial and fungal contaminants are well known in the art and routinely performed by commercial contractors (e.g., BioReliance®, Rockville, Md.). Accepted microbial sterility and mycoplasma tests are detailed in Section 9.7 below. Specific examples of microbial agents which may be tested for are listed in Table 4.

In yet another embodiment, the MDCK cells of the invention support the replication of viruses including but not limited to orthomyxoviruses (including influenza A and/or B strains), paramyxoviruses (including RSV A and/or B, human metapneumovirus and parainfluenza 1, 2 and/or 3), rhabdoviruses and flaviviruses.

In a specific embodiment, the MDCK cells of the invention support the replication of cold adapted/temperature sensitive (ca/ts) influenza viruses such as those found, for example, in FluMist® (Belshe et al., 1998, *N Engl J Med* 338:1405; Nichol et al., 1999, *JAMA* 282:137; Jackson et al., 1999, *Vaccine,* 17:1905) and/or reassortant viruses comprising the backbone (e.g., the remaining gene segments) of these viruses or comprising the backbone (or one or more vRNA segment(s)) of influenza viruses having one or more of the following characteristics: cold adapted, attenuated, and temperature sensitive. One indication of the ability of a cell to support viral replication is the yield of virus obtained from an infected cell culture. Viral yield can be determined by numerous methods known to one skilled in the art. For example, viral yield can be quantified by determining the concentration of virus present in a sample according to a median tissue culture infectious dose ($TCID_{50}$) assay that measures infectious virions or fluorescent focus assay (FFA). The $TCID_{50}$ values are often reported as the $\log_{10} TCID_{50}/mL$ and the FFA values are often reported as $\log_{10} FFU/mL$ (fluorescent focus units/mL).

In one embodiment, the MDCK cells of the invention support the replication of influenza viruses (e.g., ca/ts strains) to a $\log_{10} TCID_{50}/mL$ of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In another embodiment, the MDCK cells of the invention support the replication of influenza viruses (e.g., ca/ts strains) to a $\log_{10} TCID_{50}/mL$ of at least about 6.0, or at least about 6.2, or at least about 6.4, or at least about 6.6, or at least about 6.8, or at least about 7.0, or at least about 7.2, or at least about 7.4, or at least about 7.6, or at least about 7.8, or at least about 8.0, or at least about 8.2, or at least about 8.4, or at least about 8.6, or at least about 8.8, or at least about 9.0, or at least about 9.2, or at least about 9.4, or at least about 9.6, or at least about 9.8. In still another embodiment, the MDCK cells of the invention support the replication of influenza viruses (e.g., ca/ts strains) to a $\log_{10} FFU/mL$ of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In yet another embodiment, the MDCK cells of the invention support the replication of influenza viruses (e.g., ca/ts strains) to a $\log_{10} FFU/mL$ of at least about 6.0, or at least about 6.2, or at least about 6.4, or at least about 6.6, or at least about 6.8, or at least about 7.0, or at least about 7.2, or at least about 7.4, or at least about 7.6, or at least about 7.8, or at least about 8.0, or at least about 8.2, or at least about 8.4, or at least about 8.6, or at least about 8.8, or at least about 9.0, or at least about 9.2, or at least about 9.4, or at least about 9.6, or at least about 9.8.

It is well known in the art that the wild-type viruses used in preparation of the vaccine strains for annual vaccination against epidemic influenza are recommended annually by the Vaccines and Related Biological Products Advisory Committee to the Centers for Biologics Evaluation and Research (CBER) or the World Health Organization (WHO) and the European Medicines Evaluation Agency (EMEA), and are provided to manufacturers by the FDA or the Centers for Disease Control and Prevention (CDC). These strains may then used for the production of reassortant vaccine strains which generally combine the NA and/or HA genes of the wild-type viruses with the remaining gene segments derived from a donor virus (often referred to as a master donor virus or MDV) which will have certain desirable characteristics. For example, an MDV strain may be cold-adapted, and/or temperature sensitive, and/or attenuated, and/or have a high growth rate. The embodiments that follow immediately below relate to cold-adapted, and/or temperature sensitive, and/or attenuated versions of different influenza strains (e.g., wild type strains recommended by one or more health organization). As one skilled in the art is aware, such cold-adapted, and/or temperature sensitive, and/or attenuated influenza viruses can be readily made by obtaining recombinant and/or reassortant influenza viruses that comprise the HA and NA gene segments from the strain of interest and the remaining gene segments from a suitable cold-adapted, and/or temperature sensitive, and/or attenuated influenza strain (also referred to herein as a "cold-adapted, temperature sensitive, attenuated backbone") such as, for example, the cold-adapted, temperature sensitive, attenuated influenza viruses found in FluMist®, as well as strain A/Ann Arbor/6/60 or B/Ann Arbor/1/66. As used herein a recombinant and/or reassortant virus that comprises HA and NA gene segments from a wild type influenza virus strain and the remaining gene segments from cold-adapted, temperature sensitive, attenuated influenza virus are also referred to by the wild type strain designation preceded by the identifier "Ca", for example a recombinant and/or reassortant virus that comprises HA and NA gene segments from A/New Calcdonia/20/99 and the remaining segments from a cold-adapted, temperature sensitive, attenuated influenza virus may be designated "ca A/New Calcdonia/20/99." In some embodiments, the reassortant influenza virus comprises at least one gene segment from A/Ann Arbor/6/60, B/Ann Arbor/1/66, A/Leningrad/134/47/57, B/Leningrad/14/17/55 or A/Puerto Rico/8/34.

In certain embodiments, the MDCK cells of the invention support the replication of a cold-adapted, and/or temperature sensitive, and/or attenuated version (e.g., reassortant) of at least one influenza strain (e.g., an influenza A strain, an influenza B strain) recommended and/or provided annually by one or more health organization including, but not limited to, the CBER, the WHO, the EMEA, the FDA and the CDC, to a $\log_{10} TCID_{50}/mL$ and/or a $\log_{10} FFU/mL$ of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In one embodiment, a cell culture composition of the invention comprises as the only host cell type MDCK cells of the invention, wherein the cell culture composition supports replication of a cold-adapted, and/or temperature sensitive, and/or attenuated version (e.g., reassortant) of at least one influenza strain (e.g., an influenza A strain, an influenza B strain) recommended and/or provided annually by one or more health organization including, but not limited to, the CBER, the WHO, the EMEA, the FDA and the CDC, to a $\log_{10} TCID_{50}/mL$ and/or a $\log_{10} FFU/mL$ of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8

In certain other embodiments, the MDCK cells of the invention support the replication of a cold-adapted, and/or temperature sensitive, and/or attenuated version of at least one influenza A strain to a $\log_{10} TCID_{50}/mL$ and/or a $\log_{10} FFU/mL$ of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In one embodiment, a cell culture composition of the invention comprises as the only host cell type MDCK cells of the invention, wherein the cell culture composition supports replication of a cold-adapted, and/or temperature sensitive, and/or attenuated version of at least one influenza A strain to a $\log_{10} TCID_{50}/mL$ and/or a $\log_{10} FFU/mL$ of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. It is contemplated that the influenza A strain may be of any subtype (e.g., $H_1N_1$, $H_3N_2$, $H_7N_7$, $H_5N_1$, $H_9N_2$, $H_1N_2$, $H_2N_2$). Presently at least 16 different HA and 9 different NA subtypes have been identified in influenza A viruses. Accordingly, the influenza A strain may comprise any combination of HA and NA subtypes currently known or identified in the future.

In certain other embodiments, the MDCK cells of the invention support the replication of a cold-adapted, and/or temperature sensitive, and/or attenuated version of at least one influenza B strain to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In one embodiment, a cell culture composition of the invention comprises as the only host cell type MDCK cells of the invention, wherein the cell culture composition supports replication of a cold-adapted, and/or temperature sensitive, and/or attenuated version of at least one influenza B strain to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. Influenza B viruses are not currently divided into subtypes based upon their hemagglutinin and neuraminidase proteins, rather they are classified by lineage. Presently, influenza B virus strains are divided into two lineages, the B/Yamagata and the B/Victoria lineages of which there are numerous sublineages. Accordingly, the influenza B strain may be derived from any lineage and/or sublineage currently known or identified in the future.

In certain embodiments, the MDCK cells of the invention support the replication of a cold-adapted, and/or temperature sensitive, and/or attenuated version of influenza strain A/New Calcdonia (i.e., ca A/New Calcdonia) to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In certain embodiments, the MDCK cells of the invention support the replication of a cold-adapted, and/or temperature sensitive, and/or attenuated version of influenza strain A/Hiroshima (i.e., ca A/Hiroshima) to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In certain embodiments, the MDCK cells of the invention support the replication of a cold-adapted, and/or temperature sensitive, and/or attenuated version of influenza strain B/Malaysia (i.e., ca B/Malaysia) to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In certain embodiments, the MDCK cells of the invention support the replication of a cold-adapted, and/or temperature sensitive, and/or attenuated version of influenza strain A/Vietnam (i.e., ca A/Vietnam) to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In certain embodiments, the MDCK cells of the invention support the replication of a cold-adapted, and/or temperature sensitive, and/or attenuated version of influenza strain A/Wisconsin (i.e., ca A/Wisconsin) to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8.

In certain embodiments, the MDCK cells of the invention support the replication of a cold-adapted, and/or temperature sensitive, and/or attenuated version of each of influenza strains A/New Calcdonia and A/Hiroshima to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In certain embodiments, the MDCK cells of the invention support the replication of a cold-adapted, and/or temperature sensitive, and/or attenuated version of each of influenza strains A/New Calcdonia and B/Malaysia to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In certain embodiments, the MDCK cells of the invention support the replication of a cold-adapted, and/or temperature sensitive, and/or attenuated version of each of influenza strains A/New Calcdonia and A/Vietnam to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8.

In certain embodiments, the MDCK cells of the invention support the replication of a cold-adapted, and/or temperature sensitive, and/or attenuated version of each of influenza strains A/Hiroshima and B/Malaysia to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In certain embodiments, the MDCK cells of the invention support the replication of a cold-adapted, and/or temperature sensitive, and/or attenuated version of each of influenza strains A/Hiroshima and A/Vietnam to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In certain embodiments, the MDCK cells of the invention support the replication of a cold-adapted, and/or temperature sensitive, and/or attenuated version of each of influenza strains B/Malaysia and A/Vietnam to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8.

In certain embodiments, the MDCK cells of the invention support the replication of a cold-adapted, and/or temperature sensitive, and/or attenuated version of each of influenza strains A/New Calcdonia, A/Hiroshima and B/Malaysia to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In certain embodiments, the MDCK cells of the invention support the replication of a cold-adapted, and/or temperature sensitive, and/or attenuated version of each of influenza strains A/New Calcdonia, A/Hiroshima and A/Vietnam to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In certain embodiments, the MDCK cells of the invention support the replication of a cold-adapted, and/or temperature sensitive, and/or attenuated version of each of influenza strains A/New Calcdonia, B/Malaysia and A/Vietnam to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In certain embodiments, the MDCK cells of the invention support the replication of a cold-adapted, and/or temperature sensitive, and/or attenuated version of each of influenza strains B/Malaysia, A/Hiroshima and A/Vietnam to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In certain embodiments, the MDCK cells of the invention support the replication of a cold-adapted, and/or temperature sensitive, and/or attenuated version of each of influenza strains A/New Calcdonia, A/Hiroshima, B/Malaysia and A/Vietnam to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8.

In yet another aspect, the invention provides a method for growing cold-adapted, and/or temperature sensitive, and/or attenuated influenza viruses to a $\log_{10}$ TCID$_{50}$/mL and/or a $\log_{10}$ FFU/mL of at least 8.2, or at least 8.4, or at least 8.6, or at least 8.8, or at least 9.0, or at least 9.2, or at least 9.4, or at least 9.6, or at least 9.8 or at least 10.0, comprising growing the cells in MediV105, M-32, MediV 107 or M18M or a growth optimized derivative thereof, prior to infection with the influenza viruses, then adding fresh media or media components (e.g., glucose, amino acids, lipids) during or post infection. In yet another aspect, the invention provides a method for growing cold-adapted, and/or temperature sensitive, and/or attenuated influenza viruses to a $\log_{10}$ TCID$_{50}$/mL and/or a $\log_{10}$ FFU/mL of at least 8.0, or at least 8.2, or at least 8.4, or at least 8.6, or at least 8.8, or at least 9.0, or at least 9.2, or at least 9.4, or at least 9.6, or at least 9.8 or at least 10.0, comprising growing the cells in a serum free medium, preferably an animal protein free medium and adding a protease e.g., TrypLE (1:10-1:100) prior to, during or after infecting the cells with influenza viruses. In certain embodiments, the cold-adapted, and/or temperature sensitive, and/or attenuated influenza viruses grow to a $\log_{10}$ TCID$_{50}$/mL and/or a $\log_{10}$ FFU/mL of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8 or at least 10.0. In certain embodiments, the fresh media is MediV 105 supplemented with a protease, e.g., TrypLE (1:10-1:100). In certain embodiments, the fresh media is M-32 supplemented with a protease, e.g., TrypLE (1:10-1:100). In certain embodiments, the fresh media is MediV 107 supplemented with a protease, e.g., TrypLE (1:10-1:100). Any protease known by one skilled in the art to be useful in cleaving influenza proteins can be used in these methods. In certain embodiments, the fresh media is M18M supplemented with a protease, e.g., TrypLE (1:10-1:100). In certain embodiments, the fresh media is DMEM/F12 supplemented with 4.5 g/L glucose, 4 mM glutamine, and a protease, e.g., TrypLE (1:10-1:100).

It will be understood by one of skill in the art that the cells of the invention can frequently be used as part of a cell culture composition. The components of a cell culture composition can vary according to the cells and intended use. For example, for cultivation purposes a cell culture composition may comprise cells of the invention and a suitable media for growth of the cells. Accordingly, the present invention provides cell culture compositions comprising cells of the invention and other components which can include, but are not limited to, media (e.g., a media disclosed herein), media components, buffers, chemical compounds, additional cell types, viral material (e.g., viral genomes, viral particles) and heterologous proteins. In one embodiment, a cell culture composition comprises cells of the invention and a media or components thereof. Media which may be present in a cell culture composition include serum-free media, serum containing media, and animal protein-free media. In one embodiment, a cell composition comprises a serum-free media, e.g., MediV 101, MediV 102, MediV 103, MediV 104, MediV 105, M-32, MediV 107 or M18M, or components or a growth optimized derivative thereof.

7.3 Methods and Media Formulations

The present invention further provides methods and media formulations for the cultivation of MDCK cells that support the replication of influenza viruses to high titer in serum containing media. The present invention further provides methods for the adaptation to and subsequent cultivation of the MDCK cells in serum-free media, including animal protein free media formulations. In certain aspects of the invention, the media are formulated such that the MDCK cells retain one or more of the following characteristics including but limited to, being non-tumorigenic, being non-oncogenic, growing as adherent cells, growing as non-adherent cells, having an epithelial-like morphology, supporting the replication of various viruses when cultured, and supporting the replication of influenza virus to high titer as described herein. It is contemplated that the media formulations disclosed herein or components thereof, may be present in a cell culture composition.

Serum containing media formulations are well known in the art. Serum containing media formulations include but are not limited to, Dulbecco's Modified Eagle Medium (DMEM)+Fetal Bovine Serum (FBS)+glutamine+glucose. In one embodiment, FBS is present in a serum containing media at a concentration between about 1% and about 20%, or between about 5% and about 15%, or between about 5% and about 10%. In a specific embodiment, FBS is present in a serum containing media at a concentration of 10%. In another embodiment, glutamine is present in a serum containing media at a concentration of between about 0.5 mM and about 10 mM, or between about 1 mM and 10 mM, or between about 2 mM and 5 mM. In a specific embodiment, glutamine is present in a serum containing media at a concentration of 4 mM. In still another embodiment, glucose is present in a serum containing media at a concentration of between about 1 g/L and about 10 g/L, or between about 2 g/L and about 5 g/L. In a specific embodiment, glucose is present in a serum containing media at a concentration of 4.5 g/L. In yet another embodiment, a serum containing media formulation comprises, FBS at a concentration between about 1% and about 20%, glutamine at a concentration of between about 0.5 mM and about 10 mM, and glucose a concentration of between about 1 g/L and about 10 g/L. In a specific embodiment, a serum containing media formulation comprises, Dulbecco's Modified Eagle Medium (DMEM)+10% Fetal Bovine Serum (FBS)+4 mM glutamine+4.5 g/L glucose. DMEM is readily available from numerous commercial sources including, for example, Gibco/BRL (Cat. No. 11965-084). FBS is readily available from numerous commercial sources including, for example, JRH Biosciences (Cat. No. 12107-500M). While FBS is the most commonly applied supplement in animal cell culture media, other serum sources are also routinely used and encompassed by the present invention, including newborn calf, horse and human.

In one embodiment, serum adapted MDCK cells of the invention are derived from Madin Darby Canine Kidney Cells (MDCK) cells obtained from the American type Culture Collection (ATCC CCL34) by culturing them in a chemically defined media supplemented with serum. In a specific embodiment, MDCK cells (ATCC CCL34) are expanded in a chemically defined media supplemented with serum to generate a serum adapted MDCK cell line as follows: the MDCK (ATCC CCL34) cells are passaged in Dulbecco's Modified Eagle Medium (DMEM) supplemented with fetal bovine serum (10% v/v), 4 mM glutamine and 4.5 g/L glucose to obtain sufficient cells to prepare a frozen pre Master Cell Bank (PreMCB). In another specific embodiment, the cells are cultured using the methods detailed in Examples 1 and 2, below. It is specifically contemplated that the MDCK serum-adapted cells are passaged for another 20 passages or more, from a vial of PreMCB and tested for tumorigenicity in an in vivo adult nude mice model and karyology in a karyotype assay. In certain embodiments, the expanded MDCK cells will not produce tumors when injected subcutaneously into adult nude mice and will have a modal chromosome number of 78 with a range of chromosome numbers of no more then about 60-88, or of no more then about 65-85, or of no more than about 65-80, or of no more then about 70-85. In one embodiment, the MDCK-S cells are non-tumorigenic after at least 20 passages, or after at least 30 passages, or after at least 40 passages, or after at least 50 passages, or after at least 60 passages, or after at least 70 passages, or after at least 80 passages, or after at least 90 passages, or after at least 100 passages in a medium (e.g., a media described herein).

It will be appreciated by one of skill in the art that the use of serum or animal extracts in tissue culture applications may have drawbacks (Lambert, K. J. et al., In: Animal Cell Biotechnology, Vol 1, Spier, R. E. et al., Eds., Academic Pres New York, pp. 85-122 (1985)). For example, the chemical composition of these supplements may vary between lots, even from a single manufacturer. In addition, supplements of animal or human origin may also be contaminated with adventitious agents (e.g., mycoplasma, viruses, and prions). These agents can seriously undermine the health of the cultured cells when these contaminated supplements are used in cell culture media formulations. Further, these agents may pose a health risk when substances produced in cultures contaminated with adventitious agents are used in cell therapy and other clinical applications. A major fear is the presence of prions which cause spongiform encephalopathies in animals and Creutzfeld-Jakob disease in humans. Accordingly, the present invention further provides serum-free media formulations comprising an MDCK cell of the invention.

Serum-free media formulations of the invention include, but are not limited to, MediV 101 (Taub's+Plant Hydrolysate), MediV 102 (Taub's+Lipids), MediV 103 (Taub's+Lipids+Plant Hydrolysate), MediV 104 (Taub's+Lipids+Plant Hydrolysate+growth factor), MediV 105 (same as MediV 104 except transferrin is replaced with Ferric ammonium citrate/Tropolone or Ferric ammonium sulfate/Tropolone) (see, for example, U.S. Patent Publication No. 2006/0188977), M-32 (same as MediV 105 supplemented with trace elements A, B and C (see Table 9), MediV 107 (see Table 10) and M18M (see Table 11). It is specifically contemplated that Taub's SF medium (Taub and Livingston, 1981, *Ann NY Acad. Sci.*, 372:406) is a 50:50 mixture of DMEM and Ham's F12 supplemented with hormones, 5 μg/mL insulin, 5 μg/mL transferrin, 25 ng/mL prostaglandin E1, 50 nM hydrocortisone, 5 pM triiodothyronine and 10 nM $Na_2SeO_3$, 4.5 g/L glucose, 2.2 g/L $NaHCO_3$ and 4 mM L-glutamine. Taub's SF medium is also referred to herein as Taub's medium or simply "Taub's". Specific media formulations and methods of preparing them are provide infra (see, e.g., Section 9.10).

Plant hydrolysates include but are not limited to, hydrolysates from one or more of the following: corn, cottonseed, pea, soy, malt, potato and wheat. Plant hydrolysates may be produced by enzymatic hydrolysis and generally contain a mix of peptides, free amino acids and growth factors. Plant hydrolysates are readily obtained from a number of commercial sources including, for example, Marcor Development, HyClone and Organo Technie. It is also contemplated that yeast hydrolysates my also be utilized instead of, or in combination with plant hydrolysates. Yeast hydrolysates are readily obtained from a number of commercial sources including, for example, Sigma-Aldrich, USB Corp, Gibco/BRL and others. In certain embodiments, synthetic hydrolysates can be used in addition or in place of plant or yeast hydrolysates.

Lipids that may be used to supplement culture media include but are not limited to chemically defined animal and plant derived lipid supplements as well as synthetically derived lipids. Lipids which may be present in a lipid supplement includes but is not limited to, cholesterol, saturated and/or unsaturated fatty acids (e.g., arachidonic, linoleic, linolenic, myristic, oleic, palmitic and stearic acids). Cholesterol may be present at concentrations between 0.10 mg/ml and 0.40 mg/ml in a 100× stock of lipid supplement. Fatty acids may be present in concentrations between 1 μg/ml and 20 μg/ml in a 100× stock of lipid supplement. Lipids suitable for media formulations are readily obtained from a number of commercial sources including, for example HyClone, Gibco/BRL and Sigma-Aldrich.

In one embodiment, Taub's media is supplemented with a plant hydrolysate and a final concentration of at least 0.5 g/L, or at least 1.0 g/L, or at least 1.5 g/L, or at least 2.0 g/L, or at least 2.5 g/L, or at least 3.0 g/L, or at least 5.0 g/L, or at least 10 g/L, or at least 20 g/L. In a specific embodiment, Taub's media is supplemented with a wheat hydrolysate. In another specific embodiment, Taub's media is supplemented with a wheat hydrolysate at a final concentration of 2.5 g/L. The present invention provides a serum-free media referred to herein as MediV 101 comprising Taub's media supplemented with a wheat hydrolysate at a final concentration of 2.5 g/L (see, e.g., Section 9.10).

In another embodiment, Taub's media is supplemented with a lipid mixture at a final concentration of at least 50%, or at least 60%, or at least 70%, or at least 80%, or at least 90%, or at least 100%, or at least 125%, or at least 150%, or at least 200%, or at least 300% of the manufacturers recommended final concentration. In a specific embodiment, Taub's media is supplemented with a chemically defined lipid mixture. In another specific embodiment, Taub's media is supplemented with a chemically defined lipid mixture at a final concentration of 100% of the manufacturers' recommended final concentration (e.g., a 100× stock obtained from a manufacture would be added to the media to a final concentration of 1×). The present invention provides a serum-free media referred to herein as MediV 102 comprising Taub's media supplemented with a chemically defined lipid mixture at a final concentration of 100% of the manufacturers recommended final concentration (see, e.g., Section 9.10).

In still another embodiment, Taub's media is supplemented with a plant hydrolysate at a final concentration of at least 0.5 g/L, or at least 1.0 g/L, or at least 1.5 g/L, or at least 2.0 g/L, or at least 2.5 g/L, or at least 3.0 g/L, or at least 5.0 g/L, or at least 10 g/L, or at least 20 g/L and with a lipid mixture at a final concentration of at least 50%, or at least 60%, or at least 70%, or at least 80%, or at least 90%, or at least 100%, or at least 125%, or at least 150%, or at least 175%, or at least 200% of the manufacturers recommended concentration. In a specific embodiment, Taub's media is supplemented with wheat hydrolysate and a chemically defined lipid mixture. In another specific embodiment, Taub's media is supplemented with a wheat hydrolysate at a final concentration of 2.5 g/L and a chemically defined lipid mixture at a final concentration of 100% of the manufacturers recommended final concentration. The present invention provides a serum-free media referred to herein as MediV 103 comprising Taub's media supplemented with a wheat hydrolysate at a final concentration of 2.5 g/L and a chemically defined lipid mixture at a final concentration of 100% of the manufacturers recommended final concentration (see, e.g., Section 9.10).

In yet another embodiment, Taub's media is supplemented with a growth hormone. Growth hormones which may be used include but are not limited to, Epidermal Growth Factor (EGF), Insulin Growth Factor (IGF), Transforming Growth Factor (TGF) and Fibroblast Growth Factor (FGF). In a particular embodiment, the growth hormone is Epidermal Growth Factor (EGF). In one embodiment, Taub's media is supplemented with a growth factor at a final concentration of between about 0.1 to about 50.0 ng/ml, or between about 0.5 to about 25.0 ng/ml, or between about 1.0 to about 20 ng/ml, or between about 5.0 to about 15.0 ng/ml, or between about 8 ng/ml to about 12 ng/ml. In a specific embodiment, Taub's media is supplemented with a EGF at a final concentration of about 10 ng/ml. In still other embodiments, Taub's media is supplemented with a growth factor at a final concentration of between about 0.1 to about 50.0 ng/ml, or between about 0.5 to about 25.0 ng/ml, or between about 1.0 to about 20 ng/ml, or between about 5.0 to about 15.0 ng/ml, or between about 8 ng/ml to about 12 ng/ml and with a plant hydrolysate at a final concentration of at least 0.5 g/L, or at least 1.0 g/L, or at least 1.5 g/L, or at least 2.0 g/L, or at least 2.5 g/L, or at least 3.0 g/L, or at least 5.0 g/L, or at least 10 g/L, or at least 20 g/L and with a lipid mixture at a final concentration of at least 50%, or at least 60%, or at least 70%, or at least 80%, or at least 90%, or at least 100%, or at least 125%, or at least 150%, or at least 175%, or at least 200% of the manufacturers recommended concentration. In another specific embodiment, Taub's media is supplemented with a wheat hydrolysate at a final concentration of 2.5 g/L and a chemically defined lipid mixture at a final concentration of 100% of the manufacturers recommended final concentration and EGF at a final concentration of about 10 ng/ml. The present invention provides a serum-free media referred to herein as MediV 104 comprising Taub's media supplemented with a wheat hydrolysate at a final concentration of 2.5 g/L and a chemically defined lipid mixture at a final concentration of 100% of the manufacturers recommended final concentration and EGF at a final concentration of about 10 ng/ml (see, e.g., Section 9.10).

It will also be appreciated by one skilled in the art that animal protein-free media formulations may be desirable for the production of virus used in the manufacture of vaccines. Accordingly, in certain embodiments one or more or all of the animal derived components of the serum-free media disclosed herein (e.g., MediV 101, MediV 102, MediV 103, MediV 104, MediV 105, M-32, MediV 107, M18M) can be replaced by an animal-free derivative. For example, commercially available recombinant insulin derived from non-animal sources (e.g., Biological Industries Cat. No. 01-818-1) may utilized instead of insulin derived from an animal source. Likewise, iron binding agents (see, e.g., U.S. Pat. Nos. 5,045, 454; 5,118,513; 6,593,140; and PCT publication number WO 01/16294) may be utilized instead of transferrin derived from an animal source. In one embodiment, serum-free media formulations of the invention comprise tropolone (2-hydroxy-2,4,6-cyclohepatrien-1) and a source of iron (e.g., ferric ammonium citrate, ferric ammonium sulfate) instead of transferrin. For example, tropolone or a tropolone derivative will be present in an excess molar concentration to the iron present in the medium for at a molar ratio of about 2 to 1 to about 70 to 1, or of about 10 to 1 to about 70 to 1 In a specific embodiment, a serum-free media of the present invention comprises Ferric ammonium citrate at a final concentration of 200 µg/L and Tropolone at a final concentration of 250 µg/L (see, e.g., Section 9.10). Accordingly, where the iron concentration in the medium is around 0.3 µM, the tropolone or derivative thereof may be employed at a concentration of about 1.5 µM to about 20 µM, e.g. about 3 µM to about 20 µM. The iron may be present as ferrous or ferric ions, for example resulting from the use of simple or complex iron salts in the medium such as ferrous sulfate, ferric chloride, ferric nitrate or in particular ferric ammonium citrate. The present invention provides a serum-free media referred to herein as MediV 105 comprising Taub's media without transferrin supplemented with a wheat hydrolysate at a final concentration of 2.5 g/L and a chemically defined lipid mixture at a final concentration of 100% of the manufacturers recommended final concentration and EGF at a final concentration of about 10 ng/ml and Ferric ammonium citrate:Tropolone or Ferric ammonium sulfate: Tropolone at a ratio of between 2 to 1 and 70 to 1. In a specific embodiment, a serum-free media of the present invention comprises Ferric ammonium citrate at a final concentration of 200 µg/L and Tropolone at a final concentration of 250 µg/L (see, e.g., Section 9.10).

In certain embodiments, one or more of the media disclosed herein are supplemented with trace elements (e.g., Trace Element Solutions A, B and C, Table 9). Trace elements which may be used include but are not limited to, $CuSO_4.5H_2O$, $ZnSO_4.7H_2O$, Selenite.2Na, Ferric citrate, $MnSO_4.H_2O$, $Na_2SiO_3.9H_2O$, Molybdic acid-Ammonium salt, $NH_4VO_3$, $NiSO_4.6H_2O$, $SnCl_2$ (anhydrous), $AlCl_3.6H_2O$, $AgNO_3$, $Ba(C_2H_3O_2)_2$, KBr, $CdCl_2$, $CoCl_2.6H_2O$, $CrCl_3$ (anhydrous), NaF, $GeO_2$, KI, RbCl, $ZrOCl_2.8H_2O$. Concentrated stock solutions of trace elements are readily obtained from a number of commercial sources including, for example Cell Grow (see Catalog Nos. 99-182, 99-175 and 99-176). The present invention provides a serum-free media referred to herein as M-32 comprising Taub's media without transferrin supplemented with a wheat hydrolysate at a final concentration of 2.5 g/L and a chemically defined lipid mixture at a final concentration of 100% of the manufacturers recommended final concentration and EGF at a final concentration of about 10 ng/ml and Trace Element Solutions A, B and C (Table 9), and Ferric ammonium citrate:Tropolone or Ferric ammonium sulfate:Tropolone at a ratio of between 2 to 1 and 70 to 1. In a specific embodiment, a serum-free media of the present invention comprises Ferric ammonium citrate at a final concentration of 200 μg/L and Tropolone at a final concentration of 250 μg/L) (see, e.g., Section 9.10). It is also contemplated that one or more of the media disclosed herein are supplemented with additional glucose. In one embodiment, a serum free media of the present invention comprises an additional 1-5 g/L of glucose for a final glucose concentration of between about 4.5 to about 10 g/L.

In one embodiment, MDCK cells adapted for growth in MediV 101, MediV 102, MediV 103, MediV 104, MediV 105, M-32, MediV 107 or M18M serum-free media are derived from Madin Darby Canine Kidney Cells (MDCK) cells obtained from the American type Culture Collection (ATCC CCL34) by culturing in a chemically defined media supplemented with serum for at least one passage and then passaging them in a serum-free media such as, for example, the serum-free medias described supra. In a specific embodiment, MDCK cells (ATCC CCL34) are adapted to serum-free media as follows: The MDCK (ATCC CCL34) cells are passaged in Dulbecco's Modified Eagle Medium (DMEM) supplemented with fetal bovine serum (10% v/v), 4 mM glutamine and 4.5 g/L glucose at least once and then passaged in serum-free media. The MDCK cells are then passaged as needed in serum-free media to obtain enough serum-free media-adapted cells to prepare a frozen pre Master Cell Bank (PreMCB). In certain embodiments, the cells are passaged in a serum containing media (e.g., Dulbecco's Modified Eagle Medium (DMEM) supplemented with fetal bovine serum (10% v/v), 4 mM glutamine and 4.5 g/L glucose) between 1 and 5 times, or between 4 and 10 time, or between 9 and 20 times, or more than 20 times, and then passaged in serum-free media (e.g., MediV 101, MediV 102, MediV 103, MediV 104, MediV 105, M-32, MediV 107 and M18M, see, e.g., Section 9.10).

It is specifically contemplated that the serum-free media-adapted MDCK cells are passaged for another 20 passages or more, from a vial of PreMCB and tested for tumorigenicity in an vivo adult nude mice model and karyology in a karyotype assay. In certain embodiments, the expanded serum-free media-adapted MDCK cells will not produce nodules when injected subcutaneously into adult nude mice and/or will have a modal chromosome number of 78. In another embodiment, the expanded serum-free media-adapted MDCK cells will have a modal chromosome number of 78 with a range of chromosome numbers of no more then about 60 to about 88, or of no more then about 65 to about 85, or of no more then about 65-80, or of no more then about 70 to about 85. In one embodiment, the MDCK-SF cells are non-tumorigenic after at least 20 passages, or after at least 30 passages, or after at least 40 passages, or after at least 50 passages, or after at least 60 passages, or after at least 70 passages, or after at least 80 passages, or after at least 90 passages, or after at least 100 passages in a medium (e.g., a media described herein).

In one embodiment, the serum-free media used for the derivation of serum-free media-adapted MDCK cells is MediV 101. In another embodiment, the serum-free media used for the derivation of serum-free media-adapted MDCK cells is MediV 102. In yet another embodiment, the serum-free media used for the derivation of serum-free media-adapted MDCK cells is MediV 103. In still another embodiment, the serum-free media used for the derivation of serum-free media-adapted MDCK cells is MediV-104. In another embodiment, the serum-free media used for the derivation of serum-free media-adapted MDCK cells is MediV 105. In other embodiments, the serum-free media used for the derivation of serum-free media-adapted MDCK cells is M-32. In other embodiments, the serum-free media used for the derivation of serum-free media-adapted MDCK cells is MediV 107. In another embodiment, the serum-free media used for the derivation of serum-free media-adapted MDCK cells is M18M. In yet another embodiment, the serum-free media used for the derivation of serum-free media-adapted MDCK cells is an APF media. It is contemplated that the media described herein may be formulated to eliminate animal proteins. For example bovine transferrin may be replaced with a recombinant transferrin derived from a non animal source. Specific media formulations and methods of preparing them are provided infra (see, e.g., Section 9.10).

In another embodiment, the cells of the invention are not adapted for growth in a serum-free media, but rather are simply grown in serum free medium without adaptation. Thus, in one embodiment, the cells are grown in MediV 101. In another embodiment, the cells are grown in MediV 102. In yet another embodiment, the cells are grown in MediV 103. In still another embodiment, the cells are grown in MediV-104. In another embodiment, the cells are grown in MediV 105. In another embodiment, the cells are grown in M-32. In another embodiment, the cells are grown in MediV 107. In another embodiment, the cells are grown in M18M. In yet another embodiment, the cells are grown in an APF media. It is contemplated that the media described herein may be formulated to eliminate animal proteins. For example bovine transferrin may be replaced with a recombinant transferrin derived from a non animal source

7.4 Culture Conditions

The present invention provides methods for the cultivation of MDCK cells of the invention and other animal cells in serum containing and serum-free media formulations as set forth above. It is specifically contemplated that additional culture conditions may play a role in the maintenance of the properties of the MDCK cells of the invention, including being non-tumorigenic, being non-oncogenic, growing as adherent cells, growing as non-adherent cells, having an epithelial-like morphology, supporting the replication of various viruses, and supporting the growth of influenza viruses (e.g., cold-adapted, and/or temperature sensitive, and/or attenuated) to high titer, e.g., a $\log_{10}$ $TCID_{50}$/mL and/or a $\log_{10}$ FFU/mL of at least about 7.4, or at least about 7.6, or at least about 7.8, or at least about 8.0, or at least about 9.0. These culture conditions include, but are not limited to, the choice of adherent surface, cell density, temperature, $CO_2$ concentration, method of cultivation, dissolved oxygen content and pH.

It is specifically contemplated that one skilled in the art may adapt the culture conditions in a number of ways to optimize the growth of the MDCK cells of the invention. Such adaptations may also result in a increase in the production of viral material (e.g., virus), as described, for example, in US Patent Application Publication No. 2005/0118698. Alternatively, one skilled in the art may adapt the culture conditions to optimize the production of vaccine material from the MDCK cells of the invention without regard for the growth of the cells. These culture conditions include but are not limited to adherent surface, cell density, temperature, $CO_2$ concentration, method of cultivation, dissolved oxygen content and pH.

In one embodiment, the MDCK cells of the invention are cultivated as adherent cells on a surface to which they attach. Adherent surfaces on which tissue culture cells can be grown on are well known in the art. Adherent surfaces include but are not limited to, surface modified polystyrene plastics, protein coated surfaces (e.g., fibronectin and/or collagen coated glass/plastic) as well as a large variety of commercially available microcarriers (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor; Cytodex 1 and Cytodex 3, GE Healthcare Life Science). Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. The choice of adherent surface is determined by the methods utilized for the cultivation of the MDCK cells of the invention and can be determined by one skilled in the art. It will be understood by one of skill in the art that during the process of subculturing adherent cells (i.e., proliferating the cells, expanding the cell culture) the cells must be transferred from a confluent support surface (e.g., flask surface, microcarrier, etc) onto a new support surface. A number of methods can be utilized to effect such cell transfer. For example, proteases, including trypsin, TrypLE and collagenase, may be used to remove cells from flasks or microcarriers the cells are then washed and diluted into a larger flask or into a larger volume of microcarrier containing media for expansion. It is preferable to use a non-animal derived protease for such applications such as, TrypLE (Invitrogen, Carlsbad, Calif.). Alternatively, in microcarrier cultures direct bead to bead transfer methods may be utilized, wherein fresh beads and media are mixed with the confluent beads and the culture is incubated under conditions which facilitate the transfer of cells to the new beads. In certain embodiments, a combination of protease treatment and bead to bead transfer is utilized. In a specific embodiment, a cell culture of MDCK cells of the invention growing as adherent cells on microcarriers are treated with a protease (e.g., TrypLE), the protease is then inactivated (e.g., by the addition of a protease inhibitor such as lima bean trypsin inhibitor), fresh media and microcarrier beads may then be added to the culture. In one embodiment, a portion or all of the growth medium is removed prior to protease treatment. In another embodiment, a portion or all of the growth medium is replaced with a buffer prior to protease treatment. In still another embodiment, a chelating agent is added prior to or during protease treatment. In some embodiments, the protease treated culture is transferred to a larger culture vessel before, during or after the addition of fresh media and microcarriers.

In one embodiment, the MDCK cells of the invention are cultivated as non-adherent cells (e.g., capable of growth under non-adherent conditions) in suspension. Suitable culture vessels which can be employed in the course of the process according to the invention are all vessels known to the person skilled in the art, such as, for example, spinner bottles, roller bottles, fermenters or bioreactors. For commercial production of viruses, e.g., for vaccine production, it is often desirable to culture the cells in a bioreactor or fermenter. Bioreactors are available in volumes from under 1 liter to in excess of 10,000 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

In one embodiment, the MDCK cells of the invention are cultivated as adherent cells in a batch culture system. In a specific embodiment, the MDCK cells of the invention are cultivated as adherent cells in a fed batch culture system wherein additional nutrients (e.g., carbon source, amino acids, etc) are added as they are depleted from the starting media to facilitate growth to high cell densities. In still another embodiment, the MDCK cells of the invention are cultivated as adherent cells in a perfusion culture system. It is specifically contemplated that the MDCK cells of the invention will be cultured in a perfusion system, (e.g., in a stirred vessel fermenter, using cell retention systems known to the person skilled in the art, such as, for example, centrifugation, filtration, spin filters and the like) for the production of vaccine material (e.g., virus). Additional guidance regarding culture of MDCK cells as adherent cells may be found, for example, in US Patent Application Publication Nos. 2003/0108860 and 2005/0118140. In another embodiment, the MDCK cells of the invention are cultivated as non-adherent cells in a batch or fed batch culture system. In still another embodiment, the MDCK cells of the invention are cultivated as non-adherent cells in a perfusion culture system.

In certain embodiments, a reactor system comprising disposable elements such as a flexible plastic bag for culturing cells is utilized. Such reactor systems are known in the art and are available commercially. See for example International Patent Publications WO 05/108546; WO 05/104706; and WO 05/10849 and Section 9.12 infra. Reactor systems comprising disposable elements (also referred herein as "single use bioreactor(s)" or by the abbreviation "SUB(s)") may be pre-sterilized and do not require a steam-in-place (SIP) or clean-in-place (CIP) environment for changing from batch to batch or product to product in a culture or production system. As such, SUBs require less regulatory control by assuring zero batch-to-batch I contamination and can, thus, be operated at a considerable cost-advantage and with minimal or no preparation prior to use. Additionally, since SUBs do not require cleaning or sterilizing they can be rapidly deployed to facilitate production of large quantities of vaccine material (e.g., virus) from cell culture. In particular embodiments, a disposable reactor system is a stirred-tank reactor system which allows for a hydrodynamic environment for mixing the cell culture which allows for more efficient nutrient, $O_2$ and pH control.

In one embodiment, the MDCK cells of the invention are cultivated at a $CO_2$ concentration of at least 1%, or of at least 2%, or of at least 3%, or of at least 4%, or of at least 5%, or of at least 6%, or of at least 7%, or of at least 8%, or of at least 9%, or of at least 10%, or of at least 20%.

In one embodiment the dissolved oxygen (DO) concentration ($pO_2$ value) is advantageously regulated during the cultivation of the MDCK cells of the invention and is in the range from 5% and 95% (based on the air saturation), or between 10% and 60%. In a specific embodiment the dissolved oxygen (DO) concentration ($pO_2$ value) is at least 10%, or at least 20%, or at least 30%, or at least 50%, or at least 60%.

In another embodiment, the pH of the culture medium used for the cultivation of the MDCK cells of the invention is regulated during culturing and is in the range from pH 6.4 to pH 8.0, or in the range from pH 6.8 to pH 7.4. In a specific embodiment, the pH of the culture medium is at about 6.4, or at about 6.6, or at about 6.8, or at about 7.0, or at about 7.2, or at about 7.4, or at about 7.6, or at about 7.8, or at least 8.0.

In a further embodiment, the MDCK cells of the invention are cultured at a temperature of 25° C. to 39° C. It is specifically contemplated that the culture temperature may be varied depending on the process desired. For example, the MDCK cells of the invention may be grown at 37° C. for proliferation of the cells and at a lower temperature (e.g., 25° C. to 35° C.) of for the production of vaccine material (e.g., virus). In another embodiment, the cells are cultured at a temperature of less than 30° C., or of less than 31° C., or of less than 32° C., or of less than 33° C., or of less than 34° C. for the production of vaccine material. In another embodiment, the cells are cultured at a temperature of 30° C., or 31° C., or 32° C., or 33° C., or 34° C. for the production of vaccine material.

In order to generate vaccine material (e.g., virus) it is specifically contemplated that the MDCK cells of the invention are cultured such that the medium can be readily exchanged (e.g., a perfusion system). The cells may be cultured to a very high cell density, for example to between $1 \times 10^6$ and $25 \times 10^6$ cells/mL. The content of glucose, glutamine, lactate, as well as the pH and $pO_2$ value in the medium and other parameters, such as agitation, known to the person skilled in the art can be readily manipulated during culture of the MDCK cells of the invention such that the cell density and/or virus production can be optimized.

The present invention provides methods for proliferating cells (e.g., MDCK cells of the present invention) in culture to high cell density by culturing said cells in a SUB. In certain embodiments, MDCK cells are cultured in a SUB system to a cell density of at least $5 \times 10^5$ cells/mL, a least $7.5 \times 10^5$ cells/mL, at least $1 \times 10^6$ cells/mL, at least $2.5 \times 10^6$ cells/mL, at least $5 \times 10^6$ cells/mL, at least $7.5 \times 10^6$ cells/mL, at least $10 \times 10^6$, at least $15 \times 10^6$ cells/mL, at least $20 \times 10^6$ cells/mL, or at least $25 \times 10^6$ cells/mL. In a specific embodiment, MDCK cells are cultured in a SUB a serum-free medium such as those described infra (see, for e.g., Section 9.10) that has be supplemented with additional glucose. For example, MediV-105 supplemented with an additional 4.5 g/L of glucose (9.0 g/L total glucose concentration) can be utilized. In yet another specific embodiment, MDCK cells are cultured in a SUB as adherent cells on a microcarrier. In one embodiment, the microcarrier is used at a concentration of between about 1 to about 4 g/L. In another embodiment, the microcarrier is used at a concentration of between about 2 to about 3 g/L. In certain embodiments the SUB is seeded with the MDCK cells to be cultured at a seeding density of about 5 to about $15 \times 10^4$ cells/mL. In a specific embodiment, the seeding density is between about 6 to about $14 \times 10^4$ cells/mL, or between about 7 to about $13 \times 10^4$ cells/mL, or between about 8 to about $12 \times 10^4$ cells/mL, or between about 9 to about $11 \times 10^4$ cells/mL. It will be apparent to one of skill in the art that the seeding density can also be calculated on a per microcarrier basis. Accordingly, in certain embodiments the SUB is seeded with the MDCK cells to be cultured at a seeding density of about 2 to about 30 cells/microcarrier, or of about 2 to about 25 cells/microcarrier, cells/microcarrier, or of about 2 to about 20 cells/microcarrier, or of about 2 to about 15 cells/microcarrier, or of about 2 to about 10 cells/microcarrier, or of about 5 to about 30 cells/microcarrier, or of about 10 to about 30 cells/microcarrier, or of about 15 to about 30 cells/microcarrier, or of about 20 to about 30, cells/microcarrier, or of about 5 to about 30 cells/microcarrier, or of about 10 to about 25 cells/microcarrier, or of about 15 to about 20 cells/microcarrier.

In certain embodiments, MDCK cells are cultured in a stirred-tank SUB in one or more parameters selected from the group consisting of temperature, agitation rate, pH, dissolved oxygen (DO), $O_2$ and $CO_2$ flow rate, are monitored and/or controlled. In one embodiment, the temperature is maintained at between about 30° C. to about 42° C., or between about 33° C. to about 39° C., or between about 35° C. to about 38° C. In a specific embodiment, the temperature is maintained at about between about 36° C. to about 37° C. In one embodiment, the agitation rate is maintained at between about 50 to 150 rpm. In a specific embodiment the rate of agitation is maintained at between about 80 to about 120 rpm, or between about 90 to about 100 rpm. Agitation rates are controlled by means well known in the art. In another embodiment, the pH of the culture is maintained at between about 6.0 to about 7.5. In a specific embodiment the pH of the starting culture is between about 6.0 to about 7.5 and the pH of the culture is maintained at about 7.0 to about 7.5 during the culture process. It will be understood by one of skill in the art that the initial pH may be lower or higher then the desired range and that the pH may be allowed to increase or decrease to the desired level (e.g., 7.4) where it is maintained. The pH is maintained by any method known in the art. For example the pH may be controlled by sparging $CO_2$ and/or by adding acid (e.g., HCL) or base (e.g., NaOH) as needed. In still another embodiment the acceptable range for the DO is between about 100 to about 35%. In a specific embodiment, the DO is maintained at between about 35% to about 50%, or at about 50%. In another specific embodiment, the DO should not drop below about 35%. It will be understood by one of skill in the art that the initial DO may be 100% and that the DO may be allowed to drop down to a predetermined level (e.g., 50%) where it is maintained. The DO is maintained used any method known in the art, such as, for example, by sparging $O_2$. In certain embodiments, the $O_2$ flow rate is maintained at less then about 2.0 L/min. In certain embodiments, the $CO_2$ flow rate is maintained at less then about 0.4 L/min.

7.5 Production of Vaccine Material (e.g., Virus)

The present invention provides a method for the production of viruses in cell culture in which MDCK cells are used to produce viruses. In certain embodiments of the method, the MDCK cells of the invention are used to produce viruses. In one embodiment the process comprises the following steps:

a. infecting a cell culture composition comprising an MDCK cell of the invention with a virus,
b. incubating the cell culture composition under conditions that permit replication of the virus; and
c. isolating viruses from the cell culture composition.

In one embodiment the MDCK cells of the invention are proliferated prior to step (a) as adherent cells. In another embodiment, the MDCK cells of the invention are proliferated prior to step (a) as non-adherent cells. The MDCK cells of the invention can be cultured in the course of the process in any media including, but not limited to, those described supra. In certain embodiments, the MDCK cells of the invention are cultured in the course of the process in a serum-free medium such as, for example, MediV-101, MediV-102, MediV-103, MediV-104, MediV-105, MediV-107, M18M and APF formulations thereof. In a specific embodiment, the MDCK cells of the invention are cultured in a serum-free medium supplemented with glucose. Optionally, the MDCK cells of the invention can be cultured in the course of the process in a serum containing media (e.g., DMEM+10% FBS+4 mM glutamine+4.5 g/L glucose). Additional culture conditions such as, for example, temperature, pH, $pO_2$, $CO_2$ concentration, and cell density are described in detail supra. One skilled in the art can establish a combination of culture conditions for the proliferation of the MDCK cells of the invention for the production of virus.

The temperature for the proliferation of the cells before infection with viruses is in one embodiment between 22° C. and 40° C. In certain embodiments, the temperature for the proliferation of the cells before infection with viruses is less then 39° C., or less than 38° C., or less than 37° C., or less than 36° C., or less than 35° C., or less than 34° C., or less than 33° C., or less than 32° C., or less than 30° C., or less than 28° C., or less than 26° C., or less than 24° C. In a specific embodiment, the temperature for the proliferation of the cells before infection with viruses is between about 33° C. to about 39° C. Culturing for proliferation of the cells can be carried out in one embodiment of the method in a perfusion system, e.g. in a stirred vessel fermenter, using cell retention systems known to the person skilled in the art, such as, for example, centrifugation, filtration, spin filters, microcarriers, and the like. In a specific embodiment, culturing for proliferation of the cells is carried out in a SUB system.

In such embodiments, the cells can, for example, be in this case proliferated for 1 to 20 days, or for 3 to 11 days. Exchange of the medium is carried out in the course of this, increasing from 0 to approximately 1 to 5 fermenter volumes per day. Alternatively, the growth medium is supplemented with and/or comprises additional components (e.g., glucose, trace mineral, amino acids, etc) such that media exchange is not required. The cells can be proliferated up to high cell densities in this manner, for example up to at least $1 \times 10^6$–$25 \times 10^6$ cells/mL. The perfusion rates during culture in the perfusion system can be regulated via the cell count, the content of glucose, glutamine or lactate in the medium and via other parameters known to the person skilled in the art. Alternatively, the cells can be cultured in a batch process or fed batch process.

In one embodiment of the process according to the invention, the pH, $pO_2$ value, glucose concentration and other parameters of the culture medium to culture the cells are regulated during culturing as described above using methods known to the person skilled in the art.

In certain embodiments, a portion of the medium is exchanged prior to step (a). In one embodiment, the portion of the medium to be exchanged is between about 20% to about 100%, or between about 30% to about 80%, or between about 30% to about 60%, or between about 66% to about 80%. In one embodiment, the medium is exchange with an equal volume of medium. In another embodiment, the medium is exchange with a reduced volume of medium, effectively concentrating the cells. The medium may be exchanged for a medium having the same or different composition. In one embodiment, a growth medium used for proliferation of the MDCK cells is exchange for an infection medium (i.e., a medium used during infection and viral replication). In a specific embodiment, the MDCK cells are proliferated in MediV-105, MediV-107 or M18M and prior to infection a portion of the medium is exchanged for an infection medium. Alternatively, the growth medium is supplemented with and/or comprises additional components (e.g., glucose, trace mineral, amino acids, etc) such that media exchange is not required. In another specific embodiment, the infection medium comprises a serine protease (e.g., trypsin, TrypLE, etc). In other embodiments where the media is not exchanged, a serine protease (e.g., trypsin, TrypLE, etc) is added shortly before, during or shortly after infection.

In certain embodiments, a protease is added prior to or at the same time as the cells are infected with virus.

In some embodiments, the infection of the cells with virus is carried out at an m.o.i. (multiplicity of infection, also abbreviated herein as "MOI") of about 0.00001 to about 10, or about 0.00001 to about 1, or about 0.00001 to about 0.0003, or about 0.00001 to about 0.0001, or about 0.0001 to about 10, or about 0.0005 to about 5, or about 0.002 to about 0.5, or about 0.001 to about 0.003. In still another embodiment, the infection of the cells with virus is carried out at an m.o.i. (multiplicity of infection) of 0.0001 to 10, or 0.0005 to 5, or 0.002 to 0.5 or 0.001 to 0.003. Alternatively, to the infection of cells with virus is determined by the final concentration of virus in the culture. For example, virus may be added at a final concentration of about $0.001 \times 10^3$/mL to about $0.2 \times 10^3$/mL, or about $0.01 \times 10^3$/mL to about $2 \times 10^3$/mL, or about $0.1 \times 10^3$/mL to about $20 \times 10^3$/mL, or about $1 \times 10^3$/mL to about $4 \times 10^3$/mL. After infection, the infected cell culture is cultured further to replicate the viruses, in particular until a maximum cytopathic effect or a maximum amount of virus antigen can be detected. In one embodiment, after infection the cells are cultured at a temperature of between 22° C. and 40° C. In certain embodiments, after infection with viruses the cells are cultured at a temperature of less then 39° C., or less than 38° C., or less than 37° C., or less than 36° C., or less than 35° C., or less than 34° C., or less than 33° C., or less than 32° C., or less than 30° C., or less than 28° C., or less than 26° C., or less than 24° C. In certain embodiments, after infection with viruses the cells are cultured at a temperature of 33° C. In another embodiment, after infection the cells are cultured at a temperature of less than 33° C. In still another embodiment, after infection the cells are cultured at a temperature of 31° C. In certain embodiments, the culturing of the cells is carried out for 2 to 10 days. The culturing can be carried out in the perfusion system or optionally in the batch process or fed batch process.

In such embodiments, the cells can, for example, be cultured after infection with viruses (step (b)) such that the pH and $pO_2$ value are maintained as described above. During the culturing of the cells prior to step (a) and/or virus replication according to step (b) of the process, a substitution of the cell culture medium with freshly prepared medium, medium concentrate or with defined constituents such as amino acids, vitamins, lipid fractions, phosphates etc. for optimizing the antigen yield is also possible. The cells can either be slowly diluted by further addition of medium or medium concentrate over several days or can be incubated during further perfusion with medium or medium concentrate. The perfusion rates can in this case in turn be regulated by means of the cell count, the content of glucose, glutamine, lactate or lactate dehydrogenase in the medium or other parameters known to the person skilled in the art. A combination of the perfusion system with a fed-batch process is further possible.

In one embodiment of the process, the harvesting and isolation of the produced viruses (step (c)) is carried out after a sufficient period to produce suitable yields of virus, such as 2 to 10 days, or optionally 3 to 7 days, after infection. In one embodiment of the process, the harvesting and isolation of the produced viruses (step (c)) is carried out 2 days, or 3 days, or 4 days, or 5 days, or after 6 days, or 7 days, or 8 days, or 9 days, or 10 days, after infection.

Viruses which may be produced in the MDCK cells of the present invention include but are not limited to, animal viruses, including families of Orthomyxoviridae, Paramyxoviridae, Togaviridae, Herpesviridae, Rhabdoviridae, Retroviridae, Reoviridae, Flaviviridae, Adenoviridae, Picornaviridae, Arenaviridae and Poxviridae.

Systems for producing influenza viruses in cell culture have also been developed in recent years (See, e.g., Furminger. in *Textbook of Influenza*, ed Nicholson, Webster and Hay, pp. 324-332, Blackwell Science (1998); Merten et al. in *Novel Strategies in The Design and Production of Vaccines*, ed Cohen & Shafferman, pp. 141-151, Kluwer Academic (1996)). Typically, these methods involve the infection of suitable host cells with a selected strain of virus. While eliminating many of the difficulties related to vaccine production in hen's eggs, not all pathogenic strains of influenza grow well and can be produced according to established tissue culture methods. In addition, many strains with desirable characteristics, e.g., attenuation, temperature sensitivity and cold adaptation, suitable for production of live attenuated vaccines, have not been successfully grown, especially at commercial scale, in tissue culture using established methods.

The present invention provides MDCK cell lines which have been adapted to grow in either serum containing or serum-free medias and which are capable of supporting the replication of viruses, including, but not limited to, influenza, when cultured. These cells lines are suitable for the economical replication of viruses in cell culture for use as vaccine material. The MDCK cells of the present invention are particularly useful for the production of cold adapted, temperature sensitive (ca/ts) strains of influenza (e.g., the influenza strains found in FluMist®) which do not grow well using other established cell lines. Further, the MDCK cells of the present invention are useful for the production of strains of influenza which may not grow in embryonated eggs such as avian influenza viruses which can also cause disease in humans (e.g., a "pandemic" strain).

Influenza viruses which may be produced by the process of the invention in the MDCK cells of the invention include but are not limited to, reassortant viruses that incorporate selected hemagglutinin and/or neuraminidase antigens in the context of an attenuated, temperature sensitive, cold adapted (ca/ts/att) master strain. For example, viruses can comprise the backbones (or one or more vRNA segment) of master strains that are one or more of, e.g., temperature-sensitive (ts), cold-adapted (ca), or an attenuated (att) (e.g., A/Ann Arbor/6/60, B/Ann Arbor/1/66, PR8, B/Leningrad/14/17/55, B/14/5/1, B/USSR/60/69, B/Leningrad/179/86, B/Leningrad/14/55, B/England/2608/76 etc.). Methods for the production of reassortant influenza vaccine strains in either eggs or cell lines are known in the art and include, for example, Kilbourne, E. D. in *Vaccines* ($2^{nd}$ Edition), ed. Plotkin and Mortimer, WB Saunders Co. (1988) and those disclosed in PCT Application PCT Patent Publication Nos. WO 05/062820 and WO 03/091401, and in U.S. Pat. Nos. 6,951,754, 6,887,699, 6,649,372, 6,544,785, 6,001,634, 5,854,037, 5,824,536, 5,840,520, 5,820,871, 5,786,199, and 5,166,057 and U.S. Patent Application Publication Nos. 20060019350, 20050158342, 20050037487, 20050266026, 20050186563, 20050221489, 20050032043, 20040142003, 20030035814, and 20020164770. Other influenza viruses which may be produced by the process of the invention in the MDCK cells of the invention include recombinant influenza viruses which may express a heterologous gene product, see for example, U.S. Patent Publication Nos. 2004/0241139 and 2004/0253273.

In one embodiment, the cells are proliferated, and the cells are then infected with influenza viruses. In certain embodiments, the infection is carried out at an m.o.i. (multiplicity of infection) of 0.0001 to 10, or of 0.0005 to 5, or of 0.002 to 0.5 or of 0.0001 to 0.002 or of 0.00001 to 0.002. In other embodiments, the infection is carried out at an m.o.i. (multiplicity of infection) of about 0.0001 to about 10, or of about 0.0005 to about 5, or of about 0.002 to about 0.5, or of about or of 0.0001 to about 0.002 or of about 0.00001 to about 0.002. Optionally a protease can be added which brings about the cleavage of the precursor protein of hemagglutinin [$HA_0$] and thus the adsorption of the viruses on the cells. The addition of a protease can be carried out according to the invention shortly before, simultaneously to or shortly after the infection of the cells with influenza viruses. If the addition is carried out simultaneously to the infection, the protease can either be added directly to the cell culture to be infected or, for example, as a concentrate together with the virus inoculate. The protease is, in certain aspects of the invention, a serine protease, or a cysteine protease, or an asparagine protease. In one embodiment, trypsin is used. In a specific embodiment, TPCK-treated trypsin is used. In another embodiment, the protease from *Streptomyces griseus* described in U.S. application Ser. No. 11/455,818 is used. The trypsin can be from an animal source, or, more preferably, is from a recombinant source.

In one embodiment, trypsin is added to the cell culture up to a final concentration of 1 to 5000 mU/ml, or 5 to 1000 mU/ml, or 100 to 500 mU/ml. In an alternative embodiment, trypsin is added to the cell culture up to a final concentration of 1 to 200 µg/ml, or 5 to 50 µg/ml, or 5 to 30 µg/ml in the culture medium. During the further culturing of the infected cells according to step (iii) of the process according to the invention, trypsin reactivation can be carried out by fresh addition of trypsin in the case of the batch or fed batch process or in the case of the perfusion system by continuous addition of a trypsin solution or by intermittent addition.

After infection, the infected cell culture is cultured further to replicate the viruses, in particular until a maximum cytopathic effect or a maximum amount of virus and/or virus antigen can be detected. In certain embodiments, the culturing of the cells is carried out for 2 to 10 days. The culturing can in turn be carried out in the perfusion system or optionally in the batch or fed batch process. In a further embodiment, the cells are cultured at a temperature of 25° C. to 36° C., or of 29° C. to 34° C., after infection with influenza viruses. The culturing of the infected cells at temperatures below 33° C., in particular in the temperature ranges indicated above, leads to the production of higher yields of certain influenza viruses, such as, for example B strains (see, e.g., U.S. Patent Publication 2006/0153872). Furthermore, the culturing of the infected cells at temperatures below 35° C. is contemplated for the production of temperature sensitive, cold adapted (ts/ca) influenza virus. It is contemplated that is/ca viruses may also be attenuated (att). In another embodiment, the cells are cultured at a temperature of less than 30° C., or of less than 31° C., or of less than 32° C., or of less than 33° C., or of less than 34° C. for the production of is/ca influenza strains. In a specific embodiment, the cells are cultured at a temperature of 31° C., for the production of influenza virus B strains.

The culturing of the cells after infection with influenza viruses (step (iii)) is in turn carried out, for example, as described supra In one embodiment of the process, the harvesting and isolation of the produced influenza viruses (step (iii)) is carried out after a sufficient period to produce suitable yields of virus, such as 2 to 10 days, or 3 to 7 days, after infection. Viruses are typically recovered from the culture medium, in which infected cells have been grown. Typically crude medium is clarified prior to concentration of influenza viruses. Common methods include filtration, ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Alternatively, the medium is filtered through a 0.8 µm cellulose acetate filter to remove intact cells and other large particulate matter. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus may be concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large scale commercial applications, virus is elutriated from density gradients using a zonal-centrifuge rotor operating in continuous mode. Additional details sufficient to guide one of skill through the preparation of influenza viruses from tissue culture are provided, e.g., in Furminger, in *Textbook of Influenza* pp. 324-332 Nicholson et al. (ed); Merten et al., in *Novel Strategies in Design and Production of Vaccines* pp. 141-151 Cohen & Shafferman (ed), and U.S. Pat. No. 5,690,937. If desired, the recovered viruses can be stored at −80° C. in the presence of a stabilizer, such as sucrose-phosphate-glutamate (SPG).

In certain embodiments of the process, the virus is treated with Benzonase® or other a non-specific endonuclease. Optionally, the Benzonase® treatment occurs early in the harvesting and isolation of the produced influenza viruses. In other embodiments of the process, following Benzonase® treatment, the material is clarified. Methods useful for clarification include but are not limited to, direct flow filtration (DFF). Additional steps which may be utilized for the harvesting and isolation of the produced influenza virus (step (iii)) include but are not limited to, tangential flow filtration (TFF), affinity chromatography as well as ion-exchange chromatography and/or hydroxyapatite chromatography. In certain embodiments, affinity chromatography is used in process. It will be understood by one of skill in the art that a variety of affinity chromatography media are available with similar separation properties, for example numerous affinity chromatography media are available for the concentration and purification of a number of viruses and viral proteins. In a specific embodiment, Cellufine™ Sulfate (Chisso Corp.) affinity media is utilized for affinity chromatography. In another embodiment, FluSelect (GE Healthcare) is utilized for affinity chromatography. In one embodiment, the virus is treated with Benzonase® at the same time as an affinity chromatography process. In certain embodiments, membrane chromatography is used in the process. In one embodiment, ion exchange chromatography is used in the process. In a specific embodiment, cation exchange chromatography is used in the process. In certain embodiments, cation exchange chromatography is performed at high pH. In a specific embodiment, anion exchange chromatography is used in the process. In certain embodiments, anion exchange chromatography is performed at low pH. Anion membranes useful for ion exchange chromatography include, but are not limited to, anion membrane adsorbers (e.g., Sartobind® Q15, D15) and cation membrane adsorbers (e.g., Sartobind® S15 and C15). Other steps are exemplified in the Examples section below.

7.6 Vaccine Compositions and Methods of Use

The invention further relates to viruses (e.g., influenza) which are obtainable by a process of the invention. These viruses can be formulated by known methods to provide a vaccine for administration to humans or animals. The viruses can be present as intact virus particles (e.g., live attenuated viruses) or as inactive/disintegrated virus (e.g., treated with detergents of formaldehyde). Optionally, a defined viral component (e.g., protein) may be isolated from the viruses by methods know to the person skilled in the art, and used in the preparation of a vaccine. Methods for the generation and formulation of inactive/disintegrated virus particles for vaccine compositions are well known in the art and have been utilized for over 40 years.

The formulation of intact virus particles (e.g., live attenuated viruses) may include additional steps including, but not limited to, a buffer exchange by filtration into a final formulation followed by a sterilization step. Buffers useful for such a formulation may contain 200 mM sucrose and a phosphate or histidine buffer of pH 7.0-7.2 with the addition of other amino acid excipients such as arginine. In certain embodiments, stabilization protein hydrolysates such as collagen or gelatin (e.g., porcine, piscine, avian gelatin) are added. In some embodiments, the final viral solutions/vaccines of the invention can comprise live viruses that are stable in liquid form for a period of time sufficient to allow storage "in the field" (e.g., on sale and commercialization when refrigerated at 2-8° C., 4° C., 5° C., etc.) throughout an influenza vaccination season (e.g., typically from about September through March in the northern hemisphere). Thus, the virus/vaccine compositions are desired to retain their potency or to lose their potency at an acceptable rate over the storage period. In other embodiments, such solutions/vaccines are stable in liquid form at from about 2° C. to about 8° C., e.g., refrigerator temperature. For example, methods and compositions for formulating a refrigerator stable attenuated influenza vaccine are described in PCT Patent Publication No. WO/2006/041819; also see PCT Publication WO/2005/014862.

Thus, in certain embodiments, the invention provides a refrigerator stable vaccine formulation comprising one or more of the following (within 10% variation of one or more component) in the final formulations: 1-5% arginine; 1-4% gelatin; 5-10% sucrose (optionally in a phosphate buffer); 0.01-0.1% glutamic acid (monosodium, monohydrate); 10-150 mM potassium phosphate and 80-150 mM histidine.

In one specific embodiment, the vaccine formulation comprises one or more of the following (within 10% variation of one or more component): 1-2% arginine; 2% gelatin; 7-10% sucrose (optionally in a phosphate buffer); and 100 mM histidine. In another specific embodiment, the vaccine formulation comprises one or more of the following (within 10% variation of one or more component): 1-2% arginine; 1% gelatin; and 7-10% sucrose in a phosphate buffer.

In certain other embodiments, the invention provides a refrigerator stable vaccine formulation comprising one or more of the following in the final formulations: sucrose: 6-8% weight/volume (w/v); arginine monohydrochloride 1-2% w/v; glutamic acid, monosodium monohydrate 0.05-0.1% w/v; gelatin hydrolysate, porcine Type A (or other sources such as piscine or avian) 0.5-2% w/v; potassium phosphate dibasic 1-2%; and potassium phosphate monobasic 0.25-1% w/v.

In one specific embodiment, the vaccine formulation comprises one or more of the following: sucrose: 6.84% weight/volume (w/v); arginine monohydrochloride 1.21% w/v; glutamic acid, monosodium monohydrate 0.094 w/v; gelatin hydrolysate, porcine Type A (or other sources) 1% w/v; potassium phosphate dibasic 1.13%; and potassium phosphate monobasic 0.48% w/v. In another specific embodiment, the vaccine formulation comprises all of the following: sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In another specific embodiment, the vaccine formulation comprises all of the following (within 10% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v. In another specific embodiment, the vaccine formulation comprises all of the following (within 10% variation of one or more component): sucrose: 6.84% weight/volume (w/v); arginine monohydrochloride 1.21% w/v; gelatin hydrolysate, porcine Type A (or other sources) 1% w/v. In such embodiments, formulations are in buffer {e.g., a potassium phosphate buffer (pH 7.0-7.2)). In another specific embodiment, vaccine formulations comprise all of the following (within 20% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In yet another specific embodiment, the vaccine formulation comprises all of the following (within 30% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v. In still another specific embodiment, the vaccine formulation comprises all of the following (within 40% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v.

In another specific embodiment, the vaccine formulation comprises all of the following (within 1% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v. In another specific embodiment, the vaccine formulation comprises all of the following (within 3% variation of one or more component): sucrose: 6.84% weight/volume (w/v); arginine monohydrochloride 1.21% w/v; glutamic acid, monosodium monohydrate 0.094% w/v; gelatin hydrolysate, porcine Type A (or other sources) 1% w/v; potassium phosphate dibasic 1.13%; and potassium phosphate monobasic 0.48% w/v. In a specific embodiment, the vaccine formulation may contain, e.g., potassium phosphate (e.g., at least 50 mM, or at least 100 mM, or at least 200 mM, or at least 250 mM) as a buffer or alternatively, histidine (e.g., at least 50 mM, or at least 100 mM, or at least 200 mM, or at least 250 mM).

Optionally, spray drying, a rapid drying process whereby the formulation liquid feed is spray atomized into fine droplets under a stream of dry heated gas, may be utilized to extend storage time of a vaccine formulation. The evaporation of the fine droplets results in dry powders composed of the dissolved solutes (see, e.g., US Patent Publication No. 2004/0042972).

Generally, virus or viral components can be administered prophylactically in an appropriate carrier or excipient to stimulate an immune response specific for one or more strains of virus. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

Optionally, the formulation for prophylactic administration of the viruses, or components thereof, also contains one or more adjuvants for enhancing the immune response to the influenza antigens. Suitable adjuvants include: saponin, mineral gels such as aluminum hydroxide, surface active substances such as lysolecithin, pluronic polyols, polyanions, peptides, oil or hydrocarbon emulsions, Bacille Calmette-Guerin (BCG), *Corynebacterium parvum*, and the synthetic adjuvants QS-21 and MF59.

Generally, vaccine formulations are administered in a quantity sufficient to stimulate an immune response specific for one or more strains of influenza virus. Preferably, administration of the viruses elicits a protective immune response. Dosages and methods for eliciting a protective immune response against one or more viral strain are known to those of skill in the art. For example, inactivated influenza viruses are provided in the range of about 1-1000 $HID_{50}$ (human infectious dose), i.e., about $10^5$-$10^8$ pfu (plaque forming units) per dose administered. Alternatively, about 10-50 µg, e.g., about 15 µg HA is administered without an adjuvant, with smaller doses being administered with an adjuvant. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needleless injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. While stimulation of a protective immune response with a single dose is preferred, additional dosages can be administered, by the same or different route, to achieve the desired prophylactic effect. These methods can be adapted for any virus including but not limited to, orthomyxoviruses (including influenza A and B strains), paramyxoviruses (including RSV, human metapneumovirus and parainfluenza), rhabdoviruses and flavoviruses.

7.6.1. Influenza Virus

The methods, processes and compositions herein primarily concerned with production of influenza viruses for vaccines. Influenza viruses are made up of an internal ribonucleoprotein core containing a segmented single-stranded RNA genome and an outer lipoprotein envelope lined by a matrix protein. Influenza A and influenza B viruses each contain eight segments of single stranded negative sense RNA. The influenza A genome encodes eleven polypeptides. Segments 1-3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuraminidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants.

The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a biscistronic mRNA. Segment 7 of influenza B also encodes two proteins: M1 and M2. The smallest segment encodes two products, NS1 which is translated from the full length RNA, and NS2 which is translated from a spliced mRNA variant.

Reassortant viruses are produced to incorporate selected hemagglutinin and neuraminidase antigens in the context of an approved master strain also called a master donor virus (MDV). FluMist® makes use of approved cold adapted, attenuated, temperature sensitive MDV strains (e.g., A/AnnArbor/6/60 and B/Ann Arbor/1/66).

A number of methods are useful for the generation of reassortant viruses including egg-based methods and more recently cell culture methods See, e.g., PCT Publications WO 03/091401; WO 05/062820 and U.S. Pat. Nos. 6,544,785; 6,649,372; 6,951,75, and U.S. patent application Ser. Nos. 11/455,818, 11/455,734, and 11/501,067. It is contemplated that the MDCK cells, media and methods of the invention are useful for the production of influenza viruses including, but not limited to, the influenza strains disclosed herein (e.g., A/AnnArbor/6/60 and B/AnnArbor/1/66) and reassortant viruses comprising genes of the A/AnnArbor/6/60, B/AnnArbor/1/66, PR8. It is further contemplated that that the MDCK cells, media and methods of the invention are useful for the production of influenza viruses, including reassortant viruses, having one or more of the following phenotypes, temperature sensitive, cold adapted, attenuated. Reassortants may be generated by classical reassortant techniques, for example by co-infection methods or optionally by plasmid rescue techniques (see, e.g., PCT Publications WO 03/091401 and WO 05/062820; U.S. Pat. Nos. 6,544,785, 6,649,372, 6,951,754, 6,887,699, 6,001,634, 5,854,037, 5,824,536, 5,840,520, 5,820,871, 5,786,199, and 5,166,057; U.S. Patent Application Publication Nos. 20060019350, 20050158342, 20050037487, 20050266026, 20050186563, 20050221489, 20050032043, 20040142003, 20030035814, and 20020164770; and Neumann et al. (1999) *Generation of influenza A virus entirely from cloned cDNAs. Proc Natl Acad Sci USA* 96:9345-9350; Fodor et al. (1999) *Rescue of influenza A virus from recombinant DNA. J. Virol* 73:9679-9682; Hoffmann et al. (2000) *A DNA transfection system for generation of influenza A virus from eight plasmids Proc Natl Acad Sci USA* 97:6108-6113; WO 01/83794; Hoffmann and Webster (2000), *Unidirectional RNA polymerase I-polymerase II transcription system for the generation of influenza A virus from eight plasmids,* 81:2843-2847; and Hoffmann et al. (2002), *Rescue of influenza B viruses from 8 plasmids,* 99(17): 11411-11416.

Accordingly, the invention in another aspect provides an MDCK cell of the invention that comprises one or more genomic segments of an influenza virus. In certain embodiments, the cell comprises all eight genomic segments of an influenza virus. In certain embodiments, the eight genomic segments are each from the same influenza virus. In certain embodiments, the eight genomic segments are from one, two, or more different influenza viruses. In certain embodiments, the eight genomic segments comprise two segments encoding HA and NA, respectively, from any influenza strain known to one skilled in the art without limitation and the remaining genomic segments are from a cold-adapted, and/or temperature, sensitive, and/or attenuated influenza virus. In certain embodiments, the cell comprises any influenza genomic segment described in any of the publications described above.

8. SPECIFIC EMBODIMENTS

1. A Madin-Darby Canine Kidney (MCDK) cell, wherein a cell culture composition comprising a plurality of the MDCK cells supports replication of an attenuated, cold-adapted, temperature sensitive influenza virus to a base 10 logarithm of the median tissue culture infection dose per milliliter ($\log_{10}$ TCID$_{50}$/mL) of at least about 7.0 or to a base 10 logarithm of fluorescent focus units per milliliter ($\log_{10}$ FFU/mL) of at least about 7.0.

2. The MDCK cell of embodiment 1, wherein the MDCK cells support replication of the influenza virus to a $\log_{10}$ TCID$_{50}$/mL of at least about 7.2 and/or to a $\log_{10}$ FFU/mL of at least about 7.2.

3. The MDCK cell of embodiment 1, wherein the MDCK cells support replication of the influenza virus to a $\log_{10}$ TCID$_{50}$/mL of at least about 7.4 and/or to a $\log_{10}$ FFU/mL of at least about 7.4.

4. The MDCK cell of embodiment 1, wherein the MDCK cells support replication of the influenza virus to a $\log_{10}$ TCID$_{50}$/mL of at least about 7.6 and/or to a $\log_{10}$ FFU/mL of at least about 7.6.

5. The MDCK cell of embodiment 1, wherein the MDCK cells support replication of the influenza virus to a $\log_{10}$ TCID$_{50}$/mL of at least about 7.8 and/or to a $\log_{10}$ FFU/mL of at least about 7.8.

6. The MDCK cell of embodiment 1, wherein the MDCK cells support replication of the influenza virus to a $\log_{10}$ TCID$_{50}$/mL of at least 8.0 and/or to a $\log_{10}$ FFU/mL of at least about 8.0.

7. The MDCK cell of embodiment 1, wherein the MDCK cells support replication of the influenza virus to a $\log_{10}$ TCID$_{50}$/mL of at least 8.2 and/or to a $\log_{10}$ FFU/mL of at least about 8.2.

8. The MDCK cell of embodiment 1, wherein the MDCK cells support replication of the influenza virus to a $\log_{10}$ TCID$_{50}$/mL of at least 8.4 and/or to a $\log_{10}$ FFU/mL of at least about 8.4.

9. The MDCK cell of embodiment 1, wherein the MDCK cells support replication of the influenza virus to a $\log_{10}$ TCID$_{50}$/mL of at least 8.6 and/or to a $\log_{10}$ FFU/mL of at least about 8.6.

10. The MDCK cell of embodiment 1, wherein the MDCK cells support replication of the influenza virus to a $\log_{10}$ TCID$_{50}$/mL of at least 8.8 and/or to a $\log_{10}$ FFU/mL of at least about 8.8.

11. The MDCK cell of embodiment 1, wherein the MDCK cells support replication of the influenza virus to a $\log_{10}$ TCID$_{50}$/mL of at least 9.0 and/or to a $\log_{10}$ FFU/mL of at least about 9.0.

12. The MDCK cell of embodiment 1, wherein the MDCK cell grows in serum-free medium.

13. The MDCK cell of embodiment 1, wherein the serum free media is an animal protein free media.

14. The MDCK cell of embodiment 1, wherein the MDCK cell is adherent.

15. The MDCK cell of embodiment 1, wherein the MDCK cell is non-adherent.

16. The MDCK cell of embodiment 1, wherein the MDCK cell is non-tumorigenic.

17. The MDCK cell of embodiment 1, wherein the MDCK cell is non-oncogenic.

18. The MDCK cell of embodiment 1, wherein the MDCK cell is derived from an MDCK cell line identified by American Type Culture Collection (ATCC) Accession No. CCL34.

19. The MDCK cell of embodiment 1, wherein the MDCK cell is derived from an MDCK cell line identified by ATCC Accession No. PTA-6500, PTA-6501, PTA-6502 or PTA-6503.

20. The MDCK cell of embodiment 1, wherein the MDCK cell is identified by ATCC Accession No. PTA-7909 or PTA-7910.

21. The MDCK cell of embodiment 1, wherein the influenza virus is an influenza A virus.

22. The MDCK cell of embodiment 1, wherein the influenza virus is an influenza B virus.

23. The MDCK cell of embodiment 1, wherein the influenza virus is a cold adapted virus.

24. The MDCK cell of embodiment 1, wherein the influenza virus is a temperature sensitive virus.

25. The MDCK cell of embodiment 1, wherein the influenza virus is an attenuated virus.

26. The MDCK cell of embodiment 1, wherein the influenza virus is an attenuated, cold adapted, and temperature sensitive virus.

27. The MDCK cell of embodiment 1, wherein the influenza virus comprises one or more gene segments of a temperature sensitive, attenuated and cold adapted influenza virus.

28. The MDCK cell of embodiment 1, wherein the influenza virus comprises one or more gene segments of influenza strain A/Ann Arbor/6/60.

29. The MDCK cell of embodiment 1, wherein the influenza virus comprises one or more gene segments of B/Ann Arbor/1/66.

30. A method for proliferating the MDCK cell of any of the preceding embodiments to a cell density of at least about $1\times10^6$ cells/ml in a SUB system comprising inoculating a cell culture medium with the MDCK cell of any of the preceding embodiments at a seeding density of between about $8\times10^4$ to about $12\times10^4$ cells/mL and culturing the cells while maintaining one or more culture conditions selected from the group consisting of:

a. an agitation rate of between about 50 to 150 rpm;
b. a pH of between about 6.0 to about 7.5;
c. dissolved oxygen (DO) between about 35% to about 100%; and
d. a temperature of between about 33° C. to about 42° C.

31. The method of embodiment 30, wherein the cell culture medium is a serum free medium.

32. The method of embodiment 30, wherein the cell culture medium is an animal protein free medium.

33. The method of embodiment 30, wherein the cell culture medium is MediV-105 supplemented with glucose, or M-32 or MediV-107.

34. The method of embodiment 30, wherein the agitation rate is between about 90 to about 100 rpm.

35. The method of embodiment 30, wherein the DO is between about 35% to about 100%.

36. The method of embodiment 30, wherein the temperature is between about 36° C. and about 38° C.

37. The method of embodiment 30, wherein a microcarrier is used for culturing an adherent MDCK cell.

38. The method of embodiment 37, wherein the microcarrier concentration is between about 1 to about 4 g/L.

39. A cell culture composition produced by the method of any one of embodiments 30 to embodiment 38.

40. A cell culture composition comprising MCDK cells and a cell culture medium, wherein the cell culture composition supports replication of an influenza virus to a $\log_{10}$ $TCID_{50}$/mL of at least about 7.0 and/or to a $\log_{10}$ FFU/mL of at least about 7.0.

41. The cell culture composition of embodiment 40, wherein the MDCK cell culture composition supports replication of the influenza virus to a $\log_{10}$ $TCID_{50}$/mL of at least about 7.2 and/or to a $\log_{10}$ FFU/mL of at least about 7.2.

42. The cell culture composition of embodiment 40, wherein the MDCK cell culture composition supports replication of the influenza virus to a $\log_{10}$ $TCID_{50}$/mL of at least about 7.4 and/or to a $\log_{10}$ FFU/mL of at least about 7.4.

43. The cell culture composition of embodiment 40, wherein the MDCK cell culture composition supports replication of the influenza virus to a $\log_{10}$ $TCID_{50}$/mL of at least about 7.6 and/or to a $\log_{10}$ FFU/mL of at least about 7.6.

44. The cell culture composition of embodiment 40, wherein the MDCK cell culture composition supports replication of the influenza virus to a $\log_{10}$ $TCID_{50}$/mL of at least about 7.8 and/or to a $\log_{10}$ FFU/mL of at least about 7.8.

45. The cell culture composition of embodiment 40, wherein the MDCK cell culture composition supports replication of the influenza virus to a $\log_{10}$ $TCID_{50}$/mL of at least about 8.0 and/or to a $\log_{10}$ FFU/mL of at least about 8.0.

46. The cell culture composition of embodiment 40, wherein the MDCK cell culture composition supports replication of the influenza virus to a $\log_{10}$ $TCID_{50}$/mL of at least about 8.2 and/or to a $\log_{10}$ FFU/mL of at least about 8.2.

47. The cell culture composition of embodiment 40, wherein the MDCK cell culture composition supports replication of the influenza virus to a $\log_{10}$ $TCID_{50}$/mL of at least about 8.4 and/or to a $\log_{10}$ FFU/mL of at least about 8.4.

48. The cell culture composition of embodiment 40, wherein the MDCK cell culture composition supports replication of the influenza virus to a $\log_{10}$ $TCID_{50}$/mL of at least about 8.6 and/or to a $\log_{10}$ FFU/mL of at least about 8.6.

49. The cell culture composition of embodiment 40, wherein the MDCK cell culture composition supports replication of the influenza virus to a $\log_{10}$ $TCID_{50}$/mL of at least about 8.8 and/or to a $\log_{10}$ FFU/mL of at least about 8.8.

50. The cell culture composition of embodiment 40, wherein the MDCK cell culture composition supports replication of the influenza virus to a $\log_{10}$ $TCID_{50}$/mL of at least about 9.0 and/or to a $\log_{10}$ FFU/mL of at least about 9.0.

51. The cell culture composition of embodiment 40, wherein the cell culture composition does not comprise animal serum.

52. The cell culture composition of embodiment 40, wherein the cell culture composition does not comprise a protein purified from an animal.

53. The cell culture composition of embodiment 40, wherein the cell culture composition comprises a recombinantly-expressed protein.

54. The cell culture composition of embodiment 53, wherein the protein is expressed by at least one of the MDCK cells.

55. The cell culture composition of embodiment 53, wherein the protein is expressed in a recombinant expression system and then added to the cell culture composition.

56. The cell culture composition of embodiment 53, wherein the recombinantly-expressed protein is insulin or trypsin.

57. The cell culture composition of embodiment 40, wherein at least some of the MDCK cells are adherent.

58. The cell culture composition of embodiment 40, wherein the MDCK cells are adherent.

59. The cell culture composition of embodiment 40, wherein at least some of the MDCK cells are non-adherent.

60. The cell culture composition of embodiment 40, wherein the MDCK cells are non-adherent.

61. The cell culture composition of embodiment 40, wherein the MDCK cells are non-tumorigenic.

62. The cell culture composition of embodiment 40, wherein the MDCK cells are derived from the MDCK cell line identified by American Type Culture Collection (ATCC) Accession No. CCL34.

63. The cell culture composition of embodiment 40, wherein the MDCK cells are derived from an MDCK cell line identified by ATCC Accession No. PTA-6500, PTA-6501, PTA-6502 or PTA-6503.

64. The cell culture composition of embodiment 40, wherein the MDCK cells are identified by ATCC Accession No. PTA-7909 or PTA-7910.

65. The cell culture composition of embodiment 40, wherein the influenza virus is an influenza A virus.

66. The cell culture composition of embodiment 40, wherein the influenza virus is an influenza B virus.

67. The cell culture composition of embodiment 40, wherein the influenza virus is a cold adapted virus.

68. The cell culture composition of embodiment 40, wherein the influenza virus is an attenuated virus.

69. The cell culture composition of embodiment 40, wherein the influenza virus comprises one or more gene segments of a temperature sensitive, attenuated and cold adapted influenza virus.

70. The cell culture composition of embodiment 40, wherein the influenza virus comprises one or more gene segments of influenza strain A/Ann Arbor/6/60.

71. The cell culture composition of embodiment 40, wherein the influenza virus comprises one or more gene segments of B/Ann Arbor/1/66.

72. The cell culture composition of embodiment 40, wherein the MDCK cells are cultured at between about 25° C. and about 33° C. during the replication of the influenza virus.

73. The cell culture composition of embodiment 40, wherein the MDCK cells do not comprise detectable oncogenic DNA.

74. The cell culture composition of embodiment 40, wherein the cell culture composition does not comprise detectable mycoplasma.

75. The cell culture composition of embodiment 40, wherein the cell culture composition does not comprise detectable bacteria.

76. The cell culture composition of embodiment 40, wherein the cell culture composition does not comprise a detectable virus other than an influenza virus.

77. The cell culture composition of embodiment 40 wherein the detectable virus is a virus that infects canine or human cells.

78. The cell culture composition of embodiment 40, wherein the MDCK cells do not comprise a latent virus.

79. The cell culture composition of embodiment 40, wherein the MDCK cells do not comprise a retrovirus.

80. The cell culture composition of embodiment 40, wherein the MDCK cells are grown to a cell density of at least about $1 \times 10^5$ cells/ml.

81. The cell culture composition of embodiment 40, wherein the MDCK cells are grown to a cell density of at least about $5 \times 10^5$ cells/ml.

82. The cell culture composition of embodiment 40, wherein the MDCK cells are grown to a cell density of at least about $1 \times 10^6$ cells/ml.

83. The cell culture composition of embodiment 40, wherein the MDCK cells are grown to a cell density of at least about $2.5 \times 10^6$ cells/ml.

84. The cell culture composition of embodiment 40, wherein the MDCK cells are grown to a cell density of at least about $5 \times 10^6$ cells/ml 85. A method for producing influenza viruses in cell culture, comprising:
   a. infecting the cell culture composition of any of embodiments 40-84 with an influenza virus,
   b. incubating the cell culture composition under conditions that permit replication of the influenza virus; and
   c. isolating influenza viruses from the cell culture composition.

86. The method of embodiment 85, wherein fresh medium or additional medium components are added to the cell culture prior to or during step (a).

87. The method of embodiment 85, wherein none or some of the cell culture medium is removed and replaced with fresh medium prior to or during step (a).

88. The method of embodiment 85, wherein step (a) is carried out at a Multiplicity Of Infection (MOI) of between about 0.00001 to about 0.00003 FFU/cell.

89. The method of embodiment 85, wherein step (a) is carried out at an MOI of between about 0.0001 to about 0.0003 FFU/cell.

90. The method of embodiment 85, wherein step (a) is carried out at an MOI of between about 0.001 to about 0.003 FFU/cell.

91. The method of embodiment 85, wherein the conditions of step (b) are selected from the group consisting of:
   a. an agitation rate of between about 50 to 150 rpm;
   b. a pH of between about 6.0 to about 7.5;
   c. dissolved oxygen (DO) between about 35% to about 100%; and
   d. a temperature of between about 30° C. to about 35° C.

92. The method of embodiment 85, wherein the influenza virus replicates to a $\log_{10}$ TCID$_{50}$/mL of at least about 7.0 and/or to a $\log_{10}$ FFU/mL of at least about 7.0.

93. The method of embodiment 85, wherein the influenza virus replicates to a $\log_{10}$ TCID$_{50}$/mL of at least about 7.2 and/or to a $\log_{10}$ FFU/mL of at least about 7.2.

94. The method of embodiment 85, wherein the influenza virus replicates to a $\log_{10}$ TCID$_{50}$/mL of at least about 7.4 and/or to a $\log_{10}$ FFU/mL of at least about 7.4.

95. The method of embodiment 85, wherein the influenza virus replicates to a $\log_{10}$ TCID$_{50}$/mL of at least about 7.6 and/or to a $\log_{10}$ FFU/mL of at least about 7.6.

96. The method of embodiment 85, wherein the influenza virus replicates to a $\log_{10}$ TCID$_{50}$/mL of at least about 7.8 and/or to a $\log_{10}$ FFU/mL of at least about 7.8.

97. The method of embodiment 85, wherein the influenza virus replicates to a $\log_{10}$ TCID$_{50}$/mL of at least about 8.0 and/or to a $\log_{10}$ FFU/mL of at least about 8.0.

98. The method of embodiment 85, wherein the influenza virus replicates to a $\log_{10}$ TCID$_{50}$/mL of at least about 8.2 and/or to a $\log_{10}$ FFU/mL of at least about 8.2.

99. The method of embodiment 85, wherein the influenza virus replicates to a $\log_{10}$ TCID$_{50}$/mL of at least about 8.4 and/or to a $\log_{10}$ FFU/mL of at least about 8.4.

100. The method of embodiment 85, wherein the influenza virus replicates to a $\log_{10}$ TCID$_{50}$/mL of at least about 8.6 and/or to a $\log_{10}$ FFU/mL of at least about 8.6.

101. The method of embodiment 85, wherein the influenza virus replicates to a $\log_{10}$ TCID$_{50}$/mL of at least about 8.8 and/or to a $\log_{10}$ FFU/mL of at least about 8.8.

102. The method of embodiment 85, wherein the influenza virus replicates to a $\log_{10}$ TCID$_{50}$/mL of at least about 9.0 and/or to a $\log_{10}$ FFU/mL of at least about 9.0.

103. An influenza virus produced according to the method of embodiment 85.

104. An immunogenic composition comprising polypeptides of the influenza virus of embodiment 103 in a pharmaceutically acceptable carrier or diluent.

105. An immunogenic composition comprising the influenza virus of embodiment 103 in a pharmaceutically acceptable carrier or diluent.

106. The immunogenic composition of embodiment 105, wherein the immunogenic composition is refrigerator stable.

107. A method of eliminating DNA contaminants from a viral preparation comprising:
 (a) passing the viral preparation over affinity chromatography media under conditions wherein the DNA contaminants are not retained on the affinity chromatography media and the virus present in the viral preparation are retained;
 (b) washing the affinity chromatography media to remove the DNA contaminants; and
 (c) eluting the virus present in the viral preparation from the affinity chromatography media.

108. The method of 107, wherein the affinity chromatography media is Cellufine Sulfate resin.

109. The method of embodiment 107, wherein between steps (a) and (b) a non-specific endonuclease preparation is passed over the affinity chromatography media.

110. The method of embodiment 108, wherein the non-specific endonuclease is a Benzonase preparation comprises Benzonase in 1× SP buffer at about pH 7.2.

111. The method of embodiment 107, wherein the viral preparation is an influenza virus preparation.

112. The method of embodiment 108, wherein the influenza virus preparation was prepared from mammalian cells.

113. The method of embodiment 112, wherein the mammalian cells are MDCK cells or Vero cells, or PerC6 cells.

114. The method of embodiment 107, wherein the conditions used in step (a) are 1× SP buffer at about pH 7.2.

115. The method of embodiment 107, wherein the virus present in the viral preparation are eluted in 1× SP buffer containing about 1 M NaCl at about pH 7.2.

9. EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

9.1 Example 1

Identification of a MDCK Cell Line that Supports High Viral Replication in Serum Containing Media This example describes identification and selection of an MDCK cell line that supports replication of influenza viruses to high titers when the MDCK cell line was cultured in Dulbecco's Modified Eagle's Medium (DMEM) media comprising 10% Fetal Bovine Serum (FBS). The process is outlined in FIG. 5A.

One vial of MDCK cells (ATCC Accession No. CCL-34; Lot 1805449; passage 54) obtained from the ATCC was thawed and inoculated into a T-25 flask (Corning) containing 10 ml of Dulbecco's Modified Eagle's Medium with L-glutamine (DMEM) and 10% fetal bovine serum (FBS, Defined). Cells (passage 55) were incubated at 37±1° C. with 5±1% $CO_2$ for 3 days. On day 3, the cells were passaged to a T-225 flask (passage 56). Three days after seeding, cells were passaged to 4× T-225 flasks (Passage 57). For each of the passages in DMEM with L-glutamine and 10% FBS in a T-25 or T-225 flask, the procedure was as follows.

Cells were washed twice with Dulbecco's Phosphate Buffered Saline without $Ca^{++}$ and $Mg^{++}$ (DPBS), and 1.5 ml (for T-25) or 7.5 ml (for T-225) of trypsin 0.25% were added to the cells. The cell monolayer was incubated and allowed to release for 15 to 20 minutes, at which time 1.5 ml (for the T-75 flask) or 7.5 ml (for the T-225 flask) of DMEM with L-glutamine and 10% FBS were added to neutralize the trypsin. The cells were then counted using a hemacytometer, and the amount necessary to inoculate $5 \times 10^4$ cells per ml was transferred to a T-225 flask containing 100 ml of DMEM with L-glutamine and 10% FBS, and incubated as above for 3 days. Cells from 4 T-225 flasks were trypsinized, pooled, and serum containing growth medium was added as described above. The cells were then mixed and counted. The cell suspension was centrifuged and the cell pellet was resuspended with 10 ml of DMEM with L-glutamine and 10% FBS. This suspension was counted again. Ten ml of 2× freezing medium (10% FBS DMEM with L-glutamine and 15% v/v dimethyl sulfoxide) was added, the cells were mixed thoroughly, and 1 ml was aliquoted into each of 20 cryovials. The cells were frozen at −80° C. in Nalgene freezer containers, and then transferred to storage in vapor phase of liquid nitrogen. The frozen cells represented the MDCK cells at passage 57 and are referred to herein as MDCK Pre-MCB lot 1.

Next, one vial of the MDCK Pre-MCB lot 1 was thawed and inoculated into a T75 flask containing 35 ml of DMEM and 10% FBS. Cells (passage 58) were incubated at 37° C. with 5% $CO_2$ for 3 days. On day 3 the cells were passaged to 2× T225 flasks (passage 59). Three days after seeding, cells were passaged to 4× T225 flasks (Passage 60). On day 3 post seeding, a complete medium exchange was performed. Four days after seeding, cells were passaged to 25× T225 flasks (Passage 61). For each of the passages in DMEM with L-glutamine and 10% FBS in a T75 or T225 flask, the procedure was as follows.

Cells were washed two times with Dulbecco's Phosphate Buffered Saline without $Ca^{++}$ and $Mg^{++}$ (DPBS), and 3 ml (for T75) or 7.5 ml (for T225) of trypsin 0.25% was added to the cells. The cell monolayer was incubated and allowed to release for 15 to 20 minutes, at which time 3 ml (for T75) or 7.5 ml (for T225 flask) of DMEM with L-glutamine and 10% FBS was added to neutralize the trypsin. The cells were then counted in a hemacytometer, and the amount necessary to inoculate $5 \times 10^4$ cells per ml was transferred to a T225 flask containing 100 ml of DMEM with L-glutamine and 10% FBS, and incubated as above for 3 days. Cells from 24 of 25 T225 flasks were trypsinized, pooled, and serum containing growth medium was added. The cell suspension were centrifuged, and resuspended cell pellet with 50 ml of DMEM with L-glutamine and 10% FBS.

This suspension was then counted. To make 60 ml of $1 \times 10^7$ cells/ml cell suspension, 39.5 ml cell suspension was combined with 20.5 ml of 10% FBS DMEM medium. Then 60 ml of 2× freezing medium (10% FBS DMEM with L-glutamine and 15% v/v dimethyl sulfoxide) was added to 60 ml of $1 \times 10^7$ cells/ml cell suspension, the cells were mixed thoroughly, and 1 ml were aliquoted into each of 100 cryovials. The cells were frozen at −60° C. in Nalgene freezer containers, and then transferred to storage in liquid nitrogen. The frozen cells represented the MDCK cells at passage 61. These vials were designated MDCK Pre-MCB lot 2. This bank was deposited with the ATCC and is identified by ATCC Accession Number PTA-6500.

Next, one vial of the MDCK Pre-MCB lot 2 (Passage 61) was thawed and inoculated into a T75 flask containing 35 ml DMEM and 10% FBS. Cells (passage 62) were incubated at 37° C. with 5% $CO_2$ for 3 days. On day 3 the cells were passaged to 2× T75 flasks (passage 63). An additional 3 passages to a new T75 flask were performed followed by a passage to a T225 flask (Passage 67).

Next, the cells were trypsinized and cloned by a dilution method. In particular, the cells were seeded at 0.5 cells per 100 µL per well in 96 well plates (1:1 ratio of fresh to conditioned media). The next day, cells were visualized under the microscope and wells which contained one cell were identified, then the plates returned to incubate. After 7 days incubation, the plates were checked to assess cell growth and another 100 µL fresh growth medium was added to each well. Three days later, a complete medium exchange (200 µL per well) was performed. Two weeks after initial cloning seeding, cells were trypsinized and passaged to 2 sets of 24 well plates if they reached 100% confluence. If cells had not reached 100% confluence, they were refed with fresh growth medium.

The clones were expanded sequentially (24 well plate→T25 flasks or 6 well plates→T75 or T225 flask) and a total of 54 clones were selected as shown in Table 1, below, and frozen at either passage 4 or 5 post cloning in 10% FBS DMEM with 7.5% DMSO and stored in liquid nitrogen. In addition, clones 56, 57 and 58 were isolated from a second round of screening performed essentially as described above.

TABLE 1

List of 54 of Serum MDCK Clones (in freezing order)

| Clone ID | Clone ID | Clone ID | Clone ID | Clone ID | Clone ID |
|---|---|---|---|---|---|
| 1 | 10 | 19 | 28 | 37 | 46 |
| 2 | 11 | 20 | 29 | 38 | 47 |
| 3 | 12 | 21 | 30 | 39 | 48 |
| 4 | 13 | 22 | 31 | 40 | 49 |
| 5 | 14 | 23 | 55 | 41 | 50 |
| 6 | 15 | 24 | 33 | 42 | 51 |
| 7 | 16 | 25 | 34 | 43 | 52 |
| 8 | 17 | 26 | 35 | 44 | 53 |
| 9 | 18 | 27 | 36 | 45 | 54 |

Initial screening of virus productivity of clones was performed using one of the sets of 24 well plates produced above. To do so, the cells, cultured for 3 days in DMEM with 4 mM glutamine, were infected with influenza strain A/New Caledonia reassortant at an MOI of 0.001. 500 mU/ml TPCK trypsin was added once at time of infection. Virus titer was determined using the semi automated $TCID_{50}$ assay (n=12 per sample) as described in Example 5, below. The virus titer obtained from each clone varied from 7.0 to 8.5, with a distribution as shown in Table 2.

TABLE 2

Distribution of Viral Titers from 54 clones grown in DMEM containing 10% FBS

| Titer Range ($Log_{10} TCID_{50}/mL$) | Number of Clones (total of 54) |
|---|---|
| 7.0-7.5 | 6 |
| 7.6-8.0 | 35 |
| 8.1-8.5 | 12 |
| >8.5 | 1 |

Based on the virus productivity data, six clones were selected for further analysis: clones 1, 5, 36, 39, 40, and 55. The clones were expanded in T-flasks and a set T-25 (8 flasks per clone) were used for infection with A/New Caledonia, A/Panama and B/Jilin reassortants at MOI 0.001 using DMEM+4 mM glutamine as the post infection media (2 flasks per virus strain). These flasks were harvested 4 days post infection and the samples from each flask were analyzed for potency using the semi automated $TCID_{50}$ assay (n=12 per flask, n=24 per virus strain) of Example 5. Results from these experiments are presented as FIG. 1, which shows that the clones 1 and 55, which are the highest producers for reassortant A/New Caledonia, are also the highest producers for A/Panama and B/Jilin reassortants. Accordingly, clone 1 was selected for further subcloning and adaptation to serum free medium.

In additional rounds of screening performed as described above, more than 1000 clones were screened for ability to produce high titers of A/New Caledonia. Sixty three of these clones screened for ability to produce high titers of A/Panama and B/Jilin reassortants, none produced more virus than clone 1. Accordingly, none of these clones was selected for further study and no data relating to these clones is presented herein.

Next, clone 1 (P4/P71, 4 passages since isolation from a single clone, 71 total passages) was thawed and inoculated into a T75 flask containing 35 ml of Dulbecco's Modified Eagle's Medium/Ham F12 with L-glutamine (DMEM/F12) and 10% FBS. Cells were incubated at 37° C. with 5% $CO_2$ for 3 days. On day 3, the cells were passaged to a T225 flask. Then cells were passaged 8 times in either a T75 or T225 flask every 3 or 4 days after seeding. After these passages, the cells (P13/P80) were trypsinized and sub-cloned by dilution as follows.

The cells were seeded at 0.5 cells per 100 µL, per well in 10×96 well plates (1:1 ratio of fresh to conditioned media). The next day, cells (P1/P81, P1 since subclone, P81 total passage) were visualized under the microscope and wells were marked that contained one cell per well. The cells were allowed to grow for 7 days and the plates were checked to see if the marked wells contained growing cells. The cells were fed with 100 µL fresh growth medium at this time point, and then a complete medium exchange (200 µL per well) was performed 3 days later. Two weeks after initial cell seeding, single cell clones were trypsinized and passaged to a 96 well plate if they reached >50% confluence. Cells less than 50% confluent were refed with fresh growth medium and allowed to continue to grow. The clones which reached >50% confluence were expanded sequentially (24 well plate→6 well plates→T75 flask) and a total of 63 subclones were frozen at either passage 5 or 6 since the beginning of this round of subcloning in 10% FBS DMEM/F12 with 7.5% DMSO and stored in liquid nitrogen.

During clone expansion, clones were also set up in 3×96 well plates for virus infection (A/Panama and B/Jilin reassortants) at a MOI of 0.001. Cells were grown in DMEM/F12 with 4 mM glutamine, cells were infected at 3 days post seeding using DMEM/F12 with 4 mM glutamine as the post-infection media, and viruses were harvested 4 days post infection and stabilized with sucrose phosphate. The A/Panama virus titer was determined using a FFA assay as described in Example 4, below. A/Panama virus titer produced by each subclone varied from 7.0 to 8.5, with a distribution as shown in Table 3, below.

TABLE 3

Distribution of Viral Titers from 63 subclones of clone 1 grown in DMEM + 10% FBS

| Titer Range ($Log_{10}$ FFU/ml) | Number of Subclones (total of 63) |
|---|---|
| <6.1 | 28 |
| 6.2-6.9 | 18 |
| 7.0-7.5 | 13 |
| >7.6 (less than 8.0) | 4 |

9.2 Example 2

Adaptation of an MDCK Cell Clones to Growth in Serum-Free Media

This example describes adaptation of MDCK Clones 1, 55, 56, 57, and 58 and Subclones 1-A, 1-B (P5/P85), 1-C and 1-D to growth in MediV 105 serum-free media. Clones 56, 57, and 58 were derived from MDCK cells (ATCC Accession No. CCL-34) and adapted to growth in media containing serum in a manner similar to that described in Example 1. The process is outlined in FIG. 5B.

First, one vial of the MDCK Clone Subclone 1-D (frozen at passage 5 since subclone, P85 in total) was thawed and inoculated into a T75 flask containing 35 ml of Dulbecco's Modified Eagle's Medium/Ham F12 (DMEM/F12) with L-glutamine and 10% fetal bovine serum (FBS, Defined), and incubated at 37° C. with 5% $CO_2$ for 3 days. On day 3 the cells were passaged to a T225 flask (Passage 7/P87). Next, the MDCK Subclone D cells were adapted in serum-free medium MediV 105 for 5 passages.

At passage 5 in MediV 105, cells were frozen as an accession bank. In addition, one flask of cells (clone 1-D) was set up to check cell stability in MediV 105 serum free medium. SF MDCK Subclone D cells started dying after 8 passages in MediV 105 serum free medium.

In addition, serum MDCK clones 1, 55, 56, 57, and 58 and subclones 1-A, 1-B (P5/P85), and C were adapted to MediV 105 serum free medium. First, one vial of each serum MDCK clones 1, 55, 56, 57, and 58 and subclones 1-A, 1-B (P5/P85), and C were thawed into a T75 flask containing 35 ml of 10% FBS DMEDM/F12 medium and incubated at 37° C. with 5% $CO_2$ for 3 days. The cells were trypsinized and seeded into a new T225 flask at $5 \times 10^4$ cells/ml seeding density. On day 3 after seeding, cells were passaged to a T75 flask in serum containing growth medium.

For each of the passages in DMEM/F12 with L-glutamine and 10% FBS in a T75 or T225 flask, the procedure was as follows. Cells were washed two times with Dulbecco's Phosphate Buffered Saline without $Ca^{++}$ and $Mg^{++}$ (DPBS), and 3 ml (for the T75 flask) or 7.5 ml (for the T225) of TrypLE were added to the cells. The cell monolayer was incubated and allowed to release for 15-20 minutes, at which time 3 ml (for T75) or 7.5 ml (for T225 flask) of 10% FBS DMEM/F12 with L-glutamine was added to neutralize the TrypLE activity. The cells were then counted by Cedex cell count, and the amount necessary to inoculate $5 \times 10^4$ cells per ml was transferred to a T75 flask or T225 flask containing sufficient media to bring the volume to 35 ml (T75) or 100 ml (T225) of 10% FBS DMEM with L-glutamine, and incubated as above for 3 or 4 days.

Next, each of the clones in T75 flasks (3 passages in serum medium after thawing) was adapted for growth in MediV 105 serum free medium. Cells from the T75 flasks were passaged for 3 passages in T75 flasks containing 35 ml of MediV 105. At the fourth passage, the cells were passaged to a T225 flask containing 100 ml MediV 105. Cells from the T225 flask were seeded to 2 or 3 T225 flasks based on cell count for the fifth passage. On day 3 or day 4 post seeding, clones 1, 56, and 57, and subclones 1-A, 1-B, 1-C, and 1-D were frozen as an accession bank. Clones 55 and 58 were each passaged an additional time in serum free medium before the cells were banked.

For each of the passages in MediV 105 serum free media in a T75 or T225 flask, the procedure was as follows, for the first passage to MediV 105, spent medium from the T75 flask with cells at passage 3 after vial thawing was removed, the cells were washed with DPBS, 3 ml of TrypLE was added, and the cells were incubated and allowed to release for 15-20 minutes. Then 3 ml of lima bean trypsin inhibitor solution (Worthington) were added to neutralize the TrypLE, and the cells were counted by Cedex cell counter. The amount of cells necessary to inoculate $5 \times 10^4$ cells per ml of media was transferred to a T75 flask containing 35 ml of MediV 105. All flasks were incubated at 37° C. with 5% $CO_2$ for 3-4 days at which time the cells were again enzymatically detached as described above except using 2.5 ml (for T75) or 5 ml (for T225) of TrypLE, then 2.5 ml (for T75) or 5 ml (for T225) of lima bean trypsin inhibitor solution used to stop TrypLE activity, and cell suspensions were transferred to flasks with fresh serum free medium. All seedings were calculated to inoculate $5 \times 10^4$ cells per ml of media.

For the banking of each clone/subclone the procedure was as follows: Cells from the multiple flasks were trypsinized, pooled, and trypsin neutralizing solution was added. The cells were then mixed and counted. The cells were centrifuged, and resuspended in saved spent medium to make $1 \times 10^7$ cells/ml cell suspension. Next, 2× freezing medium (MediV 105 with 15% v/v dimethyl sulfoxide, and an equal volume of spent medium) was added, the cells were mixed thoroughly, and 1 ml aliquots were placed into 2 ml size cryovials. These vials were designated as SF MDCK accession banks. The cells were frozen at −60° C. in Nalgene freezer containers, and then transferred to storage in liquid nitrogen. FIG. 5 is a flow chart of the entire selection and adaptation process for clone 1 and subclone 1-B.

Along with banking, a T75 flask of each serum free-adapted clone was set up for cell growth stability in serum free medium and virus infectivity study. In the study, cells were seeded at $5 \times 10^4$ cells per ml of media and passaged every 3 or 4 days after seeding. Clones 56 and 57 started dying at sixth passage in MediV 105.

Each of the other clones and subclones were continued to be cultured in MediV 105. At Passage 9 or 10, 5 T75 flasks for each clone were set up for virus infection. The clones were infected with reassortants of A/New Calcdonia, A/Hiroshima, B/Malaysia and A/Vietnam at MOI 0.001, using DMEM/F12 with 4 mM glutamine+500 mU/ml TPCK trypsin as the post infection media. Viruses were harvested at 3 and 4 days post infection and stabilized with 10× sucrose phosphate buffer. Virus titers were determined by FFA assay as described below in Example 4. The results of these experiments (data not shown) showed that the subclones of clone 1 produced more virus than the other tested MDCK cell clones. Accordingly, subclones 1-A, 1-B, and 1-C were selected for further experiments to assess cell growth in MediV 105. Results of this experiment are shown as FIG. 2. As shown in FIG. 2, each of subclones 1-A, 1-B, and 1-C exhibited essentially similar growth characteristics.

In addition, subclones 1-A, 1-B, and 1-C were retested for virus infectivity at passage 12. 9×T75 flasks for each subclone were infected with influenza viruses under the same conditions as at passage 9, described immediately above, in duplicate (2 T75 flasks per clone per virus strain. Results from this experiment are presented as FIG. 3. As shown in FIG. 3, each of the subclones supported growth of the tested viruses to relatively high titer, and none of the different subclones supported the highest titer of each tested virus strain.

Finally, to assess the effects of the MediV 105 medium on virus growth, virus infectivity was assessed for subclones 1-A, 1-B, and 1-C in both MediV 105 and OptiPro™ medium (GIBCO), while subclone 1-D was tested in OptiPro™ media alone, as described above. Tabular results from each of these virus infectivity experiments are presented as FIG. 4. As shown in FIG. 4, no significant difference in virus productivity was observed between the two media.

9.3 Example 3

Comparison of MDCK Cell Growth in MediV 105 and M18M

This example describes the results of an experiment to assess the relative growth of MDCK cells in MediV 105 and M18M media. The formulations of MediV 105 and M18M are described in Example 10, below.

In these experiments, 1 vial of serum free-adapted subclone 1-A was thawed and inoculated into a T-75 flask containing either MediV 105 or M18M, respectively. The T-75 flasks were then placed in a 37 C incubator supplied with 5% $CO_2$ and the cells were allowed to grow under these conditions for 3 to 4 days. Cell growth rate and viability were monitored the end of incubation by trypsinizing the cells from the T-75 flasks followed by counting the total and viable cells using a Cedex cell counter or over the next 88 hours by Cedex and/or NucleoCounters.

Results from this experiment are presented as FIG. 6. As shown in FIG. 6, subclone 1-A was able to replicate in both MediV 105 and M18M. However, cells decreased in viability over time in M18M, while cell viability in MediV 105 remained relatively constant. In addition, the doubling times of the MDCK cells were calculated and are presented as FIG. 7. FIG. 7 indicates that the doubling time of MDCK cell subclone 1-A was 39 hours in MediV 105 and 36 hours in M18M.

9.4 Example 4

Comparison of MDCK Cell Growth on Different Microcarriers

This Example describes the results of experiments designed to assess the growth of MDCK cells in M18 media using different microcarriers. In particular, growth of MDCK cells was compared for the microcarriers cytodex 1, cytodex 3, cytopore 1, and cytopore 2 (GE Healthcare).

In the experiments, MDCK cell subclone 1-A was inoculated into a 125 ml flask containing M18 media. Next, 2 g/L cytodex 1, cytodex 3, cytopore 1, or cytopore 2, respectively, was added to each flask. The density of unattached MDCK cells was determined at 30 and 60 minutes post-inoculation as shown in FIG. 8. As seen in FIG. 8, the MDCK cells attached quickly to each of the different microcarriers, and ultimately attached better to the cytopore microcarriers than the cytodex microcarriers.

In addition, the cells were grown for approximately 5 days in M18 in the presence of the different microcarriers (30 ml microcarrier w/v in 125 ml media shaken at 120 RPM), and the total cell density determined daily by trypsinization followed by Cedex counting. Results from this experiment are presented as FIG. 9. As shown in FIG. 9, the cytodex microcarriers yielded greater cell densities relative to the cytopore microcarriers. Further, cytodex 3 yielded a greater cell density than cytodex 1.

9.5 Example 5

Replication of Influenza Viruses in MDCK Cells

T-75 flasks were seeded at $5 \times 10^4$ cells/mL (35 mL of DMEM+10% FBS+4 mM glutamine) and grown in an incubator maintained at 37° C. and 5% $CO_2$ for 3 days. Cells in one of these T-flasks were trypsinized with trypsin EDTA and counted using the Trypan-Blue Exclusion method. The remaining T-flasks were then infected as follows. The growth media was aspirated off and cells washed twice with 10 mL DPBS (no $Ca^{2+}/Mg^{2+}$) per flask. The amount of virus to infect each T-flask at the desired multiplicity of infection (MOI) of (e.g., 0.01 to 0.001) was determined as per the equation below:

$$\text{Amount of virus(mL)} = \frac{\text{Total Cells per flask} * MOI}{10^{\wedge}(\log TCID50/\text{mL})}$$

MOI being defined as the virus particles per cell added

The required amount of virus was then added to 35 mL of post infection medium in each T-flask. (DMEM+4 mM glutamine+500 mU/mL TPCK trypsin). The T-flasks were then incubated at 33° C., 5% $CO_2$ and samples taken each day for 6 days. One tenth volume of sample volume of 10×SP was added to each sample as a stabilizer and the samples were stored at <−70° C. prior to testing for infectivity.

The concentration of virus present in each sample was determined according to a median tissue culture infectious dose ($TCID_{50}$) assay that measures infectious virions. Briefly, MDCK cells were grown to confluent monolayers in 96-well microtiter plates and a serial dilutions of ca/ts influenza virus sample was added. The samples in the MDCK cell assay plate were typically diluted to final dilutions of $10^{-4}$ to $10^{-10}$. The wells in columns 1-5 and 8-12 contained virus-diluted sample and wells in columns 6-7 received only virus diluent and served as cell controls. This format produced two data points (n=2) for each sample dilution per plate. Replication of virus in the MDCK cells resulted in cell death and cytopathic effect (CPE). It also released progeny viruses into the culture supernatant. The progeny virus infected other cells, repeating the infection and resulting in the eventual destruction of the monolayer. Infection of monolayer cells lasted for a period of six days at 33±1° C. in a $CO_2$ environment. The plates were then removed from the incubator, the media in the wells discarded, and 100 μl of MEM/EBSS+1× non-essential amino acids+2 mM glutamine+penicillin/streptomycin+MTT was added to each well. The plates were incubated for 3-4 hrs at 37° C. 5% CO2 and the number of wells showing CPE was determined by visual inspection of the color formed in each well (yellow/orange signifies CPE wells and solid purple signifying no CPE). The number of wells showing CPE in each half plate was used to calculate the titer ($\log_{10}$ TCID$_{50}$/mL) based on the Karber modification of the Reed-Muench method.

9.6 Example 6

Fluorescent Focus Assay for Viral Growth

MDCK cells were grown in 96 well black plates over 4 days in DMEM/EBSS+1× non-essential amino acids+2 mM glutamine+PEN/Strep. Each well was then infected with the serially diluted viral samples (e.g., ca/ts influenza B-strains (B/Hong Kong/330/01 and B/Yamanashi/166/98)) and incubated for approximately 20 hrs at 33±1° C. in a $CO_2$ environment. The virus infected plates were fixed and immunostained as follows to determine the virus titer of the samples. The medium containing virus was removed from each plate and the plates washed once with 200 μl/well with DPBS (no Ca2+/Mg2+) followed by fixation in 200 μl/well of cold 4% (v/v) formalin in PBS for 15 minutes. The plates were washed twice with 200 μl/well of DPBS (no $Ca^{2+}/Mg^{2+}$) followed by incubation of the cells with primary antibody specific for either A strains or B strains. The primary antibodies were diluted to the desired dilution in 0.1% saponin, 1% BSA in PBS. After incubation for an hour, the primary antibody was removed, cells were washed thrice with 0.1% Tween 20 in PBS, and the wells were incubated with fluorescent dye conjugated secondary antibody (e.g., rabbit anti sheep labeled with FITC) prepared to the desired dilution in 0.1% saponin, 1% BSA in PBS. After washing twice as described above and blot drying with paper towels the wells with fluorescent staining were visualized daily using a fluorescence microscope and the images were taken daily using SPOT program.

9.7 Example 7

Assays for Testing MDCK Cells for Karyology, Tumorigenicity, and Adventitious Agents This example describes representative assays suitable for testing MDCK cells for karyology, tumorigenicity, and the presence of adventitious agents.

9.7.1. Karyology Testing

Briefly, MDCK cells for testing are grown in T-225 flasks, maintained and subcultured as described above. When the cells are thought to have enough mitotic cells, the cells are harvested for mitotic analysis. The cells are then treated with colcemid (0.02 μg/mL) for 150 minutes at 37° C. The cells are then harvested by trypsinization, and centrifuged for 5 minutes at 200×g. The supernatant is aspirated off and the cells resuspended in prewarmed hypotonic solution and incubated at 37° C. for 10 minutes. The swollen cells are pelleted by centrifugation and then fixed by incubation in Carnoy's solution (3:1 methanol:glacial acetic acid) at room temperature for 40 minutes. The cells are again centrifuged and washed at least twice with Carnoy's fixative. After the last centrifugation, the cells are resuspended in 1 to 3 ml of fresh fixative to produce an opalescent cell suspension. Drops of the final cell suspension are placed on clean slides and air dried.

Cells are stained by addition of Wright's stain solution in phosphate buffer to the slides and incubating for 7-10 minutes. The slides are then washed with tap water after 7-10 minutes and then air dried. The cells are scanned with low power objectives (10×) to find cells in the metaphase stage of cell division and the chromosomes of cells in metaphase are analyzed via a high power oil immersion lens (100×). About 100 cells in metaphase are analyzed for cytogenic abnormalities and chromosome count. About 1000 cells are scanned to determine polyploid frequency and mitotic index (percent of cells under going mitosis).

9.7.2. Sterility Testing: Bacteriostatic, Fungistatic and Four Media Sterility Bacteriostatic and Fungistatic test determine whether there is any inhibitory effects to the growth of control organisms (e.g., *Bacillus subtilis, Candida albicans, Clostridium sporogenes, Staphylococcus aureus, Pseudomonas aeruginosa, Aspergillus Niger*) in a test sample. Briefly, the test article is inoculated into three tubes of TSB (soybean-casein digest medium), four tubes of THIO (fluid thioglycollate medium), two tubes of SAB (Sabourand Dextrose Agar) and one tube of PYG (peptone yeast extract). Each control organism inoculum containing less that 100 cfu of control organism is then inoculated into the appropriate media type. Positive controls may consist of *Bacillus subtilis* in TSB and THIO, *Candida albicans* in TSB and SAB (at 20-25° C. and 30-35° C.), *Clostridium* sporogenes in THIO and PYG, *Pseudomonas aeruginosa, Staphylococcus aureus* and *Aspergillus niger* in THIO and/or TSB. The negative control is sterile PBS. The media are incubated for 3-5 days and checked for growth of organisms.

To test whether a test culture meets sterility requirements defined in USP 26, EP and 21CFR610.12, the test culture is inoculated in two tubes of TSB (soybean-casein digest medium), two tubes of THIO (fluid thioglycollate medium), three tubes of SAB (Sabourand Dextrose Agar) and two tubes of PYG (peptone yeast extract). The media are incubated at appropriate temperatures (SAB slants are incubated at two temperatures) and all tubes observed over a 14 day period with the tubes checked on third/fourth or fifth day, seventh or eight day and fourteenth day of testing. Any test article inoculated tubes which appear turbid are plated out and gram stains are performed on the plate to determine the gram stain type of the organism(s) contained in the test sample. Negative controls are sterile PBS.

9.7.3. *Mycoplasma*/Mycoplasmastasis Assay

The cells are expanded and cultured in T-flasks as explained above. Cell lysates at a concentration of $5 \times 10^5$ cells/mL are prepared and frozen at −70° C. The test article is then tested for ability to inhibit growth of Mycoplasmapneumoniae, *Mycoplasma orale* and *Mycoplasma hyorhinis* either in agar broth/plates and/or in VERO cells.

For the agar isolation assay, the test article is tested either spiked or unspiked on agar plates or broth bottles. The test article is spiked with Mycoplasmapneumoniae and *Mycoplasma orale* to achieve a dilution of 10 to 100 cfu/0.2 mL (for the Agar test) and 10 to 100 cfu/10 mL (for the semi broth assay). A portion of the test sample is not spiked. 4 semi solid broth bottles are inoculated with 10 ml each of spiked (2 bottles) or unspiked (2 bottles). One bottle each of spiked/unspiked is incubated either aerobically or anaerobically at appropriate temperatures. 10 type A agar plates and 10 type B agar plates are inoculated with each spiked sample or unspiked sample. Half the type A agar plates and type B agar plates are incubated either aerobically or anaerobically at appropriate temperatures. Uninoculated mycoplasma semi-solid broth serves as the uninoculated negative control. All broth bottles are observed for 21 days. Each broth bottle (with exception of uninoculated negative control) is subcultured on days 3, 7 and 14 onto Type A agar plates or Type B agar plates (10 plates each, 0.2 mL/plate) and incubated under the same conditions as the appropriate bottle. They are examined once a day for 21 days.

For the enhanced VERO cell culture assay, the test article is tested spiked or unspiked. The test article is spiked with *M. orale* and *M. hyorhinis* at a concentration of 10-100 cfu/0.2 mL. The spiked test articles, unspiked test articles, positive controls and negative controls are each inoculated onto T-75 flasks of VERO cell cultures. After 3-5 days of incubation, the cells from each flask are scraped and snap frozen. Two tenths of one mL of cell lysate from each flask is inoculated into each of well of a six well plate containing VERO cells. In addition, positive and negative controls are inoculated into appropriate wells of six well plates containing VERO cells. After 3-5 days, the cells are fixed and stained with DNA binding HOECHT dye and evaluated for presence of mycoplasma.

9.7.4. Tumorigenicity Test in Nude Mice

Evaluation of tumor formation in nude (nu/nu) athymic mice is performed as follows. Briefly, about two hundred thirty athymic mice (4 weeks old) are each injected subcutaneously with 0.2 mL (1×10$^7$ cells/mice) of either positive control (HeLa cells), negative control (Phosphate buffered Saline (PBS)) or the test cells (MDCK cells). The animals are randomized before injection and all mice are injected using a 22 gauge needle on the same day. All animals are observed every working day and the injection site is palpated twice a week for lesion development for a period of eighty four days. Each lesion is measured and the animals are held as long as there is no visible increase in size of the lesion, for a maximum of 6 months. Animals that appear moribund will be euthanized. These animals and all mice surviving to the end of 6 month observation period are sacrificed and necropsied. The injection site, lungs, scapular lymph nodes and gross lesions are analyzed by histopathological methods.

9.7.5. Additional Assays

Other exemplary PCR and/or antibody-specific tests for available viral agents are conducted, as shown in Table 4, below.

TABLE 4

Additional Testing Procedures

| General tests | PCR*/Ab specific |
|---|---|
| Sterility | AAV Types 1 & 2 |
| Mycoplasma | HCMV |
| Adventitious agents in vitro (multiple cell lines) | EBV |
| Adventitious agents in vivo | HSV |
| PERT | Hepatitis A, B & C |
| Co-cultivation | HHV 6, 7 & 8 |
| Karyology | HIV 1 & 2 |
| Electron microscopy | HPV |
| Tumorigenicity using intact cells | HTLV I & II |
| Oncogenicity using cellular DNA | Polyomavirus (BK and JC viruses) |
| Oncogenicity using cellular lysate | Circovirus |
| Bovine viruses per 9CFR | Canine Parvovirus |
| Porcine viruses per 9CFR | Canine distemper |
| | Adenovirus |
| | SV40 |

9.8 Example 8

Process and Formulation of Vaccine Material

Use of a highly scalable microcarrier technology, similar to that used for the production of the currently licensed Polio vaccine, can be applied to the production of influenza in MDCK cells, as discussed in Example 4, above. Spherical beads made of dextran support excellent growth of MDCK cells and in 2 to 10 L bioreactors. Parental MDCK cells grown in MediV 105 or OptiPro™ medium were found to be capable of growing on Cytodex 3 microcarriers to a density of 2×10$^6$ nuclei per mL in batch mode in both spinner flasks and MDCK cells have been grown to >2.5×10$^6$ cell/mL in bioreactors up to 10 L scale.

These MDCK cells (or similar non-adherent MDCK cells) are tested for production of vaccine influenza strains to high titer in a serum-free process and compared to the productivity obtained using serum grown cells in T-flasks. For clinical manufacturing, influenza virus is produced in MDCK cells at the 20 L or 150 L scale, while commercial scale production utilizes bioreactors up to about 2,500 L. FIG. 10 outlines one process that may be used for cell culture scale up to commercial production levels. The working cell bank is first expanded sequentially from a T-75 flask to T-225 flasks to 1 liter spinner flasks to a 20 liter then 300 liter bioreactors which are finally expanded to a 2500 liter bioreactor. When the optimal cell density is obtained the culture is inoculated with the vaccine strain. The virus is then bulk harvested from the culture supernatant. Example 12 details the implementation of single use bioreactors (SUBs) for the production of high titer viral material, which may be used for the production of vaccine material.

The purification process for cell culture based influenza vaccines is modeled on purification of egg-based influenza vaccines (see, e.g., PCT Publication WO 05/014862 and PCT Patent Application PCT/US05/035614 filed Oct. 4, 2005). The purification of viral vaccine materials from cells may include any or all of the following processes, homogenation, clarification centrifugation, ultrafiltration, adsorption on barium sulfate and elution, tangential flow filtration, density gradient ultracentrifugation, chromatography, and sterilization filtration. Other purification steps may also be included. For example, crude medium from infected cultures or virus harvest can first be clarified by centrifugation at, e.g., 1000-2000×g for a time sufficient to remove cell debris and other large particulate matter, e.g., between 10 and 30 minutes. Alternatively, the medium is filtered through a 0.8 μm cellulose acetate filter to remove intact cells and other large particulate matter. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus may be concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large scale commercial applications, virus is elutriated from density gradients using a zonal-centrifuge rotor operating in continuous mode.

A feature which may be included in the purification of viral vaccine materials from cells is the use of Benzonase®, a non-specific endonuclease, early in the process. While MDCK cellular DNA does not pose an oncogenic risk based on studies evaluating oncogenicity of cellular DNA, Benzonase® treatment would virtually eliminate any potential or hypothetical risk. In one purification process, following Benzonase® treatment, the material is clarified by direct flow filtration (DFF) which will also remove any residual intact mammalian cells in the bulk material. The filtered bulk is then concentrated by tangential flow filtration (TFF) prior to further purification steps. Purification methods including affinity chromatography as well as ion-exchange chromatography and/or hydroxyapatite which, have worked well for other viral systems are useful for cell culture based influenza vaccine production. The highly purified viral material obtained by the process developed is then utilized in the production of vaccine material. For example, for use in a live attenuated vaccine production (e.g., FluMist®) the viral material may be subjected to a buffer exchange by filtration into a final formulation followed by a sterilization step. Buffers useful for such a formulation may contain 200 mM sucrose and a phosphate or histidine buffer of pH 7.0-7.2 with the addition of other amino acid excipients such as arginine. If necessary for stabilization, protein hydrolysates such as gelatin (e.g., porcine, avian, piscine gelatin) may also be added. Ideally the vaccine material is formulated to be stable for an extended storage time. One method which may be utilized to extend storage time is spray drying, a rapid drying process whereby the formulation liquid feed is spray atomized into fine droplets under a stream of dry heated gas. The evaporation of the fine droplets results in dry powders composed of the dissolved solutes (see, e.g., US Patent Publication 2004/0042972). Spray drying offers the advantages of ease of scalability and manufacturing cost as compared to conventional freeze-drying processes. Alternatively, the vaccine material is formulated to be stable as a refrigerator stable liquid formulation using methods known in the art. For example, methods and compositions for formulating a refrigerator stable attenuated influenza vaccine are described in PCT Patent Application PCT/US2005/035614 filed Oct. 4, 2005.

In-process characterization steps are incorporated into the purification scheme to monitor the production. Characterization steps which may be utilized include but are not limited to the Fluorescent Focus Assay (described as Example 6, and known in the art, see e.g., Stokes et al., 1988, J Clin Microbiol. 26:1263-6) which uses a simple antibody binding and fluorescent staining method to determine virus infectivity. Total protein and DNA determination which may be performed using numerous methods known to one of skill in the art are used to determine the percent of the initial impurities remaining. The specific activity of the preparation may be determined by calculating the viral infectivity per quantity of vaccine (e.g., infectivity/mg).

Figure 11A:
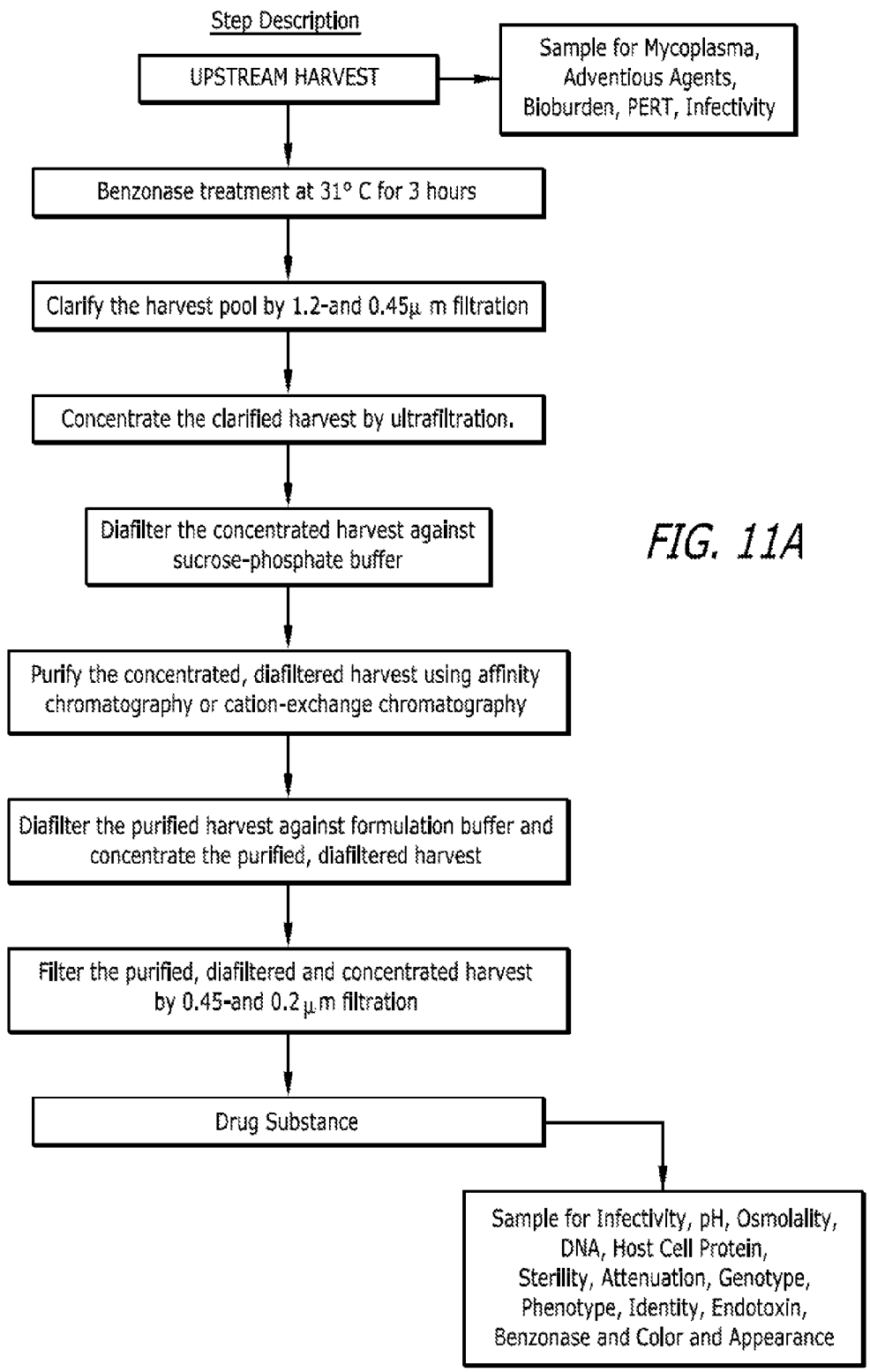
Figure 11B:
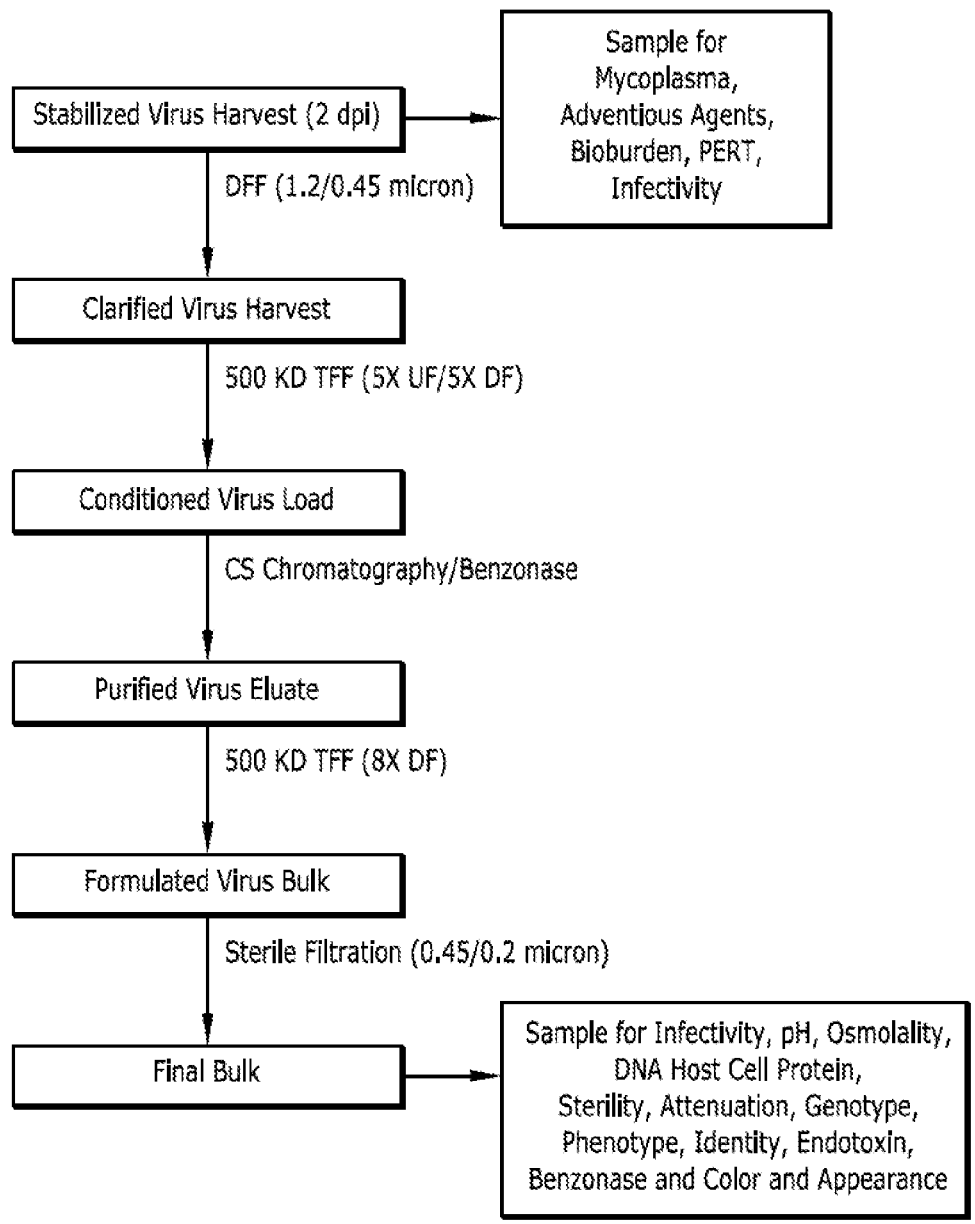

Outlined in FIG. 11A is one purification process that may be used. Briefly, the monovalent influenza viral harvest is stabilized with a suitable buffer (e.g., sucrose-phosphate buffer). Benzonase, a non-specific endonuclease, is then added to the stabilized viral harvest to break down DNA to less than 300-basepair fragments. After Benzonase treatment, the virus harvest is subjected to filtration to remove any remaining intact MDCK cells and most cellular debris. In particular, Direct Flow Filtration (DFF) can be utilized. Various filter membranes with different pore sizes, membrane compositions, and configurations (such as multimedia or single filter) and process parameters, including maximum flow rate and scale-up factor, are readily determined. The clarified virus harvest is then concentrated by Tangential Flow Filtration (TFF) using ultrafiltration membranes and the concentrated virus is then diafiltered against a suitable buffer (e.g., sucrose-phosphate buffer). The concentrated, diafiltered harvest is then subjected to column chromatography or membrane chromatography. Affinity chromatography and ion-exchange chromatography may be used to further remove MDCK cell protein and DNA. The chromatographically purified virus harvest then concentrated and diafiltered into a formulation buffer and, finally, subjected to sterile filtration. Outlined in FIG. 11B is an alternative purification process that may be used which combines the Benzonase® step with affinity chromatography. The use of such a process can reduce downstream processing steps. Briefly, the monovalent influenza viral harvest is stabilized with a suitable buffer (e.g., sucrose-phosphate buffer). The stabilized virus is clarified by filtration, for example by Direct Flow Filtration (DFF) using 1.2- and 0.45-μm filters. The clarified virus is then conditioned/concentrated by TFF using ultrafiltration membranes and the concentrated virus is then diafiltered against a suitable buffer (e.g., sucrose-phosphate buffer) using, for example 500 KD TFF (5×UF/5×DF). The conditioned virus is then subjected to on column Benzonase® treatment and the purified virus eluate is then concentrated and diafiltered into a formulation buffer using for example, 500 KD TFF and 8×DF processes. The formulated virus bulk is then sterile filtered, for example through 0.45- and 0.2-1 μm filters.

9.8.1. Cellufine Sulfate Chromatography

It was determined that MDCK DNA contains a Benzonase® resistant fragment of ~12 kB and that was not removed by TFF or ultracentrifugation using a sucrose density gradient (data not shown). As described above, chromatography is utilized to ensure removal of all contaminants Cellufine Sulfate chromatography resin consists of sulfate ester covalently bonded on the 6-position of cellobiose and attached to a cellulose bead. The resin mimics the of heparin or dextran sulfate. A column chromatography using Cellufine Sulfate (CS) was tested and demonstrated to efficiently remove the contaminating DNA band. Briefly, a 2.6×2 cm (10 mL) column, was equilibrated in buffer A (1×SP (218 mM sucrose, 11 mM potassium phosphate), pH 7.2) and the TFF-purified virus (A/New Calcdonia reassortant) was loaded. The column was washed with 5 column volumes of buffer A and eluted with a gradient of 0-100% buffer B (1×SP+1 M NaCl, pH 7.2). The flow rate was maintained at 3 mL/min. The OD profile is shown in the left panel of FIG. 12A. Shown in Table 5 are the DNA content, total HAU and the FFA infectivity of the starting material, the flow through and the elution fractions from the CS column.

TABLE 5

Cellufine Sulfate Chromatography

| Sample | Total DNA (μg) | Total HAU (Log$_{10}$/mL) | FFA Infectivity (per mL) |
| --- | --- | --- | --- |
| TFF/UF material | 26.7 | 5.8 | $1.5 \times 10^{10}$ |
| Flow Thru | 12.7 | 4.0 | $6.5 \times 10^{7}$ |
|  | (47%) | (1.6%) | (0.4%) |
| Elute | 8.5 | 5.75 | $1.1 \times 10^{10}$ |
|  | (32%) | (88%) | (70%) |

Figure 12A:
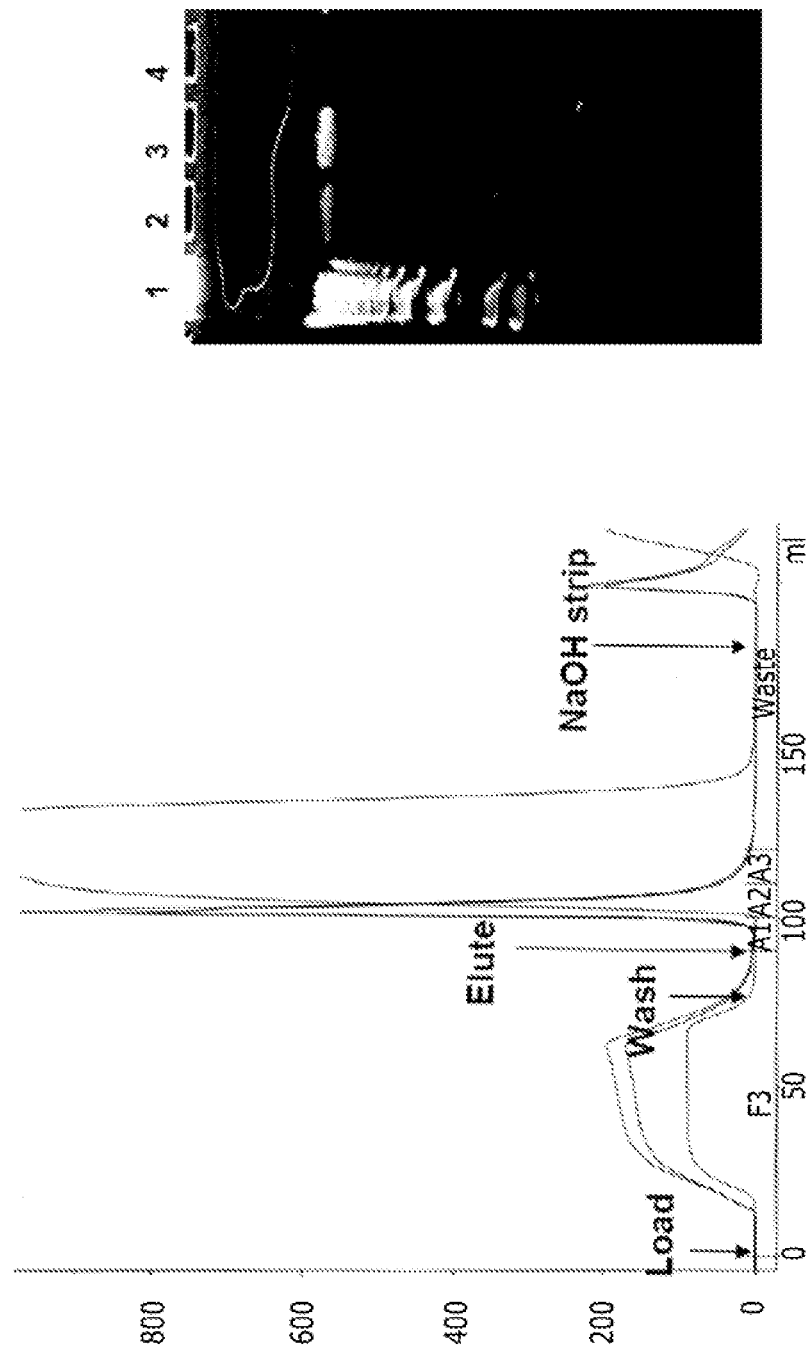

The starting material, the flow through and the elution fractions from the CS column were analyzed by agarose gel electrophoresis (FIG. 12A, right panel). The DNA contaminate is present in both the starting material (lane 2) and the flow through (lane 3) but is absent in the material eluted from the column (lane 4). These data indicate that the use of this affinity chromatography resin is more effective than ultracentrifugation alone at removing contaminants from culture media and host cells.

9.8.2. On Column Benzonase® Treatment

Figure 12B:
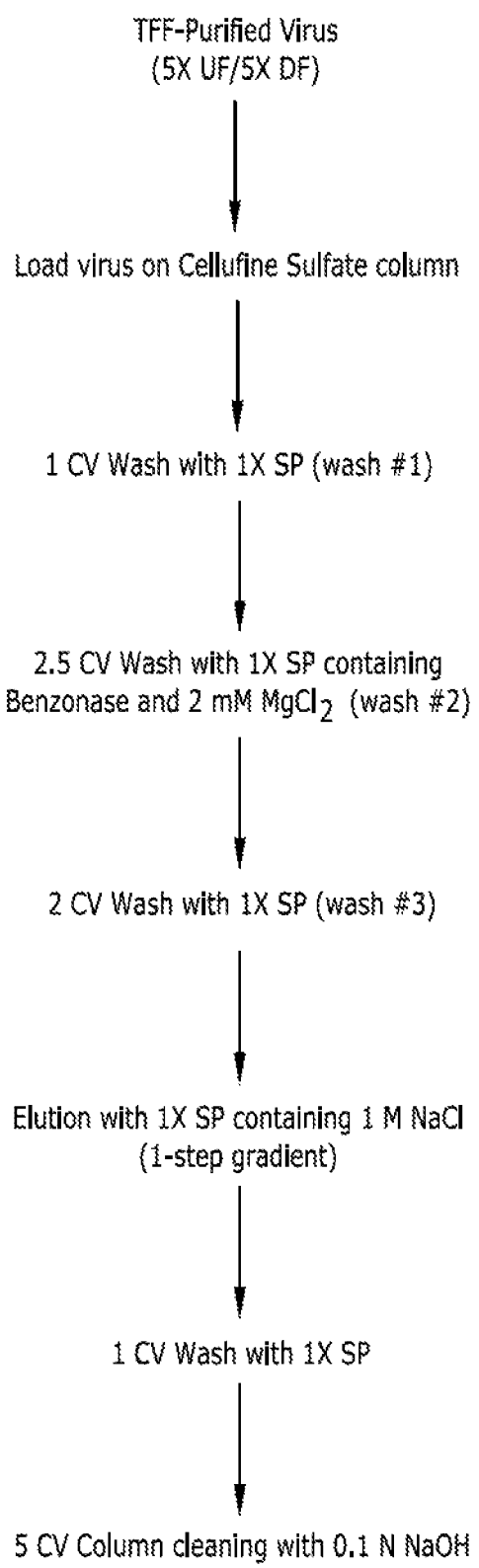

To reduce handling steps and enhance purity the Benzonase® treatment may be combined with Cellufine Sulfate chromatography. The scheme for degradation of the MDCK dsDNA using Benzonase® On-Column Treatment is shown in FIG. 12B.

The details of the process are as follows: The entire process is carried out at 22° C. (room temperature). TFF-purified virus is warmed up to 22-24° C. before performing chromatography as needed. Loading on the column is based on total virus infectivity unit per FFA assay. Target loading on the column is 9-9.5 $\log_{10}$ FFU per mL of column volume. The flow rates for equilibration, loading, washings and elution remain same (155 cm/hr) except the flow rate is reduced as shown in Table 6 while washing with 1× SP buffer containing Benzonase®. The column (1×15 cm) is equilibrated with 1× SP (218 mM sucrose-11 mM potassium phosphate, pH 7.0±0.2) until the conductivity and pH reach 2-3 mS/cm and 7.0±0.2, respectively. The virus is loaded on the column and the flow through is collected. After completion of loading, the column is washed (wash #1) with 1 column volume (CV) of 1× SP and the wash is collected together with the flow through fraction. The column is then washed (wash #2) at different flow rates (ranging from 0.33, 0.46, 0.65, 0.98, and 1.3 mL/min for each experiment performed by repeating steps 1-3 with the same virus load material) with 2.5 CV of 1× SP containing 2 mM $MgCl_2$ and 50 units of Benzonase® per mL of 1× SP. After wash #2, the column is washed with another 2 CV of 1×SP (wash #3). The virus is eluted from the column using 1× SP containing 1 M NaCl. The eluted material is collected as soon as the $A_{280}$ nm value reads 5 mAU and the collection is continued until $A_{280}$ nm absorbance value returns to 5 mAU. The column is cleaned with 5 CV of 0.1 N NaOH and left in base until it is used again. The data for the chromatography run is captured in the data sheet at the end of this protocol. Multiple copies of the data sheet may be made for each chromatography run performed.

TABLE 6

Benzonase ® Contact Time with Virus and Flow Velocity for Runs 1-5

| Run # | Wash Volume (wash #2) | Flow Rate (mL/min) | Contact Time of Benzonase with Virus (min) | Flow Velocity (cm/hr) |
|---|---|---|---|---|
| 1 | 2.5 CV | 0.33 | 102 | 25 |
| 2 | 2.5 CV | 0.46 | 73 | 35 |
| 3 | 2.5 CV | 0.65 | 51 | 50 |
| 4 | 2.5 CV | 0.98 | 34 | 75 |
| 5 | 2.5 CV | 1.3 | 26 | 100 |

Residual MDCK dsDNA in the eluted chromatography fraction is quantitated using the PicoGreen quantitation assay kit as described by Invitrogen. Fluorescence is measured using the Molecular Devices Gemini EM fluorescence plate reader and the amount of dsDNA degradation is calculated using SoftMax Pro version 4.8 software.

Table 7 summarizes the purification yields for several developmental runs using both the Benzonase® treatment in bag and the Benzonase® treatment on column.

9.9 Example 9

Preclinical Animal Models

The ferret is a robust animal model used to evaluate the attenuation and immunogenicity of attenuated influenza vaccines and component vaccine strains. The performance of cell derived influenza strains produced from the MDCK cell culture are compared to the same strains produced in eggs. Head to head comparison of these materials in controlled studies enables a high level of assurance of the comparability of these viral products.

In order to evaluate the ability of the two vaccines to infect or achieve a "take" in the ferret, animals are lightly anesthetized and inoculated intranasally with either the cell or egg produced viral preparations. Nasal wash material is collected at several time points following inoculation and the quantity of virus is evaluated by one of several available methods in order to evaluate the kinetics and extent of viral replication in the animals' upper respiratory tract. Experiments are performed with a range of doses and include multiple strains and different trivalent mixtures to generalize the relative infectivity of cell culture grown strains to egg produced strains. These same studies are also used to evaluate the immunogenicity of the influenza strains, a property that is inherently linked to the ability of the virus to initiate infection. Animals are bled and nasal washes are harvested at various points (weeks) post inoculation; these specimens are used to assess the serum antibody and nasal IgA responses to infection. The culmination of these data, infectivity, serum antibody and mucosal antibody responses, will be used to compare and evaluate the relative infectivity of the cell-produced vaccine to the egg produced vaccine. The most likely outcome is predicted to be that the cell and egg produced vaccine strains have similar infectivity and immunogenicity. If the cell derived vaccine appeared to be more infective or more immunogenic than the egg-derived product, further studies evaluating the possibility of lower dosage are performed.

TABLE 7

Summary of TVCC-1 Downstream Process

| | Dev Run | | | | | | | | |
|---|---|---|---|---|---|---|---|---|---|
| | Dev 2 | Dev 3 | Dev 4 | Dev 5 | Dev 6 | Dev 7 | Dev 8 | Dev 9 | CTM #2 |
| Strain | A/Wis | A/Wis | A/NC | B/Mal | B/Mal | A/NC | A/Wis | B/Mal | B/Mal |
| Harvest (hr) | 60-65 | 60-65 | 60-65 | 60-65 | 60-65 | 60-65 | 48 | 48 | 48 |
| Column | BPG200 | BPG200 | BPG200 | BPG200 | BPG100 | BPG100 | BPG100 | BPG100 | BPG100 |
| Loading (log10/mL) | 8.32 | 8.73 | 8.76 | 8.40 | 9.18 | 9.44 | 9.33 | 8.97 | 9.56 |

TABLE 7-continued

Summary of TVCC-1 Downstream Process

| | Dev Run | | | | | | | | |
|---|---|---|---|---|---|---|---|---|---|
| | Dev 2 | Dev 3 | Dev 4 | Dev 5 | Dev 6 | Dev 7 | Dev 8 | Dev 9 | CTM #2 |
| Process* | TVCC-1a | TVCC-1a | TVCC-1a | TVCC-1b | TVCC-1b | TVCC-1b | TVCC-1b | TVCC-1b | TVCC-1b |
| VH Titer (CCD) | 8.4 | 8.4 | 8.4 | 8.3 | 8.6 | 8.4 | 8.6 | 8.0 | 8.3 |
| VH Titer (PD) | 7.7^ | 8.4 | 8.6 | 8.1 | 8.3 | 8.3 | 8.4 | 7.9 | 8.3 |
| Final Titer | 8.3 | 8.5 | 8.5 | 8.5 | 8.9 | 8.6 | 9.2 | 9.0 | 9.7 |
| Overall Yield§ | 60.9% | 27.0% | 6.3% | 25.4% | 22.0% | 21.2% | 30.4% | 56.3% | 57.5% |
| VH DNA (ng/mL) | n/a | 7200 | 5480 | n/a | 5720 | 10800 | 3440 | 2070 | 2050 |
| Bulk DNA (ng/dose) PicoGreen | 76.7 | n/a | 36.4 | 31.9 | n/a | n/a | 0.4 | 0.3 | 0.06 |
| Bulk DNA (ng/dose) PCR | n/a | n/a | 0.92 | n/a | 0.23 | 0.18 | 0.032 | 0.164 | n/a |
| VH HCP (µg/mL) | 278 | 392 | 269 | 231 | 250 | 233 | 135 | 174 | 74 |
| Bulk HCP (µg/dose) | 1.10 | n/a | n/a | n/a | n/a | n/a | 0.13 | 0.29 | 0.14 |
| Benzonase ® (ng/mL) | 0.9 | n/a | 0.69 | 2.1 | 6.6 | 3.6 | 0.27 | 0.52 | LOD |

Note:* TVCC-1a: Benzonase ® treatment in bag; TVCC-1a: Benzonase ® treatment on column
^FFA assay based on Anti-NA instead of Anti-HA
§Based on VH-PD titer A number of immunogenicity and replication studies are performed in the ferret model to evaluate the cell culture-derived vaccines with a single unit human dose. Infection with ca/ts/att strains generally elicits strong and rapid antibody responses in ferrets. In addition, individual ca/ts/att strains are routinely tested and shown to express the attenuated (att) phenotype by replicating to relatively high titers in the nasopharynx but to undetectable levels in the lung of these animals. The impact of cell culture growth on these biological traits is also assessed. However, it is unlikely that any differences will be seen, since the au phenotype is an integral part of the genetic composition of these strains. The growth kinetics and crossreactivity of these strains is evaluated following administration of a single human dose in these animals. Live attenuated vaccines generated from egg derived material elicit serum antibodies that cross-react with multiple strains within a genetic lineage; and it is expected that a cell-derived vaccine will have the same capability.

These comparability evaluations should provide significant insight into potential biochemical and/or biophysical differences of the primary virus product and demonstrate the impact of these epigenetic differences on the performance of the ca/ts/att strains measured by first passaging the virus in human cells or animal studies. Based on the sequence information to date, there is no expected impact on the ca/ts/att strains immunogenic performance resulting from production on MDCK cells.

Ferrets are a well documented animal model for influenza and are used routinely to evaluate the attenuation phenotype and immunogenicity of ca/ts/att strains. In general, 8-10 week old animals are used to assess attenuation; typically study designs evaluate n=3-5 animals per test or control group Immunogenicity studies are evaluated in animals from 8 weeks to 6 months of age and generally require n=3-5 animals per test article or control group. These numbers provide sufficient information to obtain statistically valid or observationally important comparisons between groups. During most studies Influenza-like signs may be noticed, but are not likely. Ferrets do not display signs of decrease in appetite or weight, nasal or ocular discharge; observing signs of influenza-like illness is a necessary part of the study and interventions such as analgesics are not warranted. Other signs of discomfort, such as open sores or significant weight loss, would result in appropriate disposition of the animal following discussion with the attending veterinarian.

9.10 Example 10

Formulation of Serum Free Media for Cell Culture

This Example describes several serum free media formulations suitable for the culture of cells of the invention. While certain of such media have been described above, for completeness and ease of use, each is described in full below.

Formulation of Taub's Serum-Free Media:

Taub's media (Taub and Livingston, 1981, *Ann NY Acad. Sci.*, 372:406) is a serum-free media formulation that consists of DMEM/HAM F12 (1:1) containing 4.5 g/L glucose and 4 mM glutamine as the basal media formulation, to which the hormones/factors are added as indicated in Table 8.

TABLE 8

Hormones and growth factors added to serum-free media formulations

| Name of Component | Final Concentration |
|---|---|
| Insulin | 5 µg/mL |
| Transferrin | 5 µg/mL |
| Triiodothyronine ($T_3$) | $5 \times 10^{-12}$ M |
| Hydrocortisone | $5 \times 10^{-8}$ M |
| Prostaglandin $E_1$ | 25 ng/mL |
| Sodium Selenite | $10^{-8}$ M |

Taub's SFM is made fresh at the time of passaging or refeed by the addition of stock solutions of hormone supplements to SF DMEM/Ham F12 medium+4 mM glutamine+4.5 g/L glucose+$10^{-8}$ M sodium selenite. 100 mL of Taub's Media is made by addition of 100 µL of insulin stock (5 mg/mL) solution, 100 µL transferrin stock solution (5 mg/mL), 100 µl triiodothyronine (T3) stock solution ($5 \times 10^{-9}$ M), 5 µL of hydrocortisone stock solution ($10^{-3}$ M) and 500 µL of prostaglandin E1 stock solution (50 µg/mL) to basal DMEM/Ham F12 medium+4 mM glutamine+4.5 g/L glucose+$10^{-8}$ M sodium selenite. All stocks solutions are prepared as follows:

Insulin Stock Solution—

A 5 µg/mL stock solution is made by dissolving the appropriate amount of insulin in 0.01 N HCl. The solution is passed through a 0.2 micron sterilizing grade filter and aliquoted into Nalgene cryovial and stored at 4-20° C.

Transferrin Stock Solution—

A 5 mg/ml stock solution is made by dissolving the appropriate amount of transferrin in MilliQ water. The solution is passed through a sterilizing grade filter and then aliquoted into Nalgene cryovial and store <−20° C.

Triiodothyronine ($T_3$) Stock Solution—

A stock solution is made by dissolving the appropriate amount of T3 in 0.02 N NaOH to obtain a $10^{-4}$ M solution. This is stock solution is further diluted to a concentration of $5\times10^{-9}$ M stock solution with 0.02 N NaOH, passed through a sterilizing grade filter, aliquoted into Nalgene cryovial and stored at <−20° C.

Hydrocortisone Stock Solution—

A $10^{-3}$ M stock solution is made by dissolving the appropriate amount of hydrocortisone in 100% ethyl alcohol and aliquoted into Nalgene cryovials. The vials are stored at 4° C. for 3-4 months.

Prostaglandin $E_1$ Stock Solution—

A 50 μg/mL stock solution made by dissolving the appropriate amount of PGE1 in 100% sterile Ethyl alcohol and aliquoted into Nalgene cryovial and stored at <−20° C.

$Na_2$, $SeO_3$ Stock Solution—

A $10^{-2}$ M stock solution is made by dissolving the appropriate amount of sodium selenide in WFI water or MilliQ water. This is further diluted in water to a final concentration of $10^{-5}$ M passed through a sterilizing grade filter and stored at 4° C.

Ferric ammonium citrate (FAC) Stock Solution—

A 200 μg/L stock solution is made by dissolving the appropriate amount of ferric ammonium citrate in WFI water or MilliQ water passed through a sterilizing grade filter and stored at 4° C.

Tropolone Stock Solution—

A 250 μg/L stock solution is made by dissolving the appropriate amount of tropolone in WFI water or MilliQ water passed through a sterilizing grade filter and stored at 4° C.

Formulation Of Mediv Serum-Free Medias (MediV 101, 102, 103, 104, and 105):

Each MediV serum-free media formulation uses Taub's media as a basal media and adds supplements as follows:

MediV 101:

Taub's+2.5 g/L Wheat Peptone E1 from Organo Technie (cat no 19559). Wheat Peptone E1 is stored in water as a sterile 250 g/L stock solution.

MediV 102:

Taub's+100× chemically defined lipid concentrate from GIBCO BRL (cat no. 11905) added to a final concentration of 1×.

MediV 103:

Taub's+1× final concentration lipid concentrate from GIBCO+2.5 g/L Wheat Peptone E1 from Organo Technie.

MediV 104:

Taub's+1× final concentration lipid concentrate from GIBCO+2.5 g/L Wheat Peptone E1 from Organo Technie+5 μg/L EGF (multiple sources).

MediV 105:

Taub's without Transferrin, +1× final concentration lipid concentrate from GIBCO+2.5 g/L Wheat Peptone E1 from Organo Technie+5 μg/L EGF+0.2 μg/L Ferric ammonium citrate+0.25 μg/L Tropolone.

M-32:

MediV 105 having a glucose concentration of between 4 g/L and 4.5 g/L+Trace Element Solutions A, B and C (Table 9) at a final concentration of 1×. Optionally, M-32 is supplemented with an additional 4 g/L to 4.5 g/L of glucose (M-32+G)

MediV 107:

another serum-free medium based on MediV 105 including certain trace elements. The final formulation of MediV 107 in shown in Table 10.

Formulation of M18M Media:

in addition, M18M is another serum-free medium that can be used to culture cells of the invention. M18M is a serum free medium based on DMNSO-7 powder that contains supplements as set forth in Table 11, below.

TABLE 9

| 1000X Trace Element Solutions A, B and C | |
|---|---|
| Components | mg/L |
| Trace Elements Soln. A | |
| $CuSO_4 \cdot 5H_2O$ | 1.60 |
| $ZnSO_4 \cdot 7H_2O$ | 863.00 |
| Selenite•2Na | 17.30 |
| Ferric citrate | 1155.10 |
| Trace Elements Soln. B | |
| $MnSO_4 \cdot H_2O$ | 0.17 |
| $Na_2SiO3 \cdot 9H2O$ | 140.00 |
| $NH_4VO_3$ | 0.65 |
| $NiSO_4 \cdot 6H_2O$ | 0.13 |
| $SnCl_2$ (anhydrous) | 0.12 |
| Molybdic acid, Ammonium salt | 1.24 |
| Trace Elements Soln. C | |
| $AlCl_3 \cdot 6H_2O$ | 1.20 |
| $AgNO_3$ | 0.17 |
| $Ba(C_2H_3O_2)_2$ | 2.55 |
| KBr | 0.12 |
| $CdCl_2$ | 2.28 |
| $CoCl_2 \cdot 6H_2O$ | 2.38 |
| $CrCl_3$ (anhydrous) | 0.32 |
| NaF | 4.20 |
| $GeO_2$ | 0.53 |
| KI | 0.17 |
| RbCl | 1.21 |
| $ZrOCl_2 \cdot 8H_2O$ | 3.22 |

TABLE 10

| MediV 107 Formulation | |
|---|---|
| Component | g/L |
| Salts | |
| Calcium Chloride, Anhydrous | 0.1166 |
| Magnesium Chloride | 0.0286 |
| Magnesium Sulfate, Anhydrous | 0.0488 |
| Potassium Chloride | 0.3118 |
| Sodium Chloride | 6.8600 |
| Sodium Phosphate, Monobasic, Monohydrate | 0.0625 |
| Sodium Phosphate, Dibasic, Anhydrous | 0.0710 |
| Carbohydrates | |
| MOPS | 3.1389 |
| Putrescine, 2HCl | 0.0001 |
| Sodium Pyruvate | 0.0550 |
| Nucleosides | |
| Adenosine | 0.0175 |
| Guanosine | 0.0175 |
| Hypoxanthine, Na salt | 0.0103 |
| D-Ribose | 0.0175 |
| Thymidine | 0.0004 |
| Uridine | 0.0175 |

TABLE 10-continued

MediV 107 Formulation

| Component | g/L |
|---|---|
| Amino Acids | |
| L-Alanine | 0.0223 |
| L-Arginine HCl | 0.2739 |
| L-Asparagine H$_2$O | 0.0339 |
| L-Aspartic Acid | 0.0333 |
| L-Cysteine HCl H$_2$O | 0.0686 |
| L-Glutamic Acid | 0.0368 |
| Glycine | 0.0338 |
| L-Histidine HCl H$_2$O | 0.0735 |
| L-Isoleucine | 0.1069 |
| L-Leucine | 0.1115 |
| L-Lysine HCl | 0.1638 |
| L-Methionine | 0.0323 |
| L-Phenylalanine | 0.0685 |
| L-Proline | 0.0403 |
| L-Serine | 0.0473 |
| L-Threonine | 0.1011 |
| L-Tryptophan | 0.0192 |
| L-Tyrosine 2Na, Dihydrate | 0.0918 |
| L-Valine | 0.0997 |
| Vitamins | |
| d-Biotin (vit B7 and vit H) | 0.0000035 |
| D-Calcium Pantothenate | 0.00224 |
| Choline Chloride | 0.00898 |
| Cyanocobalamin (vit B12) | 0.00068 |
| Folic Acid | 0.00265 |
| myo-Inositol | 0.0126 |
| Niacinamide | 0.00202 |
| Pyridoxine HCl (vit B6) | 0.002031 |
| Riboflavin | 0.000219 |
| Thiamine HCl (vit B1) | 0.00217 |
| ∝Linoleic Acid, sodium salt | 0.000045 |
| ∝DL-Lipoic Acid | 0.000105 |
| Tropolone | 0.00025 |
| Trace Metals | |
| NH$_4$VO$_3$ | 6.5E−07 |
| AgNO$_3$ | 1.7E−07 |
| Aluminum Chloride 6H$_2$O | 0.0000012 |
| Ba(C$_2$H$_3$O$_2$)$_2$ | 2.55E−06 |
| Cadmium Chloride (CdCl$_2$) | 2.28E−06 |
| Chromium Chloride (CrCl$_3$, anhydrous) | 3.2E−07 |
| Cobalt Chloride 6H$_2$0 | 2.38E−06 |
| Cupric Sulfate, Pentahydrate | 0.0000029 |
| Ferric Nitrate, Nonahydrate | 0.00005 |
| Ferric Ammonium Citrate | 0.0014 |
| Ferrous Sulfate, Heptahydrate | 0.000417 |
| GeO$_2$ | 5.3E−07 |
| MnSO$_4$ H$_2$0 | 1.7E−07 |
| Molybdic Acid ammonium Salt | 1.24E−06 |
| Nikelous Sulfate (NiSO$_4$ 6H$_2$0) | 1.3E−07 |
| Potassium Bromide | 1.2E−07 |
| Potassium Iodide | 1.7E−07 |
| Rubidium Chloride | 1.21E−06 |
| Sodium Selenite | 0.000019 |
| Sodium Fluoride | 0.0000042 |
| Sodium Meta-Silicate •9H$_2$O | 0.00014 |
| Stannous Chloride | 1.2E−07 |
| Zinc Sulfate, Heptahydrate | 0.001295 |
| ZrOCl$_2$ 8H$_2$0 | 3.22E−06 |
| Other Components | |
| CDLC | 3X |
| Glucose (45%) | 4.5 g/L |
| L-Glutamine (200 mM) | 4 mM |
| CD Lipids (100X) | 3X |
| Wheat Peptone (25%) | 2.5 g/L |
| Insulin (5 mg/mL) | 5 ug/mL |
| T$_3$ (5 × 10$^{-9}$M) | 5 × 10$^{-12}$M |
| Hydrocortisone (10$^{-3}$M) | 5 × 10$^{-8}$M |
| PGE1 (50 µg/mL) | 25 ng/mL |
| EGF (1 µg/µL) | 5 ug/L |
| Osmolality | 360 |
| pH | 7.2~7.4 |

TABLE 11

Formulation of M18M

| Component | Final Amount or Concentration |
|---|---|
| DMNSO-7 powder concentrate | 21.22 g/L |
| Ferric ammonium citrate (FAC) Stock Soln. (1000X) | 1 mL/L |
| Polyethylene Glycol | 2 g/L |
| β-mercaptoethanol | 55 µm |
| Ethanolamine | 2.44 mg/mL |
| Tropolone | 5 µM |
| Wheat Peptone | 2.5 g/L |
| 2-Hydroxypropyl-b-Cyclodextrin | 125 mg/L |
| L-Proline | 183.4 mg/L |
| Copper Sulfate | 1.6 µg/L |
| CS5-20 (cholesterol source) | 25 mg/L |
| Chemically Defined Lipid Concentrate (CDLC) | 10 mL/L |
| Triiodo-L-Thyronine Sodium Salt (T3) | 5 pM |
| Sodium Bicarbonate | 3.024 g/L |
| Glutamine | 4 mM |
| Choline Chloride | 50 mg/L |
| L-Serine | 60.9 mg/L |
| Insulin | 20 mg/L |
| PGE$_1$ | 250 ng/L |
| Hydrocortisone | 5$^{-11}$M |
| EGF | 5 µg/L |

9.11 Example 11

Growth of Influenza Viruses to Very High Titers

This example describes the results of experiments showing growth of temperature sensitive, cold-adapted and attenuated influenza viruses to very high titer. In particular, these experiments resulted in virus titers of log$_{10}$ TCID$_{50}$/ml of 9 for four such viruses.

MDCK subclone 1-A or 1-B are grown in either MediV 105 or M18M for three days post-seeding, then immediately prior to infection the growth media is removed and fresh media, such as MediV 105; M18M or DMEM/F12 medium supplemented with 4.5 g/L glucose, 4 mM glutamine, and TrypLE (1:100) (Invitrogen) is added. Cells are then infected with reassortant temperature sensitive, cold-adapted, attenuated influenza viruses comprising the FluMist™ backbone (e.g., all the gene segments except those encoding the HA and NA proteins) and the HA and NA proteins from A/New Calcdonia, A/Wisconsin, A/Vietnam, or B/Malaysia.

Results from one experiment are presented in Table 12. Table 12 demonstrates that these procedures can result in viral titers of at least log$_{10}$ TCID$_{50}$/ml of 8.2 and as high as a log$_{10}$ TCID$_{50}$/ml of 9.1 at 2, 3, 4, and 5 days post infection. These data indicate that a media change or a supplementation of depleted nutrients prior to or during infection will result in increased in increased viral yields.

TABLE 12

| Strains | | 2 DPI | 3 DPI | 4 DPI | 5 DPI | Control |
|---|---|---|---|---|---|---|
| ca A/New Caledonia | #1 | 9.0 ± 0.06 | 9.0 ± 0.12 | 8.7 ± 0.00 | 8.7 ± 0.06 | 7.8 ± 0.06 |
| ca A/New Caledonia | #2 | 8.9 ± 0.06 | 9.0 ± 0.06 | 8.9 ± 0.10 | 8.8 ± 0.00 | |
| ca A/Wisconsin | #1 | 8.5 ± 0.06 | 8.6 ± 0.06 | 8.6 ± 0.00 | 8.5 ± 0.06 | 8.3 ± 0.00 |
| ca A/Wisconsin | #2 | 8.4 ± 0.06 | 8.7 ± 0.06 | 8.9 ± 0.12 | 8.8 ± 0.10 | |
| ca A/Vietnam | #1 | 8.8 ± 0.00 | 9.1 ± 0.06 | 9.0 ± 0.10 | 9.0 ± 0.00 | 8.2 ± 0.06 |
| ca A/Vietnam | #2 | 8.8 ± 0.06 | 9.0 ± 0.06 | 9.1 ± 0.06 | 9.0 ± 0.10 | |
| ca B/Malaysia | #1 | 8.5 ± 0.00 | 8.5 ± 0.00 | 8.3 ± 0.00 | 8.2 ± 0.06 | 7.9 ± 0.15 |
| ca B/Malaysia | #2 | 8.5 ± 0.00 | 8.4 ± 0.00 | 8.3 ± 0.00 | 8.2 ± 0.00 | |

Growth To Titers of >$\log_{10}$ TCID$_{50}$/ml 8.0

9.12 Example 12

Single Use Bioreactor Process

The standard bioreactors or fermenters (i.e., stainless steel or glass reactors) typically used for the production of vaccine material require cleaning, sterilization and validation before each use. To mitigate the need for cleaning and validation a disposable cell culture process has been developed using disposable bioreactor technology. This process allows for a shortened processing time, provides a significant cost savings and reduces the infrastructure required for production of vaccine material. The process makes use of a Single Use Bioreactor (SUB). Numerous SUB systems are commercially available and may be utilized in the process. Briefly, the SUB process involves growth of SF MDCK cells on microcarriers in growth medium for ~4 days, followed by infection of cells with the influenza virus after performing a medium exchange of replacing the growth medium with the infection medium. Alternatively, infection of the cells with the influenza virus may proceed directly, with no media exchange. The cells for seeding the SUB may be adherent and may be obtained from roller bottles or other readily scalable culture method used for growth of adherent cells.

Pilot studies demonstrated that while agitation rates of 50-100 rpm supported cell growth cells grown at 90-100 rpm lead to improved cell growth. Higher agitation rates were not tested in these studies. Pilot studies also demonstrated that a microcarrier concentration of about 2-3 g/L and a cell seeding density of ~9.0×10$^4$ cells/mL (corresponds to ~10-15 cells/MC) lead to improved cell growth and viral yields. In addition, the use of a glucose supplemented media also resulted in improved cell growth and viral yields. Based on these and other pilot studies SUB methods with and without a media exchange prior to infection were developed.

9.12.1. Materials

The A SUB from Hyclone (Hyclone, Part Nos. SH30715.01, SH30720.01 and SH3B1744.01) was used for this set of experiments. The SUB consists of the three primary components: 1. Outer support container with a mixer drive complete with control unit and an electrical heater jacket, 2. Single-Use Bioreactor BioProcess Container (BPC)—complete with mixer, sparger, vent filter inlet and outlet ports, plus ports for integration of sensor probes, and 3. Mixer Shaft Rod which is inserted into the bioreactor BPC through the mixing drive motor and locks into the disposable agitator assembly. Numerous custom alterations can be made to one or more components of the SUB apparatus, for example the outlet port can be enlarged to facilitate harvest and media exchange, similarly and in-line microcarrier filter can also facilitate harvest and media exchange.

MedIV 105 (see section 9.10) or MedIV 105 plus an additional 4.5 g/L glucose (final concentration 9.0 g/L, referred to as "MedIV 105+G") is utilized as the growth medium. When MedIV 105 is utilized the culture may be supplemented with 20 mM of Glucose on day 2 to 3 post-inoculation to prevent glucose depletion. The higher initial glucose concentration of MedIV+G can eliminate the need for glucose supplementation.

The infection medium consists of DMEM/F12, Glucose, Glutamine and TrypLE select. Table 13 shows the components and concentration of each in the infection medium.

TABLE 13

| Infection Medium | | |
|---|---|---|
| Component | Final Concentration | Amount Added per liter of DMEM/F12 |
| DMEM/F12 | 1 L/L | 1000 mL |
| Glucose | 4.5 g/L | 10 mL |
| L-Glutamine | 4 mM | 20 mL |
| TrypLE Select | 1:33 to 1:100 | 20 mL |

9.12.2. Method with Media Exchange

A microcarrier stock solution is prepared by swelling the microcarrier in buffer followed by a buffer wash and sterilization. Prior to use the buffer is removed and the appropriate media is added. For example 60 g of Cytodex 3 microcarrier (2 g/L of total working volume in SUB) is soaked in 3.0 L of Ca$^{2+}$ and Mg$^{2+}$ free PBS of pH 7.4 (50 mL/g Cytodex3) in a 5 L glass feeding bottle for at least 3 hours at room temperature. The supernatant is then aspirated out and replaced with 1.5 L of fresh Ca$^{2+}$ and Mg$^{2+}$ free PBS of pH 7.4. The microcarriers are then sterilized by autoclaving this feed bottle at 121° C. for 30 minutes. Just prior to inoculation the PBS solution is aspirated off and 4.0 L of DMEM/F12 medium is added and the sterile microcarriers are added to the SUB under sterile conditions. Alternatively, the Cytodex 3 microcarriers can be sterilized in-situ (i.e., inside SUB bags) using γ-irradiation.

Clone 1-B cells for seeding the SUB are obtained by scaling up from 1 frozen vial. Cells are grown in MedIV 105 or MedIV 105+G and may be scaled up as follows: on day 1 thaw vial into a T-75 flask; on day 3 split cells into T-225 flasks (seeding density≈5×10$^4$ cells/mL); on day 7 split cells into roller bottles (seeding density≈6.7×10$^4$ cells/mL); on day 10 split cells into additional roller bottles (seeding density≈6.7×10$^4$ cells/mL); on day 14 the cells from ~30-36 roller bottles are trypsinized and used to inoculate SUB bioreactor. The inoculation parameters are indicated in Table 14. Pooled trypsinized cells collected from roller bottles are transferred to the SUB containing Cytodex 3 microcarriers in 30 L of SFMV 105 medium through the inoculum addition line of the BPC using a Peristaltic pump. The cultures may be supplemented with 20 mM Glucose on day 3 post-inoculation to prevent glucose depletion.

The cells are grown for 4 days under the growth parameter conditions detailed in Table 15. The pH is controlled using the Applikon controller, initially by sparging $CO_2$ and at later cultures stages by adding base (NaOH, 1M). DO is controlled at ≥50% using the Applikon controller by sparging $O_2$. During cell growth is acceptable for DO to be as high as 100% and drop as low as 35%. Temperature is controlled at the appropriate values with the Hyclone controller. Agitation is controlled with the Hyclone controller at 100 rpm.

TABLE 14

Inoculation Parameters

| | |
|---|---|
| Working Volume | 30 ± 1 L |
| Microcarrier (MC) concentration | 2 to 3 ± 0.2 g/L |
| Amount of microcarrier | 60 to 90 ± 1 g |
| Cells/MC (calculated) | 15 ± 5 |
| Seeding density (cells/mL) | $9.0 ± 1.5 \times 10^4$ |

TABLE 15

Growth Parameters

| | |
|---|---|
| Agitation | 100 ± 10 rpm |
| Temperature | 37 (±0.5) ° C. |
| pH | 7.4 (±0.1) |
| Dissolved Oxygen (DO) [Air saturation] | ≥35% [Controlled at 50%] |
| $O_2$ Flow rate [maximum] (L/min) | 1.0 ± 0.2 |
| $CO_2$ Flow rate [maximum] (L/min) | 0.20 ± 0.04 |

Infection is done at 4±0.5 days post seeding. Prior to infection, a nuclei count may be performed. Cells should reach between $0.5-2.0 \times 10^6$ cells/mL at this time and are generally expected to reach a cell density of at least $\sim 1 \times 10^6$ cells/mL. After the nuclei count if desired, all control loops are disabled and the micro carrier beads are allowed to settle for ~45 minutes. A medium exchange is then performed where the growth medium is pumped out through the medium exchange port of the SUB and infection medium is added through the medium addition port to a final volume of 30 L. Approximately 20-24 L are removed and the same amount of fresh infection medium is added. This corresponds to approximately 66-80% medium exchange. The parameters for infection are given in Table 16.

TABLE 16

Parameters for Infection

| | |
|---|---|
| Working Volume | 30 L |
| Agitation | 100 ± 10 rpm |
| Temperature | 33 (±0.5) ° C. |
| pH | 7.4 (±0.1) |
| Dissolved Oxygen (DO) [Air saturation] | ≥35% [Controlled at 50%] |
| O2 Flow rate [maximum] (L/min) | 1.0 ± 0.2 |
| CO2 Flow rate [maximum] (L/min) | 0.20 ± 0.04 |

The infection may be done at an MOI (Multiplicity of Infection) of ~0.001-0.003 FFU/cell (refer to the formula below).

Amount of viruses in μL added to S.U.B=
Total cells in SUB×
MOI (FFU/cell)/$10^{Virus\ FFATiter}$ (FFU/mL)×1000.

Alternatively, to minimize process steps $2 \times 10^3$ FFU/mL of virus may be added. This will correspond to an MOI of ~0.001-0.003 FFU/cell. Under these conditions the amount of virus in μL added to S.U.B =Volume in reactor (mL)×2×
$10^3$ FFU/mL/$10^{Virus\ FFATiter}$ (FFU/mL)×1000.

In-process sampling procedures may be utilized at several steps for monitoring. Pre-infection 2×10 mL of cell suspension is collected daily from day 0 to day 4 post seeding for nuclei count, pictures and pH and metabolite (glucose, glutamine, lactate, $NH_4^+$) analysis. Post-infection 2×5 mL samples are drawn on day 2 and day 3 post infection. The samples are stabilized with Sucrose Phosphate (ratio of Sucrose phosphate to Virus sup=1:9). These samples will be frozen immediately and stored at −80° C. and may be used to determine viral titers.

Virus harvest is obtained on day 3 post infection (+/−12 h). The controllers on the SUB and Applikon are turned-off and the microcarriers are allowed to settle for at least 45 min. Then the supernatant is transferred to a sterile disposable bag and stabilized with sucrose phosphate at a 1:9 ratio (V/V) (Sucrose phosphate:Virus Harvest=1:9). The Sucrose phosphate should be added by volume and not by weight.

9.12.3. Results with Media Exchange

Summarized here are the results of multiple SUB production runs testing the different medium, inoculation and infection parameters described in section 9.12.2. As shown in Table 18, all the variation tested resulted in peak viral titers of at least 8.0 $\log_{10}$ FFU/mL demonstrating that the SUB process with media exchange is robust.

For one B/Malaysia production run (SUB run A) the microcarrier (MC) concentration was 3 g/L of working volume (30 L) and the cell seeding density was 10 cells/MC or ~$9.0 \times 10^4$ cells/mL. The culture was supplemented with 20 mM of Glucose on day 3 post-inoculation to prevent glucose depletion. MDCK subclone 1-B was used and the cell density reached ~$1.3 \times 10^6$ cells/mL by day 4 post inoculation. The remaining growth parameters shown in Table 15 were maintained as described throughout the growth phase. Table 17 shows the cell growth data and the doubling time for the B/Malaysia production run. The cell growth curve is plotted in FIG. 13, as well as, the metabolite analysis of glucose, lactate, glutamine and ammonium ion concentration measured by Bioprofile for the B/Malaysia production run.

TABLE 17

Cell Growth

| Time (h) | Total Cell Density $\times 10^6$ cells/mL | Doubling Time (h) |
|---|---|---|
| 0.15 | 0.09 | |
| 21.67 | 0.10 | 141.55 |
| 46.00 | 0.30 | 15.35 |
| 65.33 | 0.60 | 19.57 |
| 70.00 | 0.69 | 21.84 |
| 88 83 | 1.30 | 20.61 |

Doubling time is about 20 h during the exponential phase. On day 4 post seeding ~67% of the medium was exchanged for infection medium (see above) containing TrypLE select at a final concentration of 1:100. The cells were then infected with B/Malaysia/2506/04 at an MOI of 0.001 FFU/cell. The infection parameters shown in Table 16 were maintained throughout the infection phase. Samples taken at 2 and 3 days post infection (dpi) were analyzed using the Focal Fluorescent Assay (FFA) to determine the virus infectivity. Virus titer was seen to peak at ~2 dpi at around 8.0 $\log_{10}$ FFU/mL. While the peak viral titers obtained using TrypLE at a final concentration of 1:100 from this and several other runs were at least 8.0 $\log_{10}$ FFU/mL, lower titers were occasionally seen (data not shown), and so higher TrypLE concentrations (1:33 to 1:50) were generally used.

Two SUB runs were performed using a microcarrier concentration of 2 g/L and MedIV 105+G as the growth medium without any additional glucose supplementation. MDCK subclone 1-B was used at a seeding density of ~$9.0 \times 10^4$ cells/mL (corresponds to ~15 cells/MC). Prior to infection ~80% of the medium was exchanged and TrypLE select was added at a final concentration of 1:100 (SUB run B) or 1:50 (SUB run C). The cells were infected at a virus concentration of $2 \times 10^3$ FFU/mL. The peak viral titers for these runs were 8.4 $\log_{10}$ FFU/mL A/Wisconsin (SUB run B) and 8.7 $\log_{10}$ FFU/mL A/New Calcedonia (SUB run C).

Six additional production runs (SUB runs D-I) were performed using a microcarrier concentration of 2 g/L and MedIV 105+G as the growth medium without any additional glucose supplementation. As before the MDCK subclone 1-B was used at a seeding density of ~$9.0 \times 10^4$ cells/mL, which here corresponds to ~15 cells/MC. The remaining growth parameters were maintained as detailed in Table 15. On day 4±0.5 post seeding ~66% of growth media (MedIV 105+G) were removed and the same amount of infection medium (see Table 13) was added containing TrypLE select at a final concentration of 1:33. The cells were then infected with A/New Calcedonia/20/99; A/Wisconsin/67/05; or B/Malaysia/2506/04 at a virus concentration of $2 \times 10^3$ FFU/mL and the infection parameters shown in Table 16 were maintained throughout the infection phase. The peak viral titers for the SUB runs are shown in Table 18 and range from 8.55-8.75 $\log_{10}$ FFU/mL. The growth, glucose, lactate, glutamine and ammonium ion profiles were comparable to that seen for SUB run A (see FIG. 13 and data not shown)

TABLE 18

Peak Viral Titers for SUB runs

| SUB run | Peak Titer ($\log_{10}$ FFU/mL) | Virus |
| --- | --- | --- |
| A | 8.0 | B/Malaysia |
| B | 8.4 | A/Wisconsin |
| C | 8.7 | A/New Caledonia |
| D | 8.6 | B/Malaysia |
| E | 8.7 | B/Malaysia |
| F | 8.7 | A/New Caledonia |
| G | 8.8 | A/New Caledonia |
| H | 8.6 | A/Wisconsin |
| I | 8.6 | A/Wisconsin |

9.12.4. Results without Media Exchange

Elimination of the media exchange step will reduce costs and improve process efficiency. Initial testing at a TrypLE dilution of 1:100 (~0.01×) suggested that conditioned growth media may comprise one or more components which inhibit the action of the TrypLE and thus inhibit the growth of virus (data not shown). Pilot experiments were performed in which the concentration of TrypLE was varied. Briefly, MDCK cells grown in a 2 L bioreactor for 4 days under standard conditions (mother culture). The mother culture was then used to inoculate shake flasks with different levels of medium exchange and TrypLE concentrations, just prior to infection with A/New Calcdonia. Four different dilutions/concentrations of TrypLE were used 1:100 (~0.01×); 1:50 (~0.02×); 1:33 (~0.03×); and 1:25 (~0.04×). Flasks were sampled at 2 and 3 dpi for virus titer. The viral titers obtained for each medium exchange ratio at 2 and 3 dpi are plotted in FIG. 14A. These data show that even without any media exchange, adding TrypLE at 1:25-1:33, yields a titer close to 8 $\log_{10}$ FFU/mL. Based on these data a 1:16 dilution of TrypLE should yield an high titer without any medium exchange. A similar experiment was performed at higher TrypLE concentrations. Briefly, a mother culture was prepared as described above and used to inoculate shake flasks with no media exchange at 1:1-1:25 (corresponding to 0.5×–0.04× TrypLE concentrations) just prior to infection with A/New Calcdonia. The peak viral titer was determined at 2 and 3 dpi and plotted in FIG. 14B. Here, viral titers of greater then 8 logs were obtained for the first time without media exchange. These data indicate that the optimal TrypLE concentration is between 1:25-1:12.5 dilution and that higher concentrations of TrypLE do not improve viral yield. Based on these results the production of two additional viral strains, B/Malaysia/2506/04 and A/Vietnam/1203/2004, were examined with and without media exchange (using 1:33 and 1:12.5 dilution of TrypLE, respectively). The viral titers over time are plotted in FIG. 14C. The peak viral titers for B/Malaysia/2506/04 were 8.9 and 8.7 $\log_{10}$ FFU/mL (with and without media exchange, respectively). Similarly, the peak viral titers for A/Vietnam/1203/2004 were 8.6 and 8.0 $\log_{10}$ FFU/mL (with and without media exchange, respectively). Thus, increasing the amount of TrypLE up to 1:12.5 dilution (corresponding to 0.08×) can compensate for the effects of the conditioned media resulting in peak viral titers without media exchange of at least 8 log 10 FFU/mL.

9.13 Example 13

Optimization of MOI

Because of the continual emergence (or re-emergence) of different influenza strains, new influenza vaccines are generated each season based on the circulating influenza strains. Unfortunately, some influenza vaccine strains (e.g., cold adapted temperature reassortant vaccine strains) are more difficult to grow to high titers. The titer of the bioreactor not only defines production capacity but also impacts the cost of manufacturing product thus improving viral titer (i.e., peak viral titer) is desirable. As mentioned above a number of parameters has been examined to optimize productivity of vaccine strains. Summarized here are the results of the studies for increasing productivity (i.e., viral titer) for several strains. These studies identified the MOI (virus particles used for infection per MDCK cell) as a parameter which can be readily tested and adjusted to optimize yield and allow for the rapid scale up and production of seasonal and pandemic vaccine strains.

These studies were carried out by growing the MDCK subclone 1-B cells in a bioreactor and infecting the cells in shake flasks with different amounts of virus. The details of the study are as follows: M-32+G containing Cytodex 3 micro carrier beads at 2 g/L was inoculated with MDCK subclone 1-B cells at ~15 cells/microcarrier in a 3 L bioreactor vessel. The cells were grown at 37° C., 90 rpm, pH 7.4 and, 50% DO (controlled using $O_2$ and $CO_2$ sparge). At ~4 days post seeding (dps),), 66% of the growth medium in the bioreactor was exchanged with infection medium (DMEM/F12+4.5 g/L D-glucose+4 mM L-glutamine+1× TrypLE select at 1:33 final dilution). Equal amounts of culture (30 ml) were transferred to different 125 ml shake flasks. These shake flasks were infected with different amounts of a specific virus strain (i.e., 2, 20, 200, 2000 and 20000 FFU/ml, corresponding to approximately $1 \times 10^{-6}$, $1 \times 10^{-5}$, $1 \times 10^{-4}$, $1 \times 10^{-3}$ and $1 \times 10^{-2}$ FFU/cell, respectively). Post infection the flasks were incubated at 33° C. and, 100 rpm. A number of parameters were monitored including the viable cell density, metabolite concentration (both before and after infection) as well as the viral titer at various times post infection (e.g., 1, 2, 3 and, 4 days post infection (dpi)). The peak viral titer results for four strains tested in these studies are shown in Table 19. For each strain tested the peak viral titer was seen to increase when the MOI was reduced from ~$1\times10^{-3}$ FFU/cell (the MOI used in the SUB process described in Section 9.12 above) to ~$1\times10^{-4}$ FFU/cell. The observed increase in viral peak titer ranged from 0.3 $\log_{10}$ FFU/ml to 1.3 $\log_{10}$ FFU/ml. It should be noted that in some instances the peak viral titers were obtained on different days post infection (i.e., 2 dpi or 3 dpi). This may be due to differences in viral amplification kinetics at a lower MOI of $1\times10^{-4}$ FFU/cell compared to a MOI of $1\times10^{-3}$ FFU/cell, should this trend be seen in production bioreactors the viral harvest times should be adjusted accordingly.

A bioreactor study was performed to confirm the shake flask results. For this study five parallel master cell cultures were prepared in 3 L bioreactors as described above. The viable cell density and cell metabolism profiles of glutamine, $NH_4+$, glucose and lactate were comparable in all the bioreactors (data not shown). At ~4 days post seeding (dps), 66% of the growth medium in the bioreactors was exchanged for infection medium DMEM/F12+4.5 g/L D-glucose+4 mM L-glutamine+10× TrypLE select at 1:330 final dilution). The five cultures were infected with A/Solomon Islands/3/06 at different amounts 2, 20, 200, 2000 or 20000 FFU/ml (corresponding to MOIs of approximately $1\times10^{-6}$, $1\times10^{-5}$, $1\times10^{-4}$, $1\times10^{-3}$ and $1\times10^{-2}$ FFU/cell, respectively) and incubated at 33° C. All other growth parameters post-infection were the same as for the growth of the master cell cultures pre-infections. FIG. 15 plots the viral titer over time (hours post infection) obtained using different MOIs. The boxed area (expanded to the right) shows that at three days post infection the culture infected at 2000 FFU/mL had a peak viral titer of 8.3 $\log_{10}$ FFU/mL while the culture infected at 20 FFU/mL had a peak viral titer of 8.5 $\log_{10}$ FFU/mL (a 0.2 $\log_{10}$ FFU/mL improvement). Similarly, at four days post infection the culture infected at 2 FFU/mL also reached a peak titer of 8.5 $\log_{10}$ FFU/mL. Together, these studies indicate that decreasing the MOI can result in increased viral titers and such a method may prove useful for increasing the production yield of certain vaccine strains. These studies further indicate that the optimum harvest time may have to be determined based on the MOI used.

TABLE 19

Optimization of MOI in Shaking Flasks

| Virus Strain | Peak Virus Titer at MOI (in FFU/cell) of | | Improvement in titer |
|---|---|---|---|
| | 0.001-0.003* | 0.0001** | |
| A/Wisconsin/67/05 | 8.7 | 9 | 0.3 $\text{Log}_{10}$FFU/mL |
| A/Solomon Islands/3/06 | 8.3 | 9.2 | 0.9 $\text{Log}_{10}$FFU/mL |
| A/California/07/2004 | 7.1 | 7.9 | 0.8 $\text{Log}_{10}$FFU/mL |
| A/Hong Kong/491 H5+ 486 N1/1997 | 7.9 | 9.2*** | 1.3 $\text{Log}_{10}$FFU/mL |

Note:
*MOI for SUB-like process = 2000 FFU/mL
**MOI corresponds to 200 FFU/mL
***Peak viral titer observed at MOI of 1.0E−06 FFU/cell 9.14 Example 14

Bead to Bead Transfer

Large scale cultivation of cells requires a scale up of the number of cell in the culture. When adherent cells are used the scale up process generally involves sequential dissociation of cells from flasks or microcarriers, for example by protease treatment, dilution of the dissociated cells into a larger flask or into a larger number of microcarriers. Minimizing the number of washing and/or medium exchange steps during the scale up process can enhance efficiency and reduce the likelihood of contamination. The SUB method described above requires the use of cells harvested from 30 to 36 separate roller bottles each of which must be trypsinized and harvested separately. Described below is one method that can be utilized to reduce the number of handling steps used to scale up from a 3 L vessel to a 20 L vessel. Similar strategies can be implemented for use in larger bioreactor process such as the 30 L SUB process described above.

3 L Bioreactor Preparation:
1. Add 4 g of Cytodex3 to a 3 L bioreactor. Add 500 mL of DPBS (PBS w/o Ca, Mg) to hydrate the microcarriers for 4-6 hours. 2. Use the dip tube to remove 300 mL of DPBS without disturbing microcarriers from the bottom. Add 300 mL of fresh DPBS and autoclave vessel for 30 minutes at 121 C. 3. After reactor has cooled, remove 300 mL of DPBS and add 300 mL of medium (M-32) to the vessel. Stir vessel contents for 10 minutes at 200 rpm to completely mix reactor contents and to get all microcarriers off the bottom of the vessel. 4. Stop agitation and remove 300 mL of medium after all microcarriers have settled. 5. Add 1.6 L of fresh basal medium into the reactor and allow parameters to stabilize overnight. The process parameters are: pH 7.2, Temperature 37 C, Agitation 120 rpm, Air sparge rate 50 mL/min.

20 L Bioreactor Preparation:
Add 28 g of Cytodex3 to a 5 L bottle. Add 3 L of DPBS (w/o Ca, Mg) to hydrate the microcarriers for 4-6 hours. Remove 2 L of DPBS without disturbing microcarriers from the bottom. Add 2 L of fresh DPBS and autoclave vessel for 30 minutes at 121 C. 2. Remove 2 L of DPBS and add 2 L of medium to the bottle. Shake bottle vigorously to ensure microcarriers are in suspension. Allow microcarriers to settle before removing 2 L of medium. Add fresh medium to the microcarriers to bring microcarrier solution to a total volume of 3 L. 3. Add fresh medium and microcarrier solution to ensure total volume in bioreactor is 14 L and allow process parameters to stabilize overnight. The process parameters are: pH 7.2, Temperature 37 C, Agitation 120 rpm, Air sparge rate 400 mL/min.

3 L Bioreactor Growth Phase Operation:
Calibrate pH and Dissolved Oxygen readings after sampling and analysis through NOVA Bioprofile. 2. Add culture harvested from cell factories to inoculate bioreactor at a target cell density of 9E4 cells/mL (15 cells per microcarrier bead). Add medium to reach a total working volume of 2 L. 3. Start D.O. control with a set-point of 50%. 4. Sample everyday for analysis with NOVA, Nucleocounter and for microscope imaging.

Bead to Bead Transfer Protocol at Scale:
After 96 hours of cell growth in the 3 L vessel, switch off the agitator, gas flow and DO and temperature controls. Allow microcarriers to settle. 2. Remove medium (>80%) through dip tube but ensure that microcarriers are not disturbed from the bottom of the vessel. 3. Add DPBS (PBS w/o Ca, Mg) to bring the volume up to the original working volume. 4. Increase agitation set point to 180 rpm. Switch on the agitator for a period of 10 minutes to wash microcarriers of any remaining medium. 5. Switch off the agitator and allow microcarriers to settle to the bottom. 6. Remove ~50% of the liquid in the bioreactor through the dip tube. Ensure that the temperature probe and agitator are still completely immersed after the removal. (Volume remaining is approximately 1 L). 7. Switch on the agitator and temperature control. Wait till the temperature in the reactor is 37 C. 8. Add 5× TrypLE (5-7% of remaining volume) to the bioreactor. 9. Add 1M Sodium Carbonate to adjust the pH of the reactor contents to 7.9+/−0.1. 10. Allow trypsinization for 50+/−10 minutes with intermittent sampling and observation under the microscope to ensure cells have detached. 11. Add 5× lima bean trypsin inhibitor (LBTI) in exactly the same volume as the TrypLE. 12. Add fresh medium to bring up the volume to original working volume (2 L). 13. Transfer all reactor contents to the 20 L bioreactor (1:8 split).

Infection Parameters:

Under the bead to bead transfer conditions utilized here, the cells exhibited a slightly slower growth post bead to bead transfer which lead to infection being delayed by one day (infection on ~day 5) as compared to transfer from roller bottles (infection on ~day 4). Infection was performed when cell density reached ~1×10$^6$ cells/mL essentially as described for the SUB process (see, Section 9.12 above). Although infection was delayed by one day, the peak viral titers using bead to bead transfer were comparable to those obtained using transfer conditions similar to those described in Section 9.12 above (see Table 20). Accordingly, the use of bead to bead transfer methods can reduce the number of manipulations without sacrificing viral yield.

TABLE 20

Peak Virus Titers

| Virus Strain | Bead to Bead Transfer | Transfer from Roller Bottles |
|---|---|---|
| B/Malaysia/2506/04 | 8.8 | 8.5 |
| A/Wisconsin/67/05 | 8.5 | 8.5 |
| A/Solomon Islands/3/06 | 8.1 | 8.2 |

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes. Citation or discussion of a reference herein shall not be construed as an admission that such is prior art to the present invention, and citation of a patent shall not be construed as an admission of its validity.

The invention claimed is:

1. A Madin-Darby Canine Kidney (MCDK) cell identified by ATCC Accession No. PTA-7909 or ATCC Accession No. PTA-7910, wherein a cell culture composition comprising a plurality of the MDCK cells supports replication of an influenza virus to a base 10 logarithm of the median tissue culture infection dose per milliliter ($\log_{10}$ TCID$_{50}$/mL) of 7.8 or greater or to a base 10 logarithm of fluorescent focus units per milliliter ($\log_{10}$ FFU/mL) of 7.8 or greater.

2. The MDCK cell of claim 1, wherein the MDCK cells are adherent, non-tumorigenic and/or non-oncogenic.

3. The MDCK cell of claim 1, wherein the influenza virus is cold-adapted, attenuated and/or temperature sensitive.

4. The MDCK cell of claim 1, wherein the influenza virus comprises one or more gene segments of influenza strain A/Ann Arbor/6/60 or B/Ann Arbor/1/66.

5. The MDCK cell of claim 1, wherein the composition comprises a serum-free cell culture medium.

6. The MDCK cell of claim 5, wherein the cell culture medium is selected from the group consisting of MediV-105, MediV-105 supplemented with glucose, M-32, M-32 supplemented with glucose, MediV-107 and MediV-107 supplemented with glucose.

7. A method for replicating an influenza virus in a bioreactor, comprising:
(a) culturing the Madin-Darby Canine Kidney (MDCK) cells of claim 1 in a bioreactor in the presence of microcarriers under culture conditions that include agitation, thereby producing cultured cells;
(b) infecting the cultured cells with a cold-adapted influenza virus, thereby producing infected cells; and
(c) incubating the infected cells under conditions that permit replication of the influenza virus.

8. The method of claim 7, wherein the culture conditions are serum-free.

9. The method of claim 8, wherein the culture conditions include a cell culture medium selected from the group consisting of MediV-105, MediV-105 supplemented with glucose, M-32, M-32 supplemented with glucose, MediV-107 and MediV-107 supplemented with glucose.

10. The method of claim 7, wherein the agitation is at a rate of 80 rpm to 120 rpm.

11. The method of claim 10, wherein the agitation rate is 90 rpm to 100 rpm.

12. The method claim 7, wherein fresh medium or additional medium components are added to the cell culture prior to, during, or after step (b).

13. The method of claim 12, wherein the fresh medium or additional medium components comprise a protease.

14. The method of claim 13, wherein the protease is a serine protease.

15. The method of claim 14, wherein the protease is trypsin.

16. The method of claim 7, wherein none or some of the cell culture medium is removed and replaced with fresh medium prior to or during step (b).

17. The method of claim 7, wherein step (b) is carried out at a Multiplicity Of Infection (MOI) of between about 0.00001 FFU/cell to about 0.003 FFU/cell.

18. The method of claim 17, wherein step (b) is carried out at a MOI of between about 0.001 FFU/cell to about 0.003 FFU/cell.

19. The method of claim 7, wherein a protease is added to the bioreactor before, simultaneously with, or after step (b).

20. The method of claim 19, wherein the protease is a serine protease.

21. The method of claim 20, wherein the protease is trypsin.

22. The method of claim 7, wherein the bioreactor is a single-use bioreactor (SUB).

23. The MDCK cell of claim 1, wherein the cell is identified by ATCC Accession No. PTA-7909.

24. The MDCK cell of claim 1, wherein the cell is identified by ATCC Accession No. PTA-7910.

* * * * *